United States Patent
Jishage et al.

(10) Patent No.: US 11,612,149 B2
(45) Date of Patent: Mar. 28, 2023

(54) NON-HUMAN ANIMAL HAVING HUMAN CD3 GENE SUBSTITUTED FOR ENDOGENOUS CD3 GENE

(71) Applicant: CHUGAI SEIYAKU KABUSHIKI KAISHA, Tokyo (JP)

(72) Inventors: Koichi Jishage, Shizuoka (JP); Otoya Ueda, Shizuoka (JP); Naoko Wada, Shizuoka (JP); Takahiro Ishiguro, Tokyo (JP); Yasuko Kinoshita, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/743,248

(22) PCT Filed: Jul. 8, 2016

(86) PCT No.: PCT/JP2016/070276
§ 371 (c)(1),
(2) Date: Jan. 9, 2018

(87) PCT Pub. No.: WO2017/010423
PCT Pub. Date: Jan. 19, 2017

(65) Prior Publication Data
US 2018/0192623 A1    Jul. 12, 2018

(30) Foreign Application Priority Data

Jul. 10, 2015 (JP) .............................. JP2015-139023
Mar. 14, 2016 (JP) .............................. JP2016-049919

(51) Int. Cl.
| | |
|---|---|
| *A01K 67/027* | (2006.01) |
| *C07K 16/28* | (2006.01) |
| *C07K 14/725* | (2006.01) |
| *C12N 15/85* | (2006.01) |
| *C12N 15/09* | (2006.01) |
| *G01N 33/50* | (2006.01) |
| *G01N 33/15* | (2006.01) |

(52) U.S. Cl.
CPC ...... *A01K 67/0278* (2013.01); *C07K 14/7051* (2013.01); *C07K 16/2809* (2013.01); *C12N 15/8509* (2013.01); *G01N 33/15* (2013.01); *G01N 33/5008* (2013.01); *A01K 2207/12* (2013.01); *A01K 2217/072* (2013.01); *A01K 2227/105* (2013.01); *A01K 2267/0325* (2013.01); *A01K 2267/0331* (2013.01); *C12N 15/09* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 7,888,121 | B2 | 2/2011 | Urnov et al. |
| 8,106,255 | B2 | 1/2012 | Carroll et al. |
| 10,822,420 | B2 | 11/2020 | Jishage et al. |
| 2005/0064474 | A1 | 3/2005 | Urnov et al. |
| 2005/0208489 | A1 | 9/2005 | Carroll et al. |
| 2012/0117671 | A1 | 5/2012 | Yoneyama et al. |
| 2015/0225481 | A1 | 8/2015 | Jishage et al. |
| 2015/0266966 | A1* | 9/2015 | Smith ............... C07K 16/2887 424/136.1 |
| 2019/0174731 | A1 | 6/2019 | Jishage et al. |

FOREIGN PATENT DOCUMENTS

| | | |
|---|---|---|
| EP | 2896291 A1 | 7/2015 |
| JP | 2017536126 A | 12/2017 |
| WO | WO-9937764 A2 | 7/1999 |
| WO | WO-03006639 A1 | 1/2003 |
| WO | WO-2012143524 A2 | 10/2012 |
| WO | WO-2014042251 A1 | 3/2014 |
| WO | WO-2015095392 A1 | 6/2015 |
| WO | WO-2016085889 A1 | 6/2016 |
| WO | WO 2016085889 A1 | 6/2016 |
| WO | WO 2018038046 A1 | 3/2018 |

OTHER PUBLICATIONS

Wang (International Immunology, 10(12): 1777-1778, 1998 (Year: 1998).*
Tong (Nature, 467: 211-213, 2010 (Year: 2010).*
Hong (Stem Cell and Development, 21(9): 1571-1586, 2012). (Year: 2012).*
Munoz (2009) Stem Cell Rev. and Rep., vol. 5, 6-9, (Year: 2009).*
Li (Cell, 135(7): 1299-1310, 2008 (Year: 2008).*
Buehr (Cell, 135: 1287-1298, 2008) (Year: 2008).*
Brevini, (Theriogenology, vol. 74, pp. 544-550, 2010) (Year: 2010).*
Paris (2010, Theriogenology, vol. 74, pp. 516-524 (Year: 2010).*

(Continued)

*Primary Examiner* — Emily A Cordas
*Assistant Examiner* — Maytee Marie Contes De Jesus
(74) *Attorney, Agent, or Firm* — Nixon & Vanderhye P.C.

(57) ABSTRACT

The present invention provides genetically modified non-human animals which are deficient in at least one or more types of CD3 genes selected from the group consisting of endogenous CD3ε, CD3δ, and CD3γ in its genome and functionally express at least one or more types of human CD3 genes selected from the group consisting of human CD3ε, CD3δ, and CD3γ. In the genetically modified non-human animals of the present invention, mature T cell differentiation and production can take place, and immunocompetent cells including T cells can exert their functions. The genetically modified non-human animals of the present invention enable efficient evaluation and screening in the development of therapeutic agents and therapeutic methods that use human CD3-mediated targeted drugs.

8 Claims, 20 Drawing Sheets

Specification includes a Sequence Listing.

(56) References Cited

OTHER PUBLICATIONS

Ezashi (Annu. Rev. Anim. Biosci. 2016. 4:223-53) (Year: 2016).*
Bettini, M. L., et al., "Membrane Association of the CD3ε Signaling Domain is Required for Optimal T Cell Development and Function," J. Immunol. 193:258-267 (2014).
Billerbeck, E., et al., "Development of human CD4+FoxP3+ regulatory T cells in human stem cell factor-, granulocyte-macrophage colony-stimulating factor-, and interleukin-3-expressing NOD-SCID IL2Rγ$^{null}$ humanized mice," Blood 117(11):3076-3086 (2011).
Dejarnette, J. B., "Specific requirement for CD3ε in T cell development," Proc. Natl. Acad., Sci. 95:14909-14914 (1998).
Fernández-Malavá, E., et al., "Overlapping functions of human CD3δ and CD3γ in αβ T-cell development revealed in a humanized CD3γ-deficient mouse," Blood 108(10):3420-3427 (2006).
International Search Report for International Patent Application No. PCT/JP2016/070276, dated Oct. 4, 2016, 2 pages.
Malissen, M., et al., "Altered T cell development in mice with a targeted mutation of the CD3-ε gene," The EMBO Journal 14(19):4641-4653 (1995).
Pan, Q., et al., "Different role for mouse and human CD3δ/ε heterodimer in preT cell receptor (preTCR) function: Human CD3δ/ε heterodimer restores the defective preTCR function in CD3γ- and CD3γδ-deficient mice," Mol. Immunol. 43:1741-1750 (2006).
Rongvaux, A., et al., "Development and function of human innate immune cells in a humanized mouse model," Nat. Biotechnol. 32(4):364-372 (2014).
Wang, B., et al., "A block in both early T lymphocyte and natural killer cell development in transgenic mice with high-copy numbers of the human CD3E gene," Proc. Natl. Acad. Sci. 91:9402-9406 (1994).
Wang, N., et al., "Expression of CD3ε transgene in CD3ε$^{null}$ mice does not restore CD3γ and δ but efficiently rescues T cell development from a subpopulation of prothymocytes," Intl. Immunol. 10(12):1777-1788 (1998).
Xu, C., et al., "Regulation of T Cell Receptor Activation by Dynamic Membrane Binding of the CD3ε Cytoplasmic Tyrosine-Based Motif," Cell 135(4):702-713 (2008).
Third Party Observation for International Patent Application No. PCT/JP2016/070276, dated Nov. 9, 2017, 3 pages.
Brinster, R. L., et al., "Introns increase transcriptional efficiency in transgenic mice," Proc Natl Acad Sci. USA, 85:836-840 (1988).
Göbel, T. W. F. and Dangy, J.-P., "Evidence for a Stepwise Evolution of the CD3 Family," J Immunol., 164:879-883 (2000).
Kuhn, C., et al., "Human CD3 Transgenic Mice: Preclinical Testing of Antibodies Promoting Immune Tolerance," Sci Transl Med., 3(68):68ra10 (2011).
Liu, B., et al., "Suppression of Liver Regeneration and Hepatocyte Proliferation in Hepatocyte-Targeted Glypican 3 Transgenic Mice," Hepatology 52:1060-1067 (2010).
Ryan, K. and Bauer, D. L. V., "Finishing touches: Post-translational modification of protein factors involved in mammalian pre-mRNA 3' end formation," Intl J Biochem Cell Biol., 40:2384-2396 (2008).
Vlasova, I. A. and Bohjanen, P. R., "Posttranscriptional regulation of gene networks by GU-rich elements and CELF proteins," RNA Biol., 5(4):201-207 (2008).
Von Roretz, C. and Gallouzi, I.-E., "Decoding ARE-mediated decay: is microRNA part of the equation?" J Cell Biol., 181(2):189-194 (2008).
Weidle, U. H., et al., "Tumor-Antigen-Binding Bispecific Antibodies for Cancer Treatment," Semin Oncol., 41(5):653-660 (2014).
Willinger, T., et al., "Human IL-3/GM-CSF knock-in mice support human alveolar macrophage development and human immune responses in the lung," PNAS, 108(6):2390-2395 (2011).
Feng, M., et al., "Therapeutically targeting glypican-3 via a conformation-specific single-domain antibody in hepatocellular carcinoma," PNAS, 110(12):E1083-E1091 (2013).
Feng, M. and Ho, M., "Glypican-3 antibodies: a new therapeutic target for liver cancer," FEBS Lett., 588(2):377-382 (2014).
Lute, K. D., et al., "Human CTLA4 knock-in mice unravel the quantitative link between tumor immunity and autoimmunity induced by anti-CTLA-4 antibodies," Blood, 106(9):3127-3133 (2005).
Brevini, T. A. L., et al., "No shortcuts to pig embryonic stem cells," Theriogenology, 74:544-550 (2010).
Christian, M., et al., "Targeting DNA Double-Strand Breaks with TAL Effector Nucleases," Genetics, 186:757-761 (2010).
Ezashi, T., et al., "Pluripotent Stem Cells from Domesticated Mammals," Annu Rev Anim Biosci., 4:223-253 (2016).
Geurts, A. M., et al., "Knockout Rats Produced Using Designed Zinc Finger Nucleases," Science, 325(5939):433 (2009).
Hauschild, J., et al., "Efficient generation of a biallelic knockout in pigs using zinc-finger nucleases," PNAS, 108(29):12013-12017 (2011).
Hong, J., et al., "Derivation and Characterization of Embryonic Stem Cells Lines Derived from Transgenic Fischer 344 and Dark Agouti Rats," Stem Cells Dev., 21(9):1571-1586 (2012).
Paris, D. B. B. P. and Stout, T. A. E., "Equine embryos and embryonic stem cells: Defining reliable markers of pluripotency," Theriogenology, 74:516-524 (2010).
Patil, V. M., et al., "Transgenic animals and drug development: A review," Indian Journal of Public Health Research & Development, 2(1):106-109 (2011).
Ramirez, C. L., et al., "Unexpected failure rates for modular assembly of engineered zinc fingers," Nat Methods, 5(5):374-375 (2008).
Selsby, J. T., et al., "Porcine Models of Muscular Dystrophy," ILAR J., 56(1):116-126 (2015).
Willinger, T., et al., "Improving human hemato-lymphoid-system mice by cytokine knock-in gene replacement," Trends Immunol., 32(7):321-327 (2011).
U.S. Appl. No. 10/502,565, 371 (c) dated Jul. 22, 2004, Carroll et al.
U.S. Appl. No. 10/912,932, filed Aug. 6, 2004, Urnov et al.
U.S. Appl. No. 13/319,851, 371(c) dated Jan. 30, 2012, Yoneyama et al.
U.S. Appl. No. 14/427,355, 371(c) dated Mar. 11, 2015, Jishage et al.

* cited by examiner

A

B

SEQUENCE LISTING

<160> NUMBER OF SEQ ID NOS: 52

<210> SEQ ID NO 1
<211> LENGTH: 34
<212> TYPE: DNA
<213> ORGANISM: Artificial
<220> FEATURE:
<223> OTHER INFORMATION: an artificially synthesized sequence

<400> SEQUENCE: 1
ataacttcgt atagcataca ttatacgaag ttat                          34

<210> SEQ ID NO 2
<211> LENGTH: 32
<212> TYPE: DNA
<213> ORGANISM: Artificial
<220> FEATURE:
<223> OTHER INFORMATION: an artificially synthesized sequence

<400> SEQUENCE: 2
taactttaaa taattggcat tatttaaagt ta                            32

<210> SEQ ID NO 3
<211> LENGTH: 34
<212> TYPE: DNA
<213> ORGANISM: Artificial
<220> FEATURE:
<223> OTHER INFORMATION: an artificially synthesized sequence

<400> SEQUENCE: 3
gaagttccta ttctctagaa agtataggaa cttc                          34

<210> SEQ ID NO 4
<211> LENGTH: 546
<212> TYPE: DNA
<213> ORGANISM: Homo sapiens
<220> FEATURE:
<221> NAME/KEY: CDS
<222> LOCATION: (1)..(546)

<400> SEQUENCE: 4

```
atg gaa cag ggg aag ggc ctg gct gtc ctc atc ctg gct atc att ctt      48
Met Glu Gln Gly Lys Gly Leu Ala Val Leu Ile Leu Ala Ile Ile Leu
1               5                   10                  15 ctt caa ggt act ttg gcc cag tca atc aaa gga aac cac ttg gtt aag      96
Leu Gln Gly Thr Leu Ala Gln Ser Ile Lys Gly Asn His Leu Val Lys
            20                  25                  30 gtg tat gac tat caa gaa gat ggt tcg gta ctt ctg act tgt gat gca    144
Val Tyr Asp Tyr Gln Glu Asp Gly Ser Val Leu Leu Thr Cys Asp Ala
        35                  40                  45 gaa gcc aaa aat atc aca tgg ttt aaa gat ggg aag atg atc ggc ttc    192
Glu Ala Lys Asn Ile Thr Trp Phe Lys Asp Gly Lys Met Ile Gly Phe
    50                  55                  60 cta act gaa gat aaa aaa aaa tgg aat ctg gga agt aat gcc aag gac    240
Leu Thr Glu Asp Lys Lys Lys Trp Asn Leu Gly Ser Asn Ala Lys Asp
65                  70                  75                  80 cct cga ggg atg tat cag tgt aaa gga tca cag aac aag tca aaa cca    288
Pro Arg Gly Met Tyr Gln Cys Lys Gly Ser Gln Asn Lys Ser Lys Pro
                85                  90                  95 ctc caa gtg tat tac aga atg tgt cag aac tgc att gaa cta aat gca    336
Leu Gln Val Tyr Tyr Arg Met Cys Gln Asn Cys Ile Glu Leu Asn Ala
            100                 105                 110 gcc acc ata tct ggc ttt ctc ttt gct gaa atc gtc agc att ttc gtc    384
Ala Thr Ile Ser Gly Phe Leu Phe Ala Glu Ile Val Ser Ile Phe Val
```

```
ctt gct gtt ggg gtc tac ttc att gct gga cag gat gga gtt cgc cag      432
Leu Ala Val Gly Val Tyr Phe Ile Ala Gly Gln Asp Gly Val Arg Gln
            130                 135                 140 tcg aga gct tca gac aag cag act ctg ttg ccc aat gac cag ctc tac      480
Ser Arg Ala Ser Asp Lys Gln Thr Leu Leu Pro Asn Asp Gln Leu Tyr
145                 150                 155                 160 cag ccc ctc aag gat cga gaa gat gac cag tac agc cac ctt caa gga      528
Gln Pro Leu Lys Asp Arg Glu Asp Asp Gln Tyr Ser His Leu Gln Gly
                165                 170                 175 aac cag ttg agg agg aat                                              546
Asn Gln Leu Arg Arg Asn
            180

<210> SEQ ID NO 5
<211> LENGTH: 182
<212> TYPE: PRT
<213> ORGANISM: Homo sapiens

<400> SEQUENCE: 5

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 6
<211> LENGTH: 513
<212> TYPE: DNA
<213> ORGANISM: Homo sapiens
<220> FEATURE:
<221> NAME/KEY: CDS
<222> LOCATION: (1)..(513)

<400> SEQUENCE: 6 atg gaa cat agc acg ttt ctc tct ggc ctg gta ctg gct acc ctt ctc      48
Met Glu His Ser Thr Phe Leu Ser Gly Leu Val Leu Ala Thr Leu Leu
1               5                   10                  15 tcg caa gtg agc ccc ttc aag ata cct ata gag gaa ctt gag gac aga      96
Ser Gln Val Ser Pro Phe Lys Ile Pro Ile Glu Glu Leu Glu Asp Arg
```

```
                      20                  25                  30
gtg ttt gtg aat tgc aat acc agc atc aca tgg gta gag gga acg gtg      144
Val Phe Val Asn Cys Asn Thr Ser Ile Thr Trp Val Glu Gly Thr Val
         35                  40                  45 gga aca ctg ctc tca gac att aca aga ctg gac ctg gga aaa cgc atc      192
Gly Thr Leu Leu Ser Asp Ile Thr Arg Leu Asp Leu Gly Lys Arg Ile
 50                  55                  60 ctg gac cca cga gga ata tat agg tgt aat ggg aca gat ata tac aag      240
Leu Asp Pro Arg Gly Ile Tyr Arg Cys Asn Gly Thr Asp Ile Tyr Lys
 65                  70                  75                  80 gac aaa gaa tct acc gtg caa gtt cat tat cga atg tgc cag agc tgt      288
Asp Lys Glu Ser Thr Val Gln Val His Tyr Arg Met Cys Gln Ser Cys
                 85                  90                  95 gtg gag ctg gat cca gcc acc gtg gct ggc atc att gtc act gat gtc      336
Val Glu Leu Asp Pro Ala Thr Val Ala Gly Ile Ile Val Thr Asp Val
            100                 105                 110 att gcc act ctg ctc ctt gct ttg gga gtc ttc tgc ttt gct gga cat      384
Ile Ala Thr Leu Leu Leu Ala Leu Gly Val Phe Cys Phe Ala Gly His
        115                 120                 125 gag act gga agg ctg tct ggg gct gcc gac aca caa gct ctg ttg agg      432
Glu Thr Gly Arg Leu Ser Gly Ala Ala Asp Thr Gln Ala Leu Leu Arg
130                 135                 140 aat gac cag gtc tat cag ccc ctc cga gat cga gat gat gct cag tac      480
Asn Asp Gln Val Tyr Gln Pro Leu Arg Asp Arg Asp Asp Ala Gln Tyr
145                 150                 155                 160 agc cac ctt gga gga aac tgg gct cgg aac aag                          513
Ser His Leu Gly Gly Asn Trp Ala Arg Asn Lys
                165                 170

<210> SEQ ID NO 7
<211> LENGTH: 171
<212> TYPE: PRT
<213> ORGANISM: Homo sapiens

<400> SEQUENCE: 7

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
         35                  40                  45

Gly Thr Leu Leu Ser Asp Ile Thr Arg Leu Asp Leu Gly Lys Arg Ile
 50                  55                  60

Leu Asp Pro Arg Gly Ile Tyr Arg Cys Asn Gly Thr Asp Ile Tyr Lys
 65                  70                  75                  80

Asp Lys Glu Ser Thr Val Gln Val His Tyr Arg Met Cys Gln Ser Cys
                 85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 8
<211> LENGTH: 621
<212> TYPE: DNA
<213> ORGANISM: Homo sapiens
<220> FEATURE:
<221> NAME/KEY: CDS
<222> LOCATION: (1)..(621)

<400> SEQUENCE: 8

```
atg cag tcg ggc act cac tgg aga gtt ctg ggc ctc tgc ctc tta tca      48
Met Gln Ser Gly Thr His Trp Arg Val Leu Gly Leu Cys Leu Leu Ser
1               5                   10                  15 gtt ggc gtt tgg ggg caa gat ggt aat gaa gaa atg ggt ggt att aca      96
Val Gly Val Trp Gly Gln Asp Gly Asn Glu Glu Met Gly Gly Ile Thr
            20                  25                  30 cag aca cca tat aaa gtc tcc atc tct gga acc aca gta ata ttg aca     144
Gln Thr Pro Tyr Lys Val Ser Ile Ser Gly Thr Thr Val Ile Leu Thr
        35                  40                  45 tgc cct cag tat cct gga tct gaa ata cta tgg caa cac aat gat aaa     192
Cys Pro Gln Tyr Pro Gly Ser Glu Ile Leu Trp Gln His Asn Asp Lys
    50                  55                  60 aac ata ggc ggt gat gag gat gat aaa aac ata ggc agt gat gag gat     240
Asn Ile Gly Gly Asp Glu Asp Asp Lys Asn Ile Gly Ser Asp Glu Asp
65                  70                  75                  80 cac ctg tca ctg aag gaa ttt tca gaa ttg gag caa agt ggt tat tat     288
His Leu Ser Leu Lys Glu Phe Ser Glu Leu Glu Gln Ser Gly Tyr Tyr
                85                  90                  95 gtc tgc tac ccc aga gga agc aaa cca gaa gat gcg aac ttt tat ctc     336
Val Cys Tyr Pro Arg Gly Ser Lys Pro Glu Asp Ala Asn Phe Tyr Leu
            100                 105                 110 tac ctg agg gca aga gtg tgt gag aac tgc atg gag atg gat gtg atg     384
Tyr Leu Arg Ala Arg Val Cys Glu Asn Cys Met Glu Met Asp Val Met
        115                 120                 125 tcg gtg gcc aca att gtc ata gtg gac atc tgc atc act ggg ggc ttg     432
Ser Val Ala Thr Ile Val Ile Val Asp Ile Cys Ile Thr Gly Gly Leu
    130                 135                 140 ctg ctg ctg gtt tac tac tgg agc aag aat aga aag gcc aag gcc aag     480
Leu Leu Leu Val Tyr Tyr Trp Ser Lys Asn Arg Lys Ala Lys Ala Lys
145                 150                 155                 160 cct gtg aca cga gga gcg ggt gct ggc ggc agg caa agg gga caa aac     528
Pro Val Thr Arg Gly Ala Gly Ala Gly Gly Arg Gln Arg Gly Gln Asn
                165                 170                 175 aag gag agg cca cca cct gtt ccc aac cca gac tat gag ccc atc cgg     576
Lys Glu Arg Pro Pro Pro Val Pro Asn Pro Asp Tyr Glu Pro Ile Arg
            180                 185                 190 aaa ggc cag cgg gac ctg tat tct ggc ctg aat cag aga cgc atc         621
Lys Gly Gln Arg Asp Leu Tyr Ser Gly Leu Asn Gln Arg Arg Ile
        195                 200                 205
```

<210> SEQ ID NO 9
<211> LENGTH: 207
<212> TYPE: PRT
<213> ORGANISM: Homo sapiens

<400> SEQUENCE: 9

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45
```

```
Cys Pro Gln Tyr Pro Gly Ser Glu Ile Leu Trp Gln His Asn Asp Lys
         50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Ile
        195                 200                 205

<210> SEQ ID NO 10
<211> LENGTH: 4
<212> TYPE: PRT
<213> ORGANISM: Artificial
<220> FEATURE:
<223> OTHER INFORMATION: an artificially synthesized sequence

<400> SEQUENCE: 10

Gly Gly Gly Ser
1

<210> SEQ ID NO 11
<211> LENGTH: 4
<212> TYPE: PRT
<213> ORGANISM: Artificial
<220> FEATURE:
<223> OTHER INFORMATION: an artificially synthesized sequence

<400> SEQUENCE: 11

Ser Gly Gly Gly
1

<210> SEQ ID NO 12
<211> LENGTH: 5
<212> TYPE: PRT
<213> ORGANISM: Artificial
<220> FEATURE:
<223> OTHER INFORMATION: an artificially synthesized sequence

<400> SEQUENCE: 12

Gly Gly Gly Gly Ser
1               5

<210> SEQ ID NO 13
<211> LENGTH: 5
<212> TYPE: PRT
<213> ORGANISM: Artificial
<220> FEATURE:
<223> OTHER INFORMATION: an artificially synthesized sequence

<400> SEQUENCE: 13
```

Ser Gly Gly Gly Gly
1               5

<210> SEQ ID NO 14
<211> LENGTH: 6
<212> TYPE: PRT
<213> ORGANISM: Artificial
<220> FEATURE:
<223> OTHER INFORMATION: an artificially synthesized sequence

<400> SEQUENCE: 14

Gly Gly Gly Gly Gly Ser
1               5

<210> SEQ ID NO 15
<211> LENGTH: 6
<212> TYPE: PRT
<213> ORGANISM: Artificial
<220> FEATURE:
<223> OTHER INFORMATION: an artificially synthesized sequence

<400> SEQUENCE: 15

Ser Gly Gly Gly Gly Gly
1               5

<210> SEQ ID NO 16
<211> LENGTH: 7
<212> TYPE: PRT
<213> ORGANISM: Artificial
<220> FEATURE:
<223> OTHER INFORMATION: an artificially synthesized sequence

<400> SEQUENCE: 16

Gly Gly Gly Gly Gly Gly Ser
1               5

<210> SEQ ID NO 17
<211> LENGTH: 7
<212> TYPE: PRT
<213> ORGANISM: Artificial
<220> FEATURE:
<223> OTHER INFORMATION: an artificially synthesized sequence

<400> SEQUENCE: 17

Ser Gly Gly Gly Gly Gly Gly
1               5

<210> SEQ ID NO 18
<211> LENGTH: 20
<212> TYPE: DNA
<213> ORGANISM: Artificial
<220> FEATURE:
<223> OTHER INFORMATION: an artificially synthesized sequence

<400> SEQUENCE: 18
tatcagagct tggttgacgg                                           20

<210> SEQ ID NO 19
<211> LENGTH: 32
<212> TYPE: DNA
<213> ORGANISM: Artificial
<220> FEATURE:
<223> OTHER INFORMATION: an artificially synthesized sequence

<400> SEQUENCE: 19
actcgttgtg gcttagaagc agtaacaata cc                             32

<210> SEQ ID NO 20
<211> LENGTH: 30
<212> TYPE: DNA
<213> ORGANISM: Artificial
<220> FEATURE:
<223> OTHER INFORMATION: an artificially synthesized sequence

<400> SEQUENCE: 20
actgtaatcc tagtacttag gaggctgagg                                    30

<210> SEQ ID NO 21
<211> LENGTH: 26
<212> TYPE: DNA
<213> ORGANISM: Artificial
<220> FEATURE:
<223> OTHER INFORMATION: an artificially synthesized sequence

<400> SEQUENCE: 21
aatccatctt gttcaatggc cgatcc                                        26

<210> SEQ ID NO 22
<211> LENGTH: 30
<212> TYPE: DNA
<213> ORGANISM: Artificial
<220> FEATURE:
<223> OTHER INFORMATION: an artificially synthesized sequence

<400> SEQUENCE: 22
tagcagcctt cagatgaaga ggtaggactc                                    30

<210> SEQ ID NO 23
<211> LENGTH: 28
<212> TYPE: DNA
<213> ORGANISM: Artificial
<220> FEATURE:
<223> OTHER INFORMATION: an artificially synthesized sequence

<400> SEQUENCE: 23
ttgatgtgcc acctcactgc tgcactgg                                      28

<210> SEQ ID NO 24
<211> LENGTH: 24
<212> TYPE: DNA
<213> ORGANISM: Artificial
<220> FEATURE:
<223> OTHER INFORMATION: an artificially synthesized sequence

<400> SEQUENCE: 24
aactgacaat gggacatcag ctga                                          24

<210> SEQ ID NO 25
<211> LENGTH: 24
<212> TYPE: DNA
<213> ORGANISM: Artificial
<220> FEATURE:
<223> OTHER INFORMATION: an artificially synthesized sequence

<400> SEQUENCE: 25
atgggactgt tactttacta agat                                          24

<210> SEQ ID NO 26
<211> LENGTH: 28
<212> TYPE: DNA
<213> ORGANISM: Artificial
<220> FEATURE:

```
<223> OTHER INFORMATION: an artificially synthesized sequence

<400> SEQUENCE: 26
aagaaatggg tggtattaca cagacacc                                              28

<210> SEQ ID NO 27
<211> LENGTH: 31
<212> TYPE: DNA
<213> ORGANISM: Artificial
<220> FEATURE:
<223> OTHER INFORMATION: an artificially synthesized sequence

<400> SEQUENCE: 27
tgggccagcg ggaggcagtg ttctccagag g                                          31

<210> SEQ ID NO 28
<211> LENGTH: 29
<212> TYPE: DNA
<213> ORGANISM: Artificial
<220> FEATURE:
<223> OTHER INFORMATION: an artificially synthesized sequence

<400> SEQUENCE: 28
tagttcggtg acctggcttt atctactgg                                             29

<210> SEQ ID NO 29
<211> LENGTH: 31
<212> TYPE: DNA
<213> ORGANISM: Artificial
<220> FEATURE:
<223> OTHER INFORMATION: an artificially synthesized sequence

<400> SEQUENCE: 29
atggctgctt ctagaagcca ccagtctcag g                                          31

<210> SEQ ID NO 30
<211> LENGTH: 26
<212> TYPE: DNA
<213> ORGANISM: Artificial
<220> FEATURE:
<223> OTHER INFORMATION: an artificially synthesized sequence

<400> SEQUENCE: 30
tgctccacgc ttttgccgga ggacag                                                26

<210> SEQ ID NO 31
<211> LENGTH: 25
<212> TYPE: DNA
<213> ORGANISM: Artificial
<220> FEATURE:
<223> OTHER INFORMATION: an artificially synthesized sequence

<400> SEQUENCE: 31
taggaggaga acacctggac tactc                                                 25

<210> SEQ ID NO 32
<211> LENGTH: 28
<212> TYPE: DNA
<213> ORGANISM: Artificial
<220> FEATURE:
<223> OTHER INFORMATION: an artificially synthesized sequence

<400> SEQUENCE: 32
agcattctga gaggatgcgg tggaacac                                              28
```

```
<210> SEQ ID NO 33
<211> LENGTH: 29
<212> TYPE: DNA
<213> ORGANISM: Artificial
<220> FEATURE:
<223> OTHER INFORMATION: an artificially synthesized sequence

<400> SEQUENCE: 33
tgctcggagg gctggatctg ggtccacag                              29

<210> SEQ ID NO 34
<211> LENGTH: 29
<212> TYPE: DNA
<213> ORGANISM: Artificial
<220> FEATURE:
<223> OTHER INFORMATION: an artificially synthesized sequence

<400> SEQUENCE: 34
tcatcctgtg gcttgcctct atttgttgc                              29

<210> SEQ ID NO 35
<211> LENGTH: 29
<212> TYPE: DNA
<213> ORGANISM: Artificial
<220> FEATURE:
<223> OTHER INFORMATION: an artificially synthesized sequence

<400> SEQUENCE: 35
ttgctatggc actttgagaa acctccatc                              29

<210> SEQ ID NO 36
<211> LENGTH: 26
<212> TYPE: DNA
<213> ORGANISM: Artificial
<220> FEATURE:
<223> OTHER INFORMATION: an artificially synthesized sequence

<400> SEQUENCE: 36
aatacttcta ctggagaagc aaagag                                 26

<210> SEQ ID NO 37
<211> LENGTH: 27
<212> TYPE: DNA
<213> ORGANISM: Artificial
<220> FEATURE:
<223> OTHER INFORMATION: an artificially synthesized sequence

<400> SEQUENCE: 37
tagttgcatt tagaggactt attatgc                                27

<210> SEQ ID NO 38
<211> LENGTH: 360
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(360)

<400> SEQUENCE: 38 gaa gtg cag ctg gtc gag agc ggg ggg ggg ctg gtg cag cca gga gga    48
Glu Val Gln Leu Val Glu Ser Gly Gly Gly Leu Val Gln Pro Gly Gly
1               5                   10                  15 tct ctg agg ctg agt tgc gcc gct tca ggc ttc aac atc aag gac act    96
Ser Leu Arg Leu Ser Cys Ala Ala Ser Gly Phe Asn Ile Lys Asp Thr
            20                  25                  30
```

```
tac att cac tgg gtg cga cag gca cca ggg aaa gga ctg gag tgg gtc        144
Tyr Ile His Trp Val Arg Gln Ala Pro Gly Lys Gly Leu Glu Trp Val
        35                  40                  45 gcc cgg atc tat ccc aca aat gga tac act cgg tat gcc gac tcc gtg        192
Ala Arg Ile Tyr Pro Thr Asn Gly Tyr Thr Arg Tyr Ala Asp Ser Val
 50                  55                  60 aag ggc aga ttc acc att agc gcc gat acc tcc aaa aac aca gct tac        240
Lys Gly Arg Phe Thr Ile Ser Ala Asp Thr Ser Lys Asn Thr Ala Tyr
65                  70                  75                  80 ctg cag atg aac agc ctg agg gct gaa gat aca gca gtg tac tat tgc        288
Leu Gln Met Asn Ser Leu Arg Ala Glu Asp Thr Ala Val Tyr Tyr Cys
                85                  90                  95 tct cgc tgg gga ggc gac ggc ttt tac gca atg gat tat tgg ggc cag        336
Ser Arg Trp Gly Gly Asp Gly Phe Tyr Ala Met Asp Tyr Trp Gly Gln
            100                 105                 110 ggg act ctg gtg acc gtc agc tcc                                        360
Gly Thr Leu Val Thr Val Ser Ser
        115                 120
```

<210> SEQ ID NO 39
<211> LENGTH: 120
<212> TYPE: PRT
<213> ORGANISM: Artificial
<220> FEATURE:
<223> OTHER INFORMATION: Synthetic Construct

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
 50                 55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 40
<211> LENGTH: 321
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(321)

<400> SEQUENCE: 40

```
gac att cag atg act cag agc cct tca agc ctg agt gct tca gtc ggg         48
Asp Ile Gln Met Thr Gln Ser Pro Ser Ser Leu Ser Ala Ser Val Gly
1               5                   10                  15 gac agg gtg aca atc act tgc cgc gca agc cag gat gtc aac acc gct         96
Asp Arg Val Thr Ile Thr Cys Arg Ala Ser Gln Asp Val Asn Thr Ala
            20                  25                  30
```

```
gtg gca tgg tac cag cag aag cca ggc aaa gca ccc aag ctg ctg atc     144
Val Ala Trp Tyr Gln Gln Lys Pro Gly Lys Ala Pro Lys Leu Leu Ile
        35                  40                  45 tac agc gcc tcc ttc ctg tat tcc ggg gtg cca tct cgg ttt tct ggc     192
Tyr Ser Ala Ser Phe Leu Tyr Ser Gly Val Pro Ser Arg Phe Ser Gly
 50                  55                  60 agt aga tca ggg acc gac ttc acc ctg aca atc agc tcc ctg cag ccc     240
Ser Arg Ser Gly Thr Asp Phe Thr Leu Thr Ile Ser Ser Leu Gln Pro
 65                  70                  75                  80 gaa gat ttt gcc aca tac tat tgc cag cag cac tac acc aca ccc cct     288
Glu Asp Phe Ala Thr Tyr Tyr Cys Gln Gln His Tyr Thr Thr Pro Pro
                 85                  90                  95 aca ttc ggg cag gga act aaa gtg gag att aag                         321
Thr Phe Gly Gln Gly Thr Lys Val Glu Ile Lys
            100                 105

<210> SEQ ID NO 41
<211> LENGTH: 107
<212> TYPE: PRT
<213> ORGANISM: Artificial
<220> FEATURE:
<223> OTHER INFORMATION: Synthetic Construct

<400> SEQUENCE: 41

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 42
<211> LENGTH: 321
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(321)

<400> SEQUENCE: 42 gat att cag atg act cag agc cct tct tca ctg agt gca tca gtg ggc      48
Asp Ile Gln Met Thr Gln Ser Pro Ser Ser Leu Ser Ala Ser Val Gly
 1               5                   10                  15 gac cga gtc acc atc aca tgc cgg gcc agc cag gat att aga aac tac      96
Asp Arg Val Thr Ile Thr Cys Arg Ala Ser Gln Asp Ile Arg Asn Tyr
             20                  25                  30 ctg aat tgg tat cag cag aag cct ggc aaa gct cca aag ctg ctg atc     144
Leu Asn Trp Tyr Gln Gln Lys Pro Gly Lys Ala Pro Lys Leu Leu Ile
         35                  40                  45 tac tat acc tct agg ctg gag agt gga gtg cca tca cgc ttc agc gga     192
Tyr Tyr Thr Ser Arg Leu Glu Ser Gly Val Pro Ser Arg Phe Ser Gly
```

```
tcc gga tct ggg acc gac tac act ctg acc att agc tcc ctg cag cca    240
Ser Gly Ser Gly Thr Asp Tyr Thr Leu Thr Ile Ser Ser Leu Gln Pro
 65              70                  75                  80 gaa gat ttc gcc aca tac tat tgt cag cag gga aac act ctg ccc tgg    288
Glu Asp Phe Ala Thr Tyr Tyr Cys Gln Gln Gly Asn Thr Leu Pro Trp
                 85                  90                  95 acc ttt gga cag ggc acc aaa gtg gag atc aag                        321
Thr Phe Gly Gln Gly Thr Lys Val Glu Ile Lys
            100                 105
```

<210> SEQ ID NO 43
<211> LENGTH: 107
<212> TYPE: PRT
<213> ORGANISM: Artificial
<220> FEATURE:
<223> OTHER INFORMATION: Synthetic Construct

<400> SEQUENCE: 43

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
         35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65              70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys
            100                 105
```

<210> SEQ ID NO 44
<211> LENGTH: 366
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(366)

<400> SEQUENCE: 44

```
gag gtg cag ctg gtc gaa tcc gga gga gga ctg gtg cag cca gga gga     48
Glu Val Gln Leu Val Glu Ser Gly Gly Gly Leu Val Gln Pro Gly Gly
 1               5                  10                  15 agc ctg cga ctg tcc tgc gcc gct agc gga tac tcc ttt aca ggc tat     96
Ser Leu Arg Leu Ser Cys Ala Ala Ser Gly Tyr Ser Phe Thr Gly Tyr
            20                  25                  30 act atg aat tgg gtg cga cag gct ccc ggg aaa gga ctg gag tgg gtg    144
Thr Met Asn Trp Val Arg Gln Ala Pro Gly Lys Gly Leu Glu Trp Val
         35                  40                  45 gca ctg atc aac cct tac aag ggc gtc agt acc tat aat cag aag ttc    192
Ala Leu Ile Asn Pro Tyr Lys Gly Val Ser Thr Tyr Asn Gln Lys Phe
 50                  55                  60 aaa gac cgg ttc acc att tct gtg gat aag agt aaa aac acc gct tac    240
Lys Asp Arg Phe Thr Ile Ser Val Asp Lys Ser Lys Asn Thr Ala Tyr
 65              70                  75                  80 ctg cag atg aat agc ctg aga gca gag gac aca gcc gtg tac tat tgc    288
```

```
Leu Gln Met Asn Ser Leu Arg Ala Glu Asp Thr Ala Val Tyr Tyr Cys
                85                  90                  95 gca agg agt ggc tac tat ggg gac tca gat tgg tat ttc gac gtg tgg        336
Ala Arg Ser Gly Tyr Tyr Gly Asp Ser Asp Trp Tyr Phe Asp Val Trp
            100                 105                 110 gga cag ggg acc ctg gtg aca gtc tct agt                                366
Gly Gln Gly Thr Leu Val Thr Val Ser Ser
        115                 120
```

<210> SEQ ID NO 45
<211> LENGTH: 122
<212> TYPE: PRT
<213> ORGANISM: Artificial
<220> FEATURE:
<223> OTHER INFORMATION: Synthetic Construct

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120
```

<210> SEQ ID NO 46
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 46

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115
```

<210> SEQ ID NO 47
<211> LENGTH: 108
<212> TYPE: PRT
<213> ORGANISM: Artificial Sequence
<220> FEATURE:
<223> OTHER INFORMATION: an artificially synthesized sequence

<400> SEQUENCE: 47

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 48
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 48

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205
```

Ile Glu Lys Thr Ile Ser Lys Thr Lys Gly Arg Pro Lys Ala Pro Gln
            210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Glu Leu Asn
            275                 280                 285

Val Gln Lys Ser Asn Trp Glu Ala Gly Asn Thr Phe Thr Cys Ser Val
            290                 295                 300

Leu His Glu Gly Leu His Asn His His Thr Glu Lys Ser Leu Ser His
305                 310                 315                 320

Ser Pro Gly Lys

<210> SEQ ID NO 49
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 49

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 50
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 50

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
            85                  90                  95

Tyr Cys Arg Tyr Val His Tyr Ala Ala Gly Tyr Gly Val Asp Ile Trp
           100                 105                 110

Gly Gln Gly Thr Thr Val Thr Val Ser Ser
           115                 120

<210> SEQ ID NO 51
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 51

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly
                85                  90                  95

Thr Gln Val Pro Tyr Thr Phe Gly Gln Gly Thr Lys Leu Glu Ile Lys
            100                 105                 110

<210> SEQ ID NO 52
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 52

Ala Lys Thr Thr Pro Pro Ser Val Tyr Pro Leu Ala Pro Gly Ser Ala
1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu

```
          145                 150                 155                 160
Val His Thr Ala Gln Thr Gln Pro Arg Glu Glu Gln Phe Asn Ser Thr
                    165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
            210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Arg Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys
```

NON-HUMAN ANIMAL HAVING HUMAN CD3 GENE SUBSTITUTED FOR ENDOGENOUS CD3 GENE

CROSS-REFERENCE TO RELATED APPLICATIONS

This application is a U.S. National Phase of PCT Application No. PCT/JP2016/070276, filed Jul. 8, 2016, which claims the benefit of Japanese Patent Application No. 2015-139023, filed Jul. 10, 2015, and Japanese Patent Application No. 2016-049919, filed Mar. 14, 2016, each of which is incorporated herein by reference in its entirety.

REFERENCE TO SEQUENCE LISTING SUBMITTED ELECTRONICALLY:

The content of the electronically submitted sequence listing (Name: 6663_0053_Sequence_Listing.txt; Size: 42,657 bytes; and Date of Creation: Jan. 2, 2018) filed with the application is incorporated herein by reference in its entirety.

TECHNICAL FIELD

The present invention relates to human CD3 gene-substituted non-human animals, and methods for evaluating compounds using the human CD3 gene-substituted non-human animals, and such.

BACKGROUND ART

A T-cell receptor (TCR) complex is an antigen-receptor molecule expressed mainly on T cells. It is composed of antigen-binding TCRα and β chains (or δ and γ chains), and multiple CD3 molecules (CD3-epsilon (ε), CD3-delta (δ), and CD3-gamma (γ)) and CD247 that mainly have a function of transducing signals into cells.

TCRα and TCRβ are formed from variable and constant regions. Through V(D)J gene rearrangement similarly to antibody molecules, the variable regions constitute a repertoire that presents binding activities to various antigen molecules that differ for every cell clone. T cells are activated through specific binding via TCR complexes to antigen molecules presented by major histocompatibility complexes (MHCs) on the cell surface of dendritic cells and macrophages. However, a domain for transducing signals into cells is not carried by either TCR α or β chain, but carried by each of the CD3 molecules (CD3ε, CD3δ, and CD3γ) and CD247 that form the TCR complex. Among them, CD3ε forms a dimer with CD3δ or CD3γ, CD247 forms a homodimer, and then these dimers further form a complex with the TCRα chain and the TCRβ chain to thereby constitute a functional TCR complex. CD3 complexes (εγ and δε) and CD247 homodimer carry an immunoreceptor tyrosine-based activation motif (ITAM) in their intracellular domain, and this ITAM is involved in transducing activation signals into cells.

Among Cd3ε, Cd3δ, and Cd3γ, Cd3ε is known as a molecule that plays a necessary and essential role in TCR complex formation since Cd3ε gene-deficient mice cannot form a normal TCR complex. More specifically, in Cd3ε gene-deficient mice, TCRα rearrangement and expression onto the cell surface following TCRβ rearrangement do not take place, and TCR complexes are not expressed in the process of T cell differentiation in the thymus. Therefore, proliferation and differentiation do not occur during and after Double Negative (DN) 3-4 of the stages of differentiation into mature T cells. As a result, Cd3ε gene-deficient mice lack mature T cells (Non-patent Documents 1, 2, and 3).

Furthermore, Cd3ε has been suggested to be the most important molecule in T cell activation. More specifically, it is known that when a TCR binds to a ligand such as an antigen presented by an MHC, the conformation of the intracellular domain of Cd3ε changes, which induces recruitment of Src family tyrosine kinases such as Lck and Fyn, and subsequently activates downstream signal transduction molecules such as Src Homology 2 Domain-containing ζ-chain-associated protein (ZAP-70) (Non-patent Documents 4 and 5). Furthermore, interaction with an anti-CD3 antibody having agonistic activity can result in activation similar to that caused by antigen-presenting cells, and a large number of studies are being conducted regarding application of immune cell therapy to cancer treatment, including stimulation of T-cell activity using anti-CD3 agonist antibodies.

However, therapeutic antibodies having an additional function to activate T cells as mentioned above are difficult to evaluate through animal tests in preclinical studies. This is because the sequence homologies of the extracellular regions of CD3ε, CD3δ, and CD3γ are low among species, and antibodies for humans are predicted not to bind to CD3 molecules of nonprimate animals.

Therefore, to evaluate the above-mentioned therapeutic antibodies and therapeutic compounds, attempts have been made to produce laboratory animals carrying human T cells by reconstituting human-derived hematopoietic stem cells, or to produce laboratory animals whose CD3 molecules have been humanized.

First, as such model animals, those produced by transplanting human-derived hemoatopoietic stem cells into immunodeficient mice such as severe combined immunodeficiency (scid) mice are being used. Hematocytes derived from the grafted hematopoietic stem cells, which include T cells, are of human origin. However, in such model animals, since the cytokines, growth factors and microenvironment-forming cells that are necessary for proliferation and differentiation of human hematopoietic stem cells all remain mouse-derived, human hematocyte differentiation is not reproduced completely. It is known that even when human hematopoietic stem cells are transplanted into NOD-scid mice, human T cells do not sufficiently differentiate, and that while T cell differentiation is observed when the transplantation is performed on NOG mice, those T cells are unable to exhibit human leukocyte antigen (HLA)-restricted immune response, and thus it cannot be said that immune cell lines that function completely in the body of mice have been established (Non-patent Document 6). Recently, further improvements have been achieved by humanization of interleukin-3 (IL-3), GM-CSF, and Stem Cell Factor (SCF), but there still remains the problem that T cells are unable to show HLA-restricted immune response (Non-patent Document 7).

Efforts have been made to perform gene transfer of human CD3 molecules into laboratory animals for genetic humanization. As one such example, there has been a report of transgenic mice into which human CD3 molecule ε gene has been introduced (Non-patent Document 8). However, such transgenic mice show marked decrease in the number of thymocytes, and it is difficult to say that they are mice with normal immune function. Furthermore, influence on T cell differentiation depends on the expression level of human CD3ε, and transgenic mouse strains that express it at high levels have been found to lack natural killer (NK) cells.

Furthermore, there is no report on genetically modified mice in which the full lengths of CD3ε, CD3δ, and CD3γ, spanning the extracellular region through the cytoplasmic region, have been humanized. In these humanized mice, the immune system including TCR formation and downstream signaling has not been confirmed to function normally, equivalently to mouse endogenous Cd3ε, Cd3δ, and Cd3γ. Therefore, human CD3-expressing mice carrying normal immunocompetent cells including T cells had not yet existed.

PRIOR ART DOCUMENTS

Non-Patent Documents

[Non-patent Document 1] Malissen et. al. (1995) EMBO. J. 14:4641-4653

[Non-patent Document 2] DeJarnette et. al. (1998) PNAS. 95:14909-14914

[Non-patent Document 3] Wang et. al. (1998) Int. Immunol. 10:1777-1788

[Non-patent Document 4] Bettini et. al. (2014) J. Immunol. 193:258-267

[Non-patent Document 5] Xu et. al. (2008) Cell. 135:702-713

[Non-patent Document 6] Billerbeck et. al. (2011) Blood. 117:3076-3086

[Non-patent Document 7] Rongvaux et. al. (2014) Nat Biotechnol. 32:364-372

[Non-patent Document 8] Wang et. al. (1994) PNAS. 91:9402-9406

SUMMARY OF THE INVENTION

Problems to be Solved by the Invention

The present invention was achieved in view of the above circumstances. An objective of the present invention is to provide genetically modified non-human animals functionally expressing human CD3 gene(s), or more specifically, genetically modified non-human animals carrying immunocompetent cells including T cells that function normally; methods for preparing the genetically modified non-human animals; and methods of screening for therapeutic agents for various diseases, using the genetically modified animals.

Means for Solving the Problems

The present inventors considered that in the above-mentioned human CD3 ε gene-introduced transgenic mice, expression of endogenous mouse Cd3ε remains, and Cd3γ and Cd3δ which are partner molecules in the dimer formation are also mouse-derived molecules, and thus, there may be some abnormalities in the process of TCR complex formation and in the subsequent T cell differentiation process. Therefore, to solve the above-mentioned problem, the inventors attempted to prepare mice that was made deficient in the expression of one or more Cd3 genes selected from the group consisting of endogenous Cd3ε, Cd3γ, and Cd3δ and that was able to functionally express one or more CD3 genes selected from the group consisting of human CD3ε, CD3γ, and CD3δ genes. As a result of dedicated studies, the present inventors prepared mice in which the endogenous gene region(s) mentioned above had been deleted using the Cre-loxP and Dre-Rox systems, and further CD3 gene(s) selected from the group consisting of human CD3ε, CD3γ, and CD3δ had been introduced. In such mice, surprisingly, the number and functions of mature T cells were found to be equivalent to those in normal mice. More specifically, fluorescence activated cell sorting (FACS) analysis of the collected spleen cells using anti-human CD3 antibodies, anti-Cd4 antibodies, and anti-Cd8 antibodies confirmed that expressions of the major T cell differentiation markers were normal. That is, abnormalities in the T cell differentiation process and decrease in the number of T cells were avoided by functionally deleting one or more Cd3 genes selected from the group consisting of endogenous Cd3ε, δ, and γ, and allowing to functionally express CD3 selected from the group consisting of human CD3 ε, δ, and γ. Moreover, since the number of Cd4-positive or Cd8-positive cells among the T cells was equivalent to that in normal mice, the process of differentiation into mature T cells was also confirmed to be normal. Furthermore, it was revealed that immunization of the mice using chicken ovalbumin as a foreign antigen resulted in production of antibodies specific to the foreign antigen at an equivalent level as that in normal mice, and that helper T cells of the mice normally functioned in the process of antibody production against the foreign antigen.

As such, the following findings are beyond expectations: the finding that mouse strains, in which CD3 molecules have been humanized without causing abnormalities in the T cell differentiation and maturation processes while maintaining the T cell function, are able to be established by functionally deleting one or more Cd3 genes selected from the group consisting of mouse endogenous Cd3ε, Cd3δ, and Cd3γ, and by allowing to express CD3s selected from the group consisting of human CD3ε, CD3δ, and CD3γ at a physiologically appropriate level, in the present invention; and the further finding that in mice in which CD3 molecules have been humanized at the cytoplasmic regions as well, the CD3 molecules can function normally as and equivalent to mouse endogenous Cd3 molecules, in the present invention.

Compounds that target CD3 and modulate the interactions with related molecules inside and outside cells are expected to be used as immunomodulatory agents having the effects of activating or inhibiting T cell functions. Considering development of compounds that inhibit the interactions with related molecules inside and outside cells, designing compounds that are highly specific to the extracellular or cytoplasmic regions of human CD3ε, CD3δ, and CD3γ would enable therapeutic compounds to target not only the extracellular regions but also the cytoplasmic regions of human CD3ε, CD3δ, and CD3γ.

Furthermore, when a mouse cancer cell line in which a human cancer antigen gene has been introduced is transplanted into such mice, it is possible to validate the cancer cell proliferation inhibitory effects of antibodies that specifically recognize both the cancer antigen and the human CD3 molecule(s); therefore, by using this evaluation system, therapeutic antibodies having the desired activity can be developed efficiently.

The present invention has been made based on such findings, and in specific embodiments, the invention relates to, for example, the following invention.

[1] a genetically modified non-human animal, wherein the animal is functionally deficient in at least one or more types of CD3 genes selected from the group consisting of endogenous CD3ε, CD3δ, and CD3γ in its genome and functionally expresses at least one or more types of human CD3 genes selected from the group consisting of human CD3ε, CD3δ, and CD3γ;

[2] the genetically modified non-human animal of [1], wherein the animal functionally expresses human CD3 genes comprising human CD3ε, CD3δ, and CD3γ;

[3] the genetically modified non-human animal of [1] or [2], wherein a full-length nucleotide sequence of at least one or more types of human CD3 genes selected from the group consisting of human CD3ε, CD3δ, and CD3γ has been inserted into the genome;

[4] the genetically modified non-human animal of any one of [1] to [3], wherein a non-human animal-derived T cell receptor and human CD3 molecule(s) form a complex on the cell membrane of a T cell carried by the non-human animal;

[5] the genetically modified non-human animal of any one of [1] to [4], the animal further expressing a human immune checkpoint gene, a human cancer-specific antigen gene, and/or a human immune costimulatory molecule gene;

[6] the genetically modified non-human animal of any one of [1] to [5], wherein the non-human animal is a non-human mammal;

[7] the genetically modified non-human animal of [6], wherein the non-human mammal is a mouse;

[8] the genetically modified non-human animal of any one of [1] to [7], which is for screening for a therapeutic agent for malignant neoplastic disease or autoimmune disease;

[9] the genetically modified non-human animal of [8], which is for screening for a therapeutic agent for malignant neoplastic disease, wherein a cancer cell has been transplanted into the non-human animal;

[10] the genetically modified non-human animal of [9], wherein the cancer cell is a cell derived from lung cancer, gastric cancer, liver cancer, esophageal cancer, or ovarian cancer;

[11] the genetically modified non-human animal of [9], wherein the cancer cell is a HER2-positive cell;

[12] a method for producing a genetically modified non-human animal, the method comprising the steps of:
(1) functionally deleting at least one or more types of CD3 genes selected from the group consisting of endogenous CD3ε, CD3δ, and CD3γ in its genome; and
(2) introducing at least one or more types of human CD3 genes selected from the group consisting of human CD3ε, human CD3δ, and human CD3γ into the genome;

[13] the method for producing a genetically modified non-human animal of [12], wherein in step (2), human CD3 genes comprising human CD3ε, CD3δ, and CD3γ are introduced into the genome;

[14] the method for producing a genetically modified non-human animal of [12] or [13], the method further comprising the step of transplanting a cancer cell to the non-human animal;

[15] the method for producing a genetically modified non-human animal of [14], wherein the cancer cell is a cell derived from lung cancer, gastric cancer, liver cancer, esophageal cancer, or ovarian cancer;

[16] the method for producing a genetically modified non-human animal of any one of [12] to [15], the method further comprising the step of introducing a human immune checkpoint gene, a human cancer-specific antigen gene, and/or a human immune costimulatory molecule gene into the genome of the non-human animal;

[17] the method for producing a genetically modified non-human animal of [16], wherein the step of introducing a human immune checkpoint gene, a human cancer-specific antigen gene, and/or a human immune costimulatory molecule gene into the genome is the step of crossing the non-human animal with a non-human animal that is different from the non-human animal and has the respective human immune checkpoint gene, human cancer-specific antigen gene, and/or human immune costimulatory molecule gene introduced into the genome;

[18] a method of screening for a therapeutic agent for malignant neoplastic disease or autoimmune disease, the method comprising the steps of:
(1) contacting a test substance with the genetically modified non-human animal of any one of claims 1 to 10, or an organ, tissue, or cell thereof; and
(2) selecting a candidate test substance using as an indicator drug efficacy and/or toxicity of the test substance in the genetically modified non-human animal individual, or the organ, tissue, or cell thereof;

[19] a method of screening for a therapeutic agent for malignant neoplastic disease, the method comprising the steps of:
(1) administering as a test substance one from a library of antigen-binding molecules comprising a human CD3-binding domain and a cancer-specific antigen-binding domain to a first genetically modified non-human animal of any one of claims 1 to 10;
(2) determining a cell proliferation inhibitory effect and/or pharmacokinetic characteristics of the test substance on a cell expressing the cancer-specific antigen; and
(3) comparing the cell proliferation inhibitory effect and/or pharmacokinetic characteristics of the test substance with the cell proliferation inhibitory effect and/or pharmacokinetic characteristics of a control antibody administered to a second genetically modified non-human animal which is different from the first non-human animal.

Effects of the Invention

In one embodiment, a genetically modified non-human animal of the present invention is functionally deficient in the expression of one or more types of CD3 genes selected from the group consisting of endogenous CD3ε, CD3δ, and CD3γ, and functionally expresses one or more types of human CD3 genes selected from the group consisting of human CD3ε, CD3δ, and CD3γ genes. More specifically, the present invention makes it possible to provide a genetically modified non-human animal expressing human CD3 molecules, whose functions of immunocompetent cells including T cells are normal. In the objective of developing human CD3-mediated antibody drugs, immunostimulators, immune cell therapy, and such, use of genetically modified non-human animals of the present invention allows appropriate evaluation of therapeutic agents and therapeutic methods that are highly specific to human CD3.

BRIEF DESCRIPTION OF THE DRAWINGS

FIG. 3A presents the representative examples of PCR results that detect the deficiency of the mouse Cd3 gene region.

FIG. 11B, See the explanation under FIG. 11A.

FIG. 11C, See the explanation under FIG. 11A.

FIG. 11D, See the explanation under FIG. 11A.

MODE FOR CARRYING OUT THE INVENTION

Figure 1A:
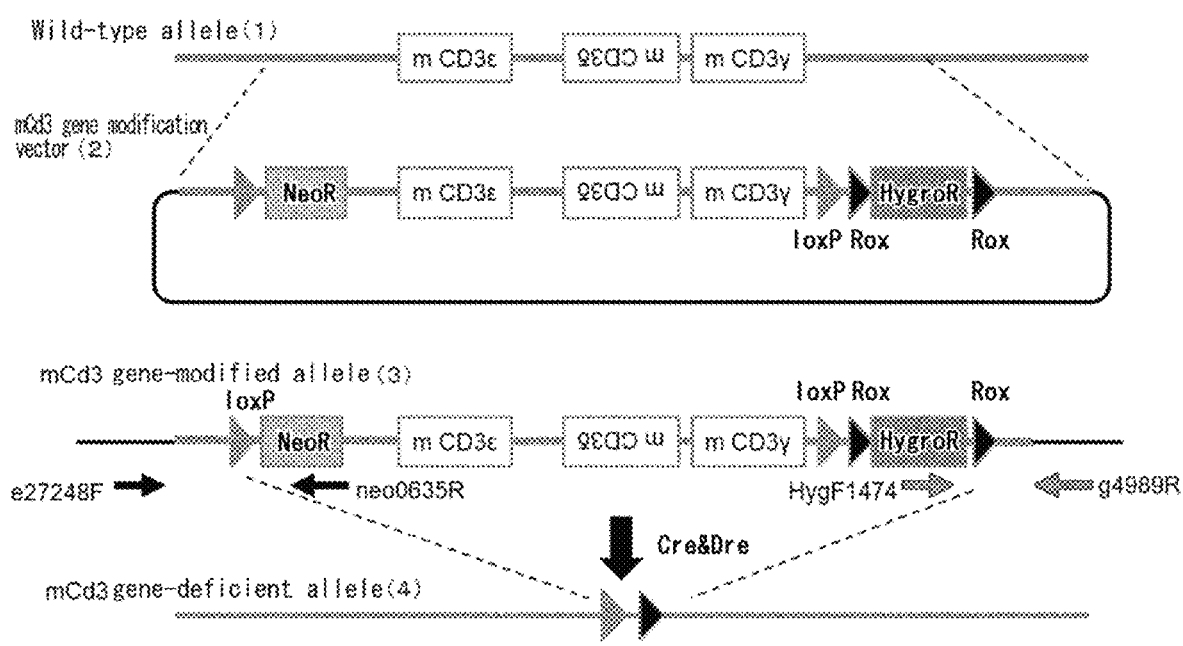
FIG. 1A presents the structure of a genomic DNA containing mouse Cd3ε, Cd3δ, and Cd3γ genes (1), a mouse Cd3 gene modification vector constructed by modifying a bacterial artificial chromosome (BAC) clone containing the whole gene region (2), the structure of a genomic DNA in which loxP and Rox sequences have been inserted at the target position using the above-mentioned vector (3), and the structure of a Cd3ε, Cd3δ, and Cd3γ-gene deficient allele produced by the actions of Cre and Dre recombinases (4).

The present invention relates to a genetically modified non-human animal which is functionally deficient in at least one or more types of CD3 genes selected from the group consisting of endogenous CD3ε, CD3δ, and CD3γ in its genome and functionally expresses at least one or more types of human CD3 genes selected from the group consisting of human CD3ε, CD3δ, and CD3γ.

Generally, regarding the way for describing the gene names, in some biological species, CD3ε, CD3δ, and CD3γ may be written as CD3E, CD3D, and CD3G, respectively; however, the gene names of CD3ε, CD3δ, and CD3γ are used herein independent of the biological species. More specifically, in the present invention, CD3ε includes CD3E and CD3e, CD3δ includes CD3D and CD3d, and CD3γ includes CD3G and CD3g. For example, when denoted herein as "human CD3ε", this refers to a human CD3 epsilon gene, and when denoted as "mouse Cd3ε", this refers to a mouse Cd3 epsilon gene. When denoted herein as "human CD3δ", this refers to a human CD3 delta gene, and when denoted as "mouse Cd3δ", this refers to a mouse Cd3 delta gene. Furthermore, when denoted herein as "human CD3γ", this refers to a human CD3 gamma gene, and when denoted as "mouse Cd3γ", this refers to a mouse Cd3 gamma gene.

In the present invention, the phrase "functionally deficient in an endogenous gene in a genome" is not particularly limited as long as an endogenous target gene (for example, CD3ε, CD3δ, or CD3γ) in a non-human animal genome does not express its function, and may include an embodiment in which an endogenous target gene (for example, CD3ε, CD3δ, or CD3γ) in a non-human animal genome or its protein is not expressed. For example, a targeted gene may be deleted (abolished) in a non-human animal genome using knockout technology based on genome editing techniques such as homologous recombination, CRISPR-Cas (CRISPR/Cas9), zinc finger nucleases, or TALEN, or a method for completely suppressing the expression of a targeted gene by siRNA and such may be used. Furthermore, as long as an endogenous target gene is not expressed, a foreign gene may be inserted at the position of the target gene in the non-human animal genome, for example, using knock-in technology.

In a non-limiting embodiment of the present invention, differentiation into and production of mature T cells is inhibited in an animal which is functionally deficient in at least one or more types of CD3 genes selected from the group consisting of endogenous CD3ε, CD3δ, and CD3γ in its genome, when the animal is not made to express foreign CD3 such as human CD3 gene(s). Herein, mature T cells are, for example, T cells in which either CD4 or CD8 (not both) is positive (referred to as CD4 single positive cells and CD8 single positive cells, respectively). More specifically, in the spleen of an animal which is deficient in at least one or more types of CD3 genes selected from the group consisting of endogenous CD3ε, CD3δ, and CD3γ in its genome, when the animal does not express foreign CD3 such as human CD3 gene(s), a total of CD4 single positive cells and CD8 single positive cells is for example, 70% or less, preferably 60% or less, more preferably 50% or less, 40% or less, 30% or less, 20% or less, 10% or less, 5% or less, 3% or less, or 1% or less compared to the level of a wild type or the level generally regarded as normal. The developmental stage at which the mature T cells are counted may be any stage as long as it is a stage at which mature T cells are produced in the wild type, and preferably the age when an animal typically reaches adulthood (becomes fertile), for example, 8- to 12-weeks old, such as 12-weeks old, for mice.

Furthermore, in a non-limiting embodiment of the present invention, antibody production is inhibited in an animal which is deficient in at least one or more types of CD3 genes selected from the group consisting of endogenous CD3ε, CD3δ, and CD3γ in the genome, when the animal dose not express foreign CD3 such as human CD3 gene(s). Herein, the types of antibodies are not particularly limited, and for example, production of IgG (such as IgG1), and/or production of IgE may be inhibited. Whether antibody production is inhibited can be determined by inoculating a foreign antigen, and observing whether antibodies are produced or measuring the amount of antibodies produced. The foreign antigen is not particularly limited, and antibody production can be confirmed using a desired antigen, for example, chicken ovalbumin (OVA). In an animal which is deficient in at least one or more types of CD3 genes selected from the group consisting of endogenous CD3ε, CD3δ, and CD3γ in the genome when the animal does not express foreign CD3 such as human CD3 gene(s), the antibody titer is for example, 70% or less, preferably 60% or less, more preferably 60% or less, 50% or less, 40% or less, 30% or less, 20% or less, 10% or less, 5% or less, 3% or less, or 1% or less compared to the level of a wild type or the level generally regarded as normal. The developmental stage at which the antibody production is measured may be any stage as long as it is a stage at which antibodies are produced in the wild type, preferably the age when an animal typically reaches adulthood, for example, 8- to 12-weeks old, such as 12-weeks old, for mice.

An embodiment of functionally deleting endogenous gene(s) in a genome in the present invention is exemplified by a method for completely deleting a genomic region comprising one or more types of CD3 genes selected from the group consisting of CD3ε, CD3δ, and CD3γ by inserting a sequence of a substrate for a recombinase that acts sequence-specifically at the 5' side and 3' side of the genomic region encoding one or more types of CD3 genes selected from the group consisting of non-human animal-derived endogenous CD3ε, CD3δ, and CD3γ, and then allowing the recombinase to act. Furthermore, genetically modified non-human animals of the present invention can be produced by introducing a genomic region encoding one or more types of CD3s selected from the group consisting of human CD3ε, CD3δ, and CD3γ into non-human animals. In a non-limiting embodiment, positions in a non-human animal genome where one or more types of human CD3 genes selected from the group consisting of human CD3ε, CD3δ, and CD3γ are introduced are preferably different positions from the endogenous CD3 gene loci of the non-human animal, but are not limited thereto. When introducing a nucleotide sequence encoding human CD3, those skilled in the art can suitably select an expression regulatory region (promoter) that is appropriate for the objective of obtaining a desired expression distribution and/or expression level, link it to the nucleotide sequence of human CD3 gene(s), and then, introduce this into the genome.

In the present invention, endogenous CD3 gene(s) whose function is to be deleted may be any one or more types selected from the group consisting of CD3ε, CD3δ, and CD3γ, but for example, at least the endogenous CD3ε gene may be functionally deleted. It is also preferable to functionally delete two or more types thereof, for example, at least the endogenous CD3ε and CD3δ, the endogenous CD3ε and CD3γ, or the endogenous CD3δ and CD3γ are functionally deleted. Alternatively, all of the endogenous CD3ε, CD3δ, and CD3γ may be functionally deleted.

Furthermore, in the present invention, one or more types of CD3s selected from the group consisting of human CD3ε, CD3δ, and CD3γ are not particularly limited, but may be, for example, human CD3ε. CD3s may be two or more types of CD3s selected from the group consisting of human CD3ε, CD3δ, and CD3γ, and may be, for example, human CD3ε and CD3δ, human CD3ε and CD3γ, or human CD3δ and CD3γ. They may also be CD3s comprising human CD3ε, CD3δ, and CD3γ, i.e., all three types.

Cre, Dre, Flp, and such may be used as recombinases that act sequence-specifically in the present invention. A specific recombinase for a substrate sequence to be inserted into the genomic region is used. Specifically, the loxP sequence is used for Cre, the Rox sequence is used for Dre, and the Frt sequence is used for Flp. Here, without being limited to the following, the nucleotide sequence ATAACTTCGTATA GCATACATTATACGAAGTTAT (SEQ ID NO: 1) may be used as the "loxP sequence", the nucleotide sequence TAACTTTAAATAATTGGCATTATTTAAAGTTA (SEQ ID NO: 2) may be used as the "Rox sequence", and the nucleotide sequence GAAGTTCC TATTCTCTAGAAAGTATAGGAACTTC (SEQ ID NO: 3) may be used as the "Frt sequence".

In the present invention, the phrase "functionally express human CD3 gene(s)" refers to the condition where human CD3 molecule(s) is/are expressed on T cells of non-human animals and immunocompetent cells including the T cells maintain normal functions in the non-human animals. Whether the immunocompetent cells maintain normal functions can be determined by using as indicators, for example, the differentiation process of T cells, maturation process of T cells, thymus weight, number of thymocytes, and the ratio of CD4-positive and CD8-positive cells among functional T cells in the spleen, in the non-human animals.

Preferably, the genetically modified non-human animals of the present invention have an ability of mature T cell differentiation and production. More specifically, in the present invention, functionally expressing human CD3 gene may mean that mature T cells are produced in such animals. For example, when the genetically modified non-human animals of the present invention are mice, preferably, their T cell differentiation and maturation processes are not affected and the thymus weight and the number of thymocytes are equivalent to those of a normal mouse. The number of thymocytes equivalent to that of a normal mouse means that the number of thymocytes in a genetically modified non-human animal is at least $1\times10^4$ cells or more, preferably $1\times10^5$ cells or more, $5\times10^5$ cells or more, $1\times10^6$ cells or more, $5\times10^6$ cells or more, $1\times10^7$ cells or more, or particularly preferably $5\times10^7$ cells or more, and most preferably the number of thymocytes of a genetically modified non-human animal is in the range of $5\times10^7$ to $6\times10^7$ cells.

Furthermore, the ratio of cells positive for a surface marker for functional T cells, Cd4 or Cd8, is preferably equivalent to that of a normal mouse. Here, being equivalent to the ratios of Cd4- and Cd8-positive cells among mature T cells in a normal mouse means that when evaluated in the spleen, the ratio of Cd4-positive cells to the total number of mature T cells is preferably 10% to 40%, 12% to 38%, 14% to 36%, 16% to 34%, 18% to 32%, and particularly preferably 20% to 30%. Furthermore, the ratio of Cd8-positive cells to the total number of mature T cells is preferably 5% to 30%, 7% to 28%, 9% to 26%, 11% to 24%, 13% to 22%, and particularly preferably 15% to 20%.

In methods for evaluating the thymus weight, number of thymocytes, and abundance ratios of CD4-positive cells and CD8-positive cells in the periphery of a non-human animal, those skilled in the art can appropriately use, for example, well-known analysis methods, such as the analysis methods described in the following Examples, to conduct the evaluation.

Immunocompetent cells including T cells of the human CD3-substituted mice preferably have an equivalent cell proliferation ability after mitogen stimulation, as compared to those of wild-type mice. Being equivalent means that after mitogen stimulation the evaluated values of thymidine uptake, bromodeoxyuridine uptake, MTS assay, and 5-(and 6)-carboxyfluorescein diacetate succinimidyl ester (CFSE) assay are preferably 65% to 135%, 70% to 130%, 75% to 125%, 80% to 120%, and particularly preferably 85% to 115% of those of the wild-type.

In a non-limiting embodiment of the present invention, a genetically modified non-human animal of the present invention has increased ability to produce mature T cells as compared to a control that does not express the human CD3 genes (an animal deficient in the same combination of endogenous CD3 genes as that of the above-mentioned animal). More specifically, a total of CD4 single positive cells and CD8 single positive cells in the spleen is, for example, 1.3-times or more, preferably 1.5-times or more, more preferably 1.6-times or more, 2-times or more, 3-times or more, 4-times or more, 5-times or more, 10-times or more, 20-times or more, 50-times or more, or 100-times or more compared to that of the control. The developmental stage at which mature T cells are counted can be any stage as long as it is a stage at which mature T cells are produced in an animal of the present invention, preferably, the age when an animal typically reaches adulthood, for example, 8- to 12-weeks old, such as 12-weeks old, for mice.

Furthermore, the genetically modified non-human animals of the present invention have the ability to produce antibodies, for example, against foreign antigens. The types of antibodies are not particularly limited, and for example, it may be IgG (such as IgG1) or IgE. The foreign antigens are not particularly limited, and antibody production can be confirmed using a desired antigen, such as chicken ovalbumin (OVA).

In a non-limiting embodiment of the present invention, genetically modified non-human animals of the present invention has high antibody-producing ability as compared to a control that does not express the human CD3 genes (an animal deficient in the same combination of endogenous CD3 genes as that of the above-mentioned animals). Herein, the types of antibodies are not particularly limited, and for example, it may be IgG (such as IgG1) or IgE. Whether antibody-producing ability is increased can be determined by, following foreign antigen inoculation, observing whether antibodies are produced or measuring the amount of antibodies produced. The foreign antigen is not particularly limited, and antibody production can be confirmed using a desired antigen, for example, chicken ovalbumin (OVA). The antibody titer in the genetically modified non-human animals of the present invention i, for example, 1.3-times or more, preferably 1.5-times or more, more preferably 1.6-times or more, 2-times or more, 3-times or more, 4-times or more, 5-times or more, 10-times or more, 20-times or more, 50-times or more, or 100-times or more as compared to that of the control animal. The developmental stage at which antibody production is induced can be any stage as long as it is a stage at which antibodies are produced in an animal of the present invention, preferably, the age when an animal typically reaches adulthood, for example, 8- to 12-weeks old, such as 12-weeks old, for mice. The timing for antigen immunization and the timing for antibody measurement can be set appropriately, and for example, immunization can be performed twice with a four-week interval, where an initial immunization is performed by subcutaneously applying 100 µg of an antigen with complete Freund's adjuvant to the dorsal region, four weeks thereafter, a similar immunization is performed by subcutaneously applying the antigen with incomplete Freund's adjuvant to the dorsal region, then blood is collected one week after the second immunization, and the antibody titer can be measured.

Furthermore, in a non-limiting embodiment of the present invention, the condition where immunocompetent cells including T cells maintain normal functions includes a condition where functions relating to acquired immunity (humoral immunity, and cellular immunity) in the genetically modified non-human animals are kept normal.

In a non-limiting embodiment of the present invention, a genetically modified non-human animal of the present invention is a genetically modified non-human animal, in which a full-length nucleotide sequence of at least one or more types of human CD3 genes selected from the group consisting of human CD3ε, CD3δ, and CD3γ is inserted into the genome. Regarding the full-length nucleotide sequences to be inserted into the genome, the one or more types of CD3s selected from the group consisting of human CD3ε, CD3δ, and CD3γ are not particularly limited, and the sequence may be for example, a full-length nucleotide sequence of human CD3ε. Furthermore, CD3s may be two or more types of CD3s selected from the group consisting of human CD3ε, CD3δ, and CD3γ and the sequences may be for example, a full-length nucleotide sequence of human CD3ε and a full-length nucleotide sequence of CD3δ, a full-length nucleotide sequence of human CD3ε and a full-length nucleotide sequence of CD3γ, or a full-length nucleotide sequence of human CD3δ and a full-length nucleotide sequence of CD3γ. The sequences may also be those of CD3s comprising a full-length nucleotide sequence of human CD3ε, a full-length nucleotide sequence of CD3δ, and a full-length nucleotide sequence of CD3γ, i.e., all three types. In a non-limiting embodiment of the present invention, a "full-length nucleotide sequence" of a CD3 gene refers to a nucleotide sequence encoding a CD3 molecule (CD3ε, CD3δ, or CD3γ) including the extracellular, transmembrane, and cytoplasmic regions, and the nucleotide sequence may also include an expression regulatory region (promoter).

In the present invention, the phrase "a non-human animal" is not particularly limited, and is preferably a non-human mammal. A rodent such as a mouse, a rat, or a hamster, a non-human primate such as a monkey or a chimpanzee, other mammals such as a rabbit, sheep, cattle, or a pig, birds, amphibians, reptiles, fish, or such can be used as a non-human animal of the present invention. The non-human animal is particularly preferably a rodent, and most preferably a mouse.

As a non-limiting embodiment of a genetically modified non-human animal of the present invention, preferably, DNA (genomic DNA, complementary DNA (cDNA), or such) encoding human CD3 gene(s) selected from among human CD3ε, CD3δ, and CD3γ is introduced into the chromosome. Methods for introducing the DNA encoding human CD3 gene(s) selected from among human CD3ε, CD3δ, and CD3γ are not particularly limited, and known methods can be used appropriately, including introduction of DNA vectors or viral vectors such as retroviral vectors into the pronuclei of fertilized eggs by microinjection, into germline stem cells such as embryonic stem cells, sperm stem cells, or induced pluripotent stem cells (iPS cells) by electroporation or lipofection. The DNA vectors are not particularly limited as long as they are vectors used in genetic engineering, and for example, a plasmid vector, a viral vector, a cosmid vector, a bacterial artificial chromosome (BAC), a yeast artificial chromosome (YAC), and other non-plasmid vectors may be used.

A non-limiting embodiment of the present invention provides the above-mentioned genetically modified non-human animals for screening for therapeutic agents for malignant neoplastic disease or autoimmune disease. Furthermore, a non-limiting embodiment provides the above-mentioned genetically modified non-human animals for screening for therapeutic or prophylactic agents for allergies, diseases relating to T cell abnormality, graft rejection, and such instead of malignant neoplastic disease or autoimmune disease. Furthermore, it is also possible to examine therapeutic effects by transplantation of immunocompetent cells collected from the above-mentioned genetically modified non-human animals into disease model animals known to those skilled in the art for the examination of therapeutic effects mentioned above.

Furthermore, genetically modified non-human animals of the present invention may have cells transplanted therein.

The origin of the cells is not particularly limited, and for example, they are cells derived from an animal of the same species as the above-mentioned animals, and more preferably, to avoid immunological rejection, the cells have the same genetic background as the above-mentioned animals. Furthermore, the cells may be cancer cells or cell lines established from cancer cells. Furthermore, in a preferred embodiment, the cells express a protein containing at least an epitope of at least a human protein. Such a protein may be, for example, a protein at least containing a fragment of a human protein, and may be for example, a full-length human protein. The protein is preferably a protein containing at least an epitope of a human cancer antigen or an autoimmune disease autoantigen, and may be for example, a human cancer antigen itself or an autoimmune disease autoantigen itself. Furthermore, such a protein is preferably a cell surface protein, and more preferably a protein comprising a human protein epitope in the extracellular region. In a preferred embodiment, cells transplanted into a genetically modified non-human animal of the present invention express human protein epitopes on their cell surface.

Furthermore, as a non-limiting embodiment of the present invention, genetically modified non-human animals for assaying or screening for therapeutic agents for malignant neoplastic disease are provided, which are the above-mentioned genetically modified non-human animals into which cancer cells have been transplanted. Alternatively, it is also possible to screen for therapeutic agents for malignant neoplastic disease by transplanting immunocompetent cells collected from the above-mentioned genetically modified non-human animals into non-human animals into which cancer cells have been transplanted. Furthermore, as a non-limiting embodiment, the present invention also relates to the use of the above-mentioned genetically modified non-human animals for assaying or screening for therapeutic agents for malignant neoplastic disease.

When mice are used as the genetically modified non-human animals of the present invention, for example, when used for evaluating therapeutic antibodies as allograft models of cancer cell lines derived from non-human animals, it is preferable to use mouse cancer cell lines into which human cancer antigens have been introduced. "Cancer cell lines derived from non-human animals" are not particularly limited, but to avoid immunological rejection in the non-human animals of the present invention, they preferably have the same genetic background as that of the non-human animals of the present invention. "Human cancer antigens" refer to molecules whose expression is not observed in normal human tissues and increases specifically due to malignant transformation. Herein, molecules whose expression increases specifically due to malignant transformation refer to proteins, abnormal carbohydrate chains that appear on cell surfaces or on protein molecules, or such, and preferably refer to cell surface proteins. Methods for expressing human cancer antigens on cancer cells of non-human animals are not particularly limited, but stable strains can be established by introduction of expression vectors. The expression vectors are not particularly limited as long as they are vectors used in genetic engineering, and for example, a plasmid vector, a viral vector, a cosmid vector, a bacterial artificial chromosome (BAC), a yeast artificial chromosome (YAC), and other non-plasmid vectors may be used.

Suitable examples of cancer cells to be transplanted into non-human animals for screening for therapeutic agents for malignant neoplastic disease in the present invention include ovarian cancer, prostate cancer, breast cancer, esophageal cancer, renal cancer, uterine cancer, liver cancer, lung cancer, pancreatic cancer, gastric cancer, bladder cancer, or colon cancer cells. "Cancer" described herein refers to not only epithelial malignant tumors such as ovarian cancer and gastric cancer, but also nonepithelial malignant tumors including cancer of hematopoietic organs such as chronic lymphocytic leukemia and Hodgkin's lymphoma.

Specific examples of autoimmune diseases in the present invention include diseases such as rheumatism, autoimmune hepatitis, autoimmune thyroiditis, autoimmune bullous, autoimmune adrenocortical inflammation, autoimmune hemolytic anemia, autoimmune thrombocytopenic purpura, autoimmune atrophic gastritis, autoimmune neutropenia, autoimmune orchitis, autoimmune encephalomyelitis, autoimmune receptor disease, autoimmune infertility, Crohn's disease, systemic lupus erythematosus, multiple sclerosis, Basedow's disease, juvenile diabetes, Addison's disease, myasthenia gravis, lens-induced uveitis, psoriasis, and Behcet's disease.

A non-limiting embodiment of the present invention provides genetically modified non-human animals, in which a non-human animal-derived T cell receptor and human CD3 molecule(s) form a complex on T cells carried by the above-mentioned genetically modified non-human animals.

Here, CD3ε forms a dimer with CD3δ or CD3γ, and then these dimers form a complex with the T cell receptor (TCR) α chain and the TCRβ chain, thereby forming a functional TCR complex. Without being bound to a particular theory, in genetically modified non-human animals of the present invention, human-derived CD3ε, CD3δ, and/or CD3γ can form a complex together with a non-human animal-derived TCR α chain and β chain on the T cells of the above-mentioned non-human animals.

A non-limiting embodiment of the present invention provides a method for producing a genetically modified non-human animal, which comprises the steps of:

(1) functionally deleting at least one or more types of CD3 genes selected from the group consisting of endogenous CD3ε, CD3δ, and CD3γ in the genome; and (2) introducing at least one or more types of human CD3 genes selected from the group consisting of human CD3ε, CD3δ, and CD3γ into the genome.

The "step of introducing human CD3 gene(s) into the genome" in the present invention is not particularly limited to a certain gene transfer technique as long as human CD3 gene(s) (human CD3 selected from the group consisting of CD3ε, CD3δ, and CD3γ) is introduced into the genome of a non-human animal, and for example, known methods can be used appropriately, including introduction of DNA vectors into the pronuclei of fertilized eggs by microinjection, into germline stem cells such as embryonic stem cells, sperm stem cells, or induced pluripotent stem cells (iPS cells) by electroporation or lipofection. The DNA vectors are not particularly limited as long as they are vectors used in genetic engineering, and for example, a plasmid vector, a viral vector, a cosmid vector, a bacterial artificial chromosome (BAC), a yeast artificial chromosome (YAC), and other non-plasmid vectors may be used.

Furthermore, in a non-limiting embodiment, genetically modified non-human animals of the present invention can be produced by modifying target gene(s) using a technique of zinc finger nucleases (U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626), TALEN (U.S. Pat. No. 8,420,782 B2, U.S. Pat. No. 8,440,431, U.S. Pat. No. 8,440,432, and U.S. Pat. No. 8,450,471), or CRISPER-Cas (CRISPR/Cas9) (U.S. Pat. No. 8,697,359, U.S. Pat. No. 8,795,965, U.S. Pat. No. 8,771,945, WO2013/142578, WO2013/176772, WO2014/065596, WO2014/089290, and WO2014/093595). In a non-limiting embodiment, positions in the genome of the non-human animals where one or more types of human CD3 genes selected from the group consisting of human CD3ε, CD3δ, and CD3γ are introduced are preferably different positions from the endogenous CD3 gene loci of the non-human animals, but are not limited thereto. When introducing a nucleotide sequence encoding human CD3, those skilled in the art can suitably select an expression regulatory region (promoter) that is appropriate for the objective of obtaining a desired expression distribution and/or expression level, link it to the nucleotide sequence of human CD3 gene(s), and introduce this into the genome.

In the present invention, the steps of deleting a gene in a genome and introducing a gene into a genome are not particularly limited as long as in the respective steps an individual in which such gene has been deleted in its genome and an individual in which such gene has been introduced into its genome is obtained, and include for example, obtaining such an individual by crossing. For example, an individual carrying a gene of interest in its genome can be crossbred with an individual lacking the gene in its genome once or multiple times to produce individuals in which the gene has been deleted in the genome. Conversely, an individual not carrying a gene of interest can be crossbred with an individual carrying the gene in its genome (donor) once or multiple times to produce individuals in which the gene has been introduced into the genome. For example, crossbreeding of an individual which is functionally deficient in at least one or more types of CD3 genes selected from the group consisting of endogenous CD3ε, CD3δ, and CD3γ in its genome with an individual carrying at least one or more types of human CD3 genes selected from the group consisting of human CD3ε, human CD3δ, and human CD3γ in its genome (an individual carrying human CD3 gene(s) at chromosome regions different from those of endogenous CD3 gene(s)) is capable of resulting in individuals in which at least one or more types of CD3 genes selected from the group consisting of endogenous CD3ε, CD3δ, and CD3γ have been deleted in the genome and at least one or more types of human CD3 genes selected from the group consisting of human CD3ε, human CD3δ, and human CD3γ have been introduced into the genome. Accordingly, in the present invention, deletion in a genome or introduction into a genome includes deletion or introduction by crossing, respectively.

In the present invention, while not intending to particularly limit the sequences of the human CD3 genes to be introduced into non-human animals as long as the CD3 genes are human-derived, for example, for human CD3γ, human CD3δ, and human CD3ε, the polynucleotide sequences are shown in SEQ ID NO: 4 (NM_000073.2), SEQ ID NO: 6 (NM_000732.4), and SEQ ID NO: 8 (NM_000733.3), respectively, and the polypeptide sequences are shown in SEQ ID NO: 5 (NP_000064.1), SEQ ID NO: 7 (NP_000723.1), and SEQ ID NO: 9 (NP_000724.1), respectively (RefSeq accession numbers are shown in parentheses).

In a non-limiting embodiment of the present invention, as long as the downstream signaling takes place normally, the extracellular region sequences of the non-human animal-derived CD3 molecules (ε, δ, and/or γ) can be modified to the extracellular region sequences of the human-derived CD3 molecules (ε, δ, and/or γ) to produce genetically modified non-human animals of the present invention.

More specifically, the present invention provides modified non-human animals which are modified so that the expression of endogenous CD3 protein(s) selected from the group consisting of CD3ε, CD3δ, and CD3γ is suppressed or deleted and which express functional CD3 protein(s) carrying at least the extracellular region(s) of human CD3 protein(s) selected from the group consisting of human CD3ε, CD3δ, and CD3γ. The functional CD3 protein(s) may be one, two, or three desired proteins among CD3ε, CD3δ, and CD3γ, but the animals preferably express at least the CD3 protein(s) corresponding to the endogenous CD3 protein(s) whose expression is suppressed or deleted (for example, the functional CD3 protein carrying at least the extracellular region of the human CD3ε protein when the expression of endogenous CD3ε protein is suppressed or deleted, the functional CD3 protein carrying at least the extracellular region of the human CD3δ protein when the expression of endogenous CD3δ protein is suppressed or deleted, and the functional CD3 protein carrying at least the extracellular region of the human CD3γ protein when the expression of endogenous CD3γ protein is suppressed or deleted).

Herein, "modified to suppress expression of endogenous CD3 protein(s)" is an embodiment of a modification that may functionally delete an endogenous CD3 gene in the genome, and it may be a modification that alters (mutates, deletes, or such) endogenous CD3 protein-coding gene(s) to thereby cause intact endogenous CD3 protein(s) to become not expressed or expressed at a low level, or completely not expressed, or alternatively, it may be a modification that causes the expression of endogenous CD3 protein(s) to become suppressed at the transcriptional level or translational level. It may also cause a decrease in the stability, promotion of the degradation, or shortening of the half-life of the protein(s).

The three types of functional CD3 proteins carrying the extracellular regions of human CD3ε, CD3δ, and CD3γ refer to afunctional CD3 protein carrying the extracellular region of human CD3ε, a functional CD3 protein carrying the extracellular region of human CD3δ, and a functional CD3 protein carrying the extracellular region of human CD3γ, respectively. The functional CD3 proteins may be human CD3 proteins themselves, or chimeric CD3 proteins of human CD3 proteins and non-human animal CD3 proteins. For example, chimeric CD3 proteins in which the extracellular region is derived from a human CD3 protein and the other regions are derived from a CD3 protein of the animals are also included. In the case of chimeric CD3 proteins, functional CD3 proteins carrying at least the extracellular region of human CD3ε, CD3δ, or CD3γ preferably have regions other than the extracellular region (such as cytoplasmic region) that are also derived from the CD3ε, CD3δ, or CD3γ, respectively.

Furthermore, a functional CD3 protein refers to a protein that has the function of a CD3 protein, for example the activity to form a complex with the TCRα chain and TCRβ chain, the activity to produce mature T cells, and/or the activity to produce antibodies against foreign antigens. Functional CD3 proteins specifically include proteins that significantly increase production of mature T cells and/or antibody production, compared to those in animals modified so that the expression of at least one or more types of endogenous CD3 proteins selected from the group consisting of CD3ε, CD3δ, and CD3γ are suppressed, when expressed in the animals as functional CD3 proteins carrying at least the human CD3 extracellular regions.

From the properties described above, non-human animals of the present invention can be used for various evaluations of test substances concerning therapeutic effects on a disease, pharmacokinetics, or such. Accordingly, the present invention also provides such methods for evaluating test substances using the non-human animals of the present invention. Furthermore, the present invention relates to non-human animals of the present invention for use in various evaluations of test substances for their therapeutic effects on a disease, pharmacokinetics, or such, and/or screening, and also relates to uses of the non-human animals of the present invention in various evaluations of test substances for their therapeutic effects on a disease, pharmacokinetics, or such, and/or screening.

A non-limiting embodiment of the present invention provides a method of screening for a therapeutic agent for malignant neoplastic disease or autoimmune disease or its candidate, which comprises the steps of:
  (1) contacting a test substance with a genetically modified non-human animal mentioned above, or an organ, tissue, or cell thereof; and
  (2) selecting a candidate test substance using as indicators drug efficacy and/or toxicity of the test substance on the non-human animal individual, or the organ, tissue, or cell thereof.

Furthermore, a non-limiting embodiment provides a method of screening for a therapeutic or prophylactic agent for allergies, diseases relating to T cell abnormality, graft rejection, and such instead of malignant neoplastic disease or autoimmune disease.

The "test substance" to be used in evaluation methods of the present invention is not particularly limited, and includes for example, peptides, proteins, non-peptide compounds, synthetic compounds, fermentation products, and cell extracts. For example, test substances that bind to human CD3 which is at least any one of human CD3ε, CD3δ, and CD3γ, or test substances that become candidates thereof may be used. Human CD3-binding antibodies are preferred, and bispecific antibodies that bind to both human CD3 and a cancer-specific antigen simultaneously are particularly preferred. By carrying out the screening methods of the above-mentioned embodiment, therapeutic agents for various diseases including the candidate test substances selected in step (2) can be selected.

The step of contacting a test substance with the genetically modified non-human animals of the present invention can be carried out by administration of the test substance to the non-human animals, for example by tail vein administration, subcutaneous administration, intraperitoneal administration, oral administration, transnasal administration, transdermal administration, or transpulmonary administration.

Furthermore, in another embodiment, "contacting" in the present invention is carried out by administering an antigen-binding molecule that binds to a human CD3 molecule and a cancer-specific antigen to a non-human animal into which cells expressing the cancer-specific antigen have been transplanted or to an animal having cancer cells endogenously expressing the cancer-specific antigen. The method of administration may be oral or parenteral. Parenteral administration is particularly preferred, and specific examples of the method of administration are injection, transnasal administration, transpulmonary administration, and transdermal administration. Examples of administration by injection include intravenous injection, intramuscular injection, intraperitoneal injection, and subcutaneous injection. The aforementioned antigen-binding molecules can be administered systemically or locally, for example, by injection. The method of administration can be selected appropriately according to the age and symptoms of the test animals. When administered as an aqueous solution, an aqueous solution simply containing the aforementioned antigen-binding molecule alone may be used, or for example, a solution also containing surfactants, excipients, coloring agents, perfumes, preservatives, stabilizers, buffers, suspending agents, isotonization agents, binders, disintegrants, lubricants, fluidity promoting agents, flavoring agents, and such described above may be used. The dose can be selected in the range of 0.0001 mg to 1000 mg per kilogram body weight for a singular administration. However, the amount of the antigen-binding molecule to be administered is not limited to these doses.

Cells of genetically modified non-human animals used in the screening method of this embodiment are not particularly limited as long as they are the cells themselves or anything containing the cells (such as blood, tissues, or organs). The blood, tissues, organs, or such may be isolated from a living organism and cultured, or alternatively a test substance can be administered to the living organism itself and after a certain period of time such biological samples can be isolated.

In the present invention, "contacting" is carried out, for example, by adding, to a cultured medium of in vitro cultured cells expressing a targeted antigen, an antigen-binding molecule that binds to the antigen and cells of a genetically modified non-human animal of the present invention or samples containing the cells (blood, tissues, organs, or such). In this case, the antigen-binding molecule to be added may be suitably used in the form of a solution, or a solid obtained by freeze-drying or such. When added as an aqueous solution, it may be an aqueous solution that simply contains the above-mentioned antigen-binding molecule alone, or it may be a solution also containing, for example, the above-mentioned surfactants, excipients, coloring agents, perfumes, preservatives, stabilizers, buffers, suspending agents, isotonization agents, binders, disintegrants, lubricants, fluidity promoting agents, and flavoring agents. The concentration of the molecule to be added is not particularly limited, but a suitable final concentration in the culture medium is preferably in the range of 1 pg/ml to 1 g/ml, more preferably 1 ng/ml to 1 mg/ml, and even more preferably 1 µg/ml to 1 mg/ml.

A test substance and the above-mentioned cells, for which isolated cells, tissues, or such are used, can be contacted by for example, adding a test substance to a medium suitable for culturing the cells, tissues, or such (for example, minimum essential medium (MEM), Dulbecco's modified Eagle's medium (DMEM), RPMI1640 medium, 199 medium, F12 medium, or the like, containing approximately 5% to 20% of fetal bovine serum) or any of various buffers (for example, HEPES buffer, phosphate buffer, phosphate buffered saline, Tris-HCl buffer, borate buffer, acetate buffer, or the like), and incubating the cells for a certain period of time, but, without being limited thereto, those skilled in the art can select suitable conditions. Although the concentration of the test substance to be added varies depending on the type of the compound (solubility, toxicity, and the like), the concentration can be appropriately selected by those skilled in the art. The incubation time is, for example, approximately ten minutes to approximately 24 hours.

Drug efficacy and/or toxicity of test substances in the genetically modified non-human animal individuals of the present invention, organs, tissues, or cells thereof can be measured to select the test substances confirmed to have drug efficacy or high drug efficacy, or to select the test substances with low or no toxicity. Alternatively, similar measurements can be performed using substances having drug efficacy as a comparative control, and test substances having high drug efficacy or low toxicity compared to that of the control can be selected. Drug efficacy is not particularly limited, and includes for example cell proliferation inhibitory effect, cytotoxicity, or tumor growth inhibitory effect.

An embodiment of the present invention provides a method of screening for a therapeutic agent for malignant neoplastic disease, or a candidate thereof, which comprises the steps of:
(1) administering as a test substance, one from a library of antigen-binding molecules comprising a human CD3-binding domain and a cancer-specific antigen-binding domain to a first genetically modified non-human animal mentioned above;
(2) measuring a cell proliferation inhibitory effect and/or pharmacokinetic characteristics of the test substance on a cell expressing the cancer-specific antigen; and
(3) comparing the cell proliferation inhibitory effect and/or pharmacokinetic characteristics of the test substance to a cell proliferation inhibitory effect and/or pharmacokinetic characteristics of a control substance administered to a second genetically modified non-human animal which is different from the first non-human animal.

As the first and second genetically modified non-human animals, for example, those in which the same modifications have been made to the endogenous CD3 gene(s) can be used. Examples of the control substance include control antibodies. For the control antibodies, antibodies that bind to a human CD3-binding domain and a cancer-specific antigen-binding domain may be used appropriately. Excellent therapeutic agents for malignant neoplastic disease can be screened for by selecting test substances with high cell proliferation inhibitory effects or selecting test substances with favorable pharmacokinetic characteristics, compared to those of a control antibody.

Embodiments of test substance evaluation are exemplified by the following. For example, therapeutic effect can be evaluated by measuring whether proliferation of a cancer cell line that expresses a cancer-specific antigen is suppressed in a non-human animal of the present invention into which the cancer cell line has been transplanted. The cancer cell line is a cancer cell line into which a human cancer antigen has been introduced and which is preferably derived from the same species as the non-human animal to be used for the screening. Whether proliferation of the transplanted cancer cell lines has been suppressed can be evaluated by measuring the amount of the cancer cell line or the size of the grown mass.

An embodiment of the test substance evaluation is, for example a method for measuring cytotoxicity. The following method is suitably used as a method for evaluating or measuring cytotoxicity induced in the cancer cells or tumor tissues containing cancer cells of interest by contact with an antigen-binding molecule which is the test substance. Examples of methods for evaluating or measuring the cytotoxic activity in vitro include methods for measuring cytotoxic T cell activity, and such. Whether an antigen-binding molecule has T cell-mediated cytotoxicity can be measured by known methods (for example, Current protocols in Immunology, Chapter 7. Immunologic studies in humans, Editor, John E. Coligan et al., John Wiley & Sons, Inc., (1993) and the like). In the activity measurements, an antigen-binding molecule binding to an antigen which is different from that bound by the antigen-binding domain of the test substance and which is not expressed in the transplanted cells used in the examination is used as a control in the same manner as the antigen-binding molecule of the test substance. When the antigen-binding molecule used as the test substance shows stronger cytotoxic activity than the antigen-binding molecule used as a control, activity of the test substance can be determined. Consequently, such a test substance can be selected.

Meanwhile, to evaluate or determine in vivo cytotoxic activity, for example, cancer cells or tumor tissues containing cancer cells targeted by an antigen-binding molecule used as the test substance are transplanted intracutaneously or subcutaneously to a non-human animal of the present invention, and then, from the day of transplantation or the following day, the test antigen-binding molecule is administered intravenously or intraperitoneally every day or at intervals of several days. Through measurement of the tumor size over time, difference in the change of tumor size can be defined as the cytotoxic activity. Similarly to the in vitro evaluation, a control antigen-binding molecule is administered, and, when the tumor size in the group to which an antigen-binding molecule used as a test substance has been administered is significantly smaller than the tumor size in the group to which the control antigen-binding molecule has been administered, the antigen-binding molecule of the present invention can be determined to have cytotoxic activity. Consequently, such a test substance can be selected.

Furthermore, pharmacokinetic characteristics of the test substance can be evaluated by measuring the concentration of a test substance in blood of a non-human animal of the present invention to which the test substance has been administered. Herein, the term "pharmacokinetic characteristics" refers to properties of a test substance in the body of an animal, such as the effective blood concentration, blood half-life, and elimination rate. For example, a substance having a higher effective blood concentration, a longer blood half-life, or a slower elimination rate is determined to have superior pharmacokinetic characteristics. The method for measuring the concentration of a test substance in blood is not particularly limited. When the test substance is a protein (including an antibody), the method may be ELISA, and when the test substance is a small molecule compound, the method may be liquid chromatography-mass spectrometry (LC-MS). Regarding the methodology for evaluating pharmacokinetic characteristics based on the blood concentration, see the document by Igawa et al. (2010) Nat. Biotechnol. 28:1203-1207.

Use of the above-mentioned methods for evaluating test substances of the present invention enables efficient selection of antibodies against human CD3 and human cancer-specific antigens that have a desired activity. Therefore, the present invention also provides a method for selecting such an antibody.

Antibodies that efficiently inhibit the proliferation of cancer cells expressing human cancer-specific antigens can be obtained by determining, in the non-human animals to which a mouse cancer cell line expressing human cancer-specific antigens has been transplanted and then antibodies against the human cancer-specific antigens and human CD3 have been administered as the test substances, whether proliferation of the cancer cell line was suppressed, and selecting antibodies that suppress the symptom.

Furthermore, in non-human animals to which antibodies thus produced are administered, the blood concentration of antibodies is measured, and antibodies having a desired blood concentration are selected to obtain antibodies that bind to both human CD3 and a cancer-specific antigen and that have the desired biokinetics in the body.

When antibodies evaluated for the activity and selected as mentioned above are mouse monoclonal antibodies and such, these antibodies can be chimerized or humanized to obtain antibodies with low antigenicity as well as few side effects when administered to humans.

In one embodiment of the present invention, antigen-binding molecules provided for the above-mentioned methods of screening for therapeutic agents for malignant neoplastic disease may be those comprising (1) a human CD3-binding domain and (2) a cancer-specific antigen-binding domain, and their structures are not limited. By comprising these two binding domains, the antigen-binding molecules can induce excellent activated T cell-mediated cytotoxicity against cancer cells or tumor tissues containing the cancer cells. The binding domains of the present invention described in (1) and (2) can be selected appropriately from the later-described human CD3 antigens or cancer-specific antigens, respectively. These binding domains can be linked directly through a peptide bond or linked via a linker.

Antigen-binding molecules of the present invention may further comprise an FcRn-binding domain. When using Fc regions of the later-described antibody as the FcRn-binding domain, those having reduced Fcγ receptor-binding activity are preferred. Reduction of the Fcγ receptor-binding activity enables suppression of side effects produced by systemic immune activation, such as cytokine release caused by crosslinking between Fcγ receptor-expressing cells and T cell receptor complex-expressing cells.

Antigen-binding molecules of the present invention can be produced using the known methods described above.

For example, when (i) F(ab')$_2$ is used as the domain that binds to a molecule expressed on the surface of a cell having immune response-suppressing functions, (ii) F(ab')$_2$ is used as a T cell receptor complex-binding domain, and (iii) a domain comprising an Fc region with decreased Fcγ receptor-binding activity is used as the FcRn-binding domain, and when the antigen-binding domains described in (i) and (ii) and the Fc region-comprising domain described in (iii) are directly linked by peptide bonds, the linked polypeptides form an antibody structure. Such antibodies can be produced by purification from the above-described hybridoma culture medium, and also by purifying antibodies from the culture medium of desired host cells that stably carry polynucleotides encoding polypeptides constituting the antibody.

In addition to the linkers exemplified above, linkers with peptide tags such as His tag, HA tag, myc tag, and FLAG tag may also be suitably used as the linkers to be employed when connecting each of the domains via linkers. Furthermore, hydrogen bonding, disulfide bonding, covalent bonding, ionic interaction, or the property of mutual binding as a result of combination thereof may be suitably used. For example, the affinity between antibody CH1 and CL may be used, and Fc regions derived from the above-described multispecific antibodies may also be used for heterologous Fc region association.

When an antigen-binding molecule comprising a "CD3-binding domain" is used as a test substance in a method for producing or a method of screening for therapeutic agents for various diseases in the present invention, the CD3-binding domain may be provided from one or more antibody variable domains. Preferably, a CD3-binding domain comprises a CD3 antibody light chain variable region (VL) and a CD3 antibody heavy chain variable region (VH). Preferable examples of such CD3-binding domains include "single chain Fv (scFv)", single chain antibody", "Fv", "single chain Fv2 (scFv2)", "Fab", or "F(ab')$_2$".

The CD3-binding domain of the present invention may be those that bind to any epitope as long as the epitope exists in the γ-chain, δ-chain, or ε-chain sequence constituting human CD3. In the present invention, preferably, a CD3-binding domain that comprises a light chain variable region (VL) of a CD3 antibody and a heavy chain variable region (VH) of a CD3 antibody, and which binds to an epitope present in the extracellular region of the c chain of the human CD3 complex, is suitably used. For such CD3-binding domain, a CD3-binding domain comprising the light chain variable region (VL) and heavy chain variable region (VH) of the OKT3 antibody (Proc. Natl. Acad. Sci. USA (1980) 77, 4914-4917) or various known CD3 antibodies is suitably used. A CD3-binding domain derived from a CD3 antibody that has the desired properties and is obtained by immunizing a desired animal with the γ-chain, δ-chain, or ε-chain constituting the human CD3 by the later-mentioned method may be appropriately used. Human antibodies and appropriately humanized antibodies as described below may be suitably used as the CD3 antibody that serves as the origin for the CD3-binding domain.

A "cancer-specific antigen" bound by a cancer-specific antigen-binding domain of the present invention refers to an antigen expressed by cancer cells, which enables one to distinguish between cancer cells and healthy cells; and for example, it includes antigens that are expressed as cells become malignant, or abnormal sugar chains that appear on protein molecules or cell surface when cells become cancerous. Specific examples include ALK receptor (pleiotrophin receptor); pleiotrophin; KS 1/4 pancreas carcinoma antigen; ovarian carcinoma antigen (CA125); prostatic acid phosphate; prostate-specific antigen (PSA); melanoma-associated antigen p97; melanoma antigen gp75; high molecular weight melanoma antigen (HMW-MAA); prostate-specific membrane antigen; carcinoembryonic antigen (CEA); polymorphic epithelial mucin antigen; human milk fat globule antigen; colorectal tumor-associated antigens such as CEA, TAG-72, C017-1A, GICA 19-9, CTA-1, and LEA; Burkitt's lymphoma antigen-38.13; CD19; human B-lymphoma antigen-CD20; CD33; melanoma-specific antigens such as ganglioside GD2, ganglioside GD3, ganglioside GM2, and ganglioside GM3; tumor-specific transplantation type cell-surface antigen (TSTA); virus-induced tumor antigens including T antigen and envelope antigens of DNA tumor viruses and RNA tumor viruses; CEA of colon; oncofetal antigens such as5T4 oncofetal trophoblast glycoprotein and bladder tumor oncofetal antigen; α-fetoprotein; differentiation antigens such as human lung carcinoma antigens L6 and L20; antigens of fibrosarccancer antigenoma; human leukemia T cell antigen-Gp37; neoglycoprotein; sphingolipids; breast s such as EGFR (epidermal growth factor receptor); NY-BR-16; NY-BR-16 and HER2 antigen (p185HER2); polymorphic epithelial mucin (PEM); malignant human lymphocyte antigen-APO-1; differentiation antigens such as I antigen found in fetal erythrocytes; primary endoderm I antigen found in adult erythrocytes; preimplantation embryos; I(Ma) found in gastric cancer; M18 and M39 found in mammary epithelium; SSEA-1, VEP8, VEP9, Myl, and VIM-D5 found in myeloid cells; D156-22 found in colorectal cancer; TRA-1-85 (blood group H); SCP-1 found in testis and ovarian cancer; C14 found in colon cancer; F3 found in lung cancer; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric cancer antigen; CO-514 (blood group Lea) found in adenocarcinomas; NS-10 found in adenocarcinomas; CO-43 (blood group Leb); G49 found in EGF receptor of A431 cells; MH2 (blood group ALeb/Ley) found in colon cancer; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells as well as SSEA-3 and SSEA-4 found in 4 to 8-cell stage embryos; subcutaneous T cell lymphoma antigen; MART-1 antigen; sialyl Tn (STn) antigen; colon cancer antigen NY-CO-45; lung cancer antigen NY-LU-12 variant A; adenocarcinoma antigen ART1; paraneoplastic associated brain-testis-cancer antigen (onconeuronal antigen MA2; paraneoplastic neuronal antigen); Neuro-oncological ventral antigen 2 (NOVA2); hemocyte carcinoma antigen gene 520; tumor-associated antigen CO-029; tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1); YKL-40, fragments of any of the aforementioned polypeptides, or structures produced by modification thereof (for example, the above-mentioned modified phosphate group or sugar chain); EpCAM; EREG; CA19-9; CA15-3; sialyl SSEA-1(SLX); HER2; PSMA; CEA; and CLEC12A. Cancer-specific antigens which become targets of the cancer-specific antigen-binding domains of the present invention are, in particular, preferably those expressed on cell surface, and examples of such cancer-specific antigens include CD19, CD20, EGFR, HER2, EpCAM, EREG, and GPC3.

In the present invention, a library of antigen-binding molecules refers to a library containing one or more of antigen-binding molecules comprising a human CD3-binding domain and a cancer-specific antigen-binding domain.

Anon-limiting embodiment of the present invention provides a method for producing a therapeutic agent for malignant neoplastic disease or autoimmune disease, which comprises the steps of:
(1) contacting a genetically modified non-human animal mentioned above, or an organ, tissue, or cell thereof with a test substance; and
(2) selecting a candidate test substance using as indicators drug efficacy and/or toxicity of the test substance in the non-human animal individual, or the organ, tissue, or cell thereof.

For example, as a non-limiting embodiment, a test substance confirmed to have drug efficacy and/or a test substance confirmed to have no or permissible toxicity can be selected.

Furthermore, a non-limiting embodiment provides a method for producing therapeutic or prophylactic agents for allergies, diseases relating to T cell abnormality, graft rejection, and such instead of malignant neoplastic disease or autoimmune disease.

An embodiment of the present invention provides a method for producing a therapeutic agent for malignant neoplastic disease, which comprises the steps of:
(1) administering as a test substance, one from a library of antigen-binding molecules comprising a human CD3-binding domain and a cancer-specific antigen-binding domain to a first genetically modified non-human animal mentioned above;
(2) measuring a cell proliferation inhibitory effect and/or pharmacokinetic characteristics of the test substance on a cell expressing the cancer-specific antigen; and (3) comparing the cell proliferation inhibitory effect and/or pharmacokinetic characteristics of the test substance to a cell proliferation inhibitory effect and/or pharmacokinetic characteristics of a control substance administered to a second genetically modified non-human animal which is different from the first non-human animal.

For example, as the first and second genetically modified non-human animals those in which the same modifications have been made to the endogenous CD3 gene(s) can be used. Examples of the control substance include control antibodies. Excellent therapeutic agents for malignant neoplastic disease can be produced by selecting test substances with superior cell proliferation inhibitory effects or selecting test substances with favorable pharmacokinetic characteristics, compared to those of a control antibody.

An embodiment of the present invention provides a method for producing a bispecific antibody, which comprises the steps of:

(1) administering as a test substance, one from a library of bispecific antibodies comprising a human CD3-binding domain and a cancer-specific antigen-binding domain to a genetically modified non-human animal mentioned above;
(2) selecting a human CD3-binding domain and a cancer-specific antigen-binding domain that provide the antibody with superior cell proliferation inhibitory effect on cells expressing the cancer-specific antigen compared to that of a control antibody;
(3) obtaining a gene encoding a bispecific antibody prepared by linking the human CD3-binding domain and the cancer-specific antigen-binding domain selected in step (2); and
(4) producing the bispecific antibody using the gene prepared in step (3).

Antibodies that bind to a human CD3-binding domain and a cancer-specific antigen-binding domain can be suitably used as the control antibody.

In a non-limiting embodiment of the present invention, the above-mentioned genetically modified non-human animals of the present invention may be genetically modified non-human animals which further express human cancer-specific antigen gene, human immune checkpoint gene, and/or human immune costimulatory molecule gene. A human cancer-specific antigen refers to an antigen expressed by a cancer cell, which enables discrimination between cancer cells and healthy cells, and for example, it includes antigens that are expressed as cells become malignant or abnormal sugar chains that appear on the cell surfaces or on protein molecules when cells become cancerous. An "immune checkpoint" refers to a molecule that is expressed on immunocompetent cells and binds to a ligand to thereby transduce signals to the immunocompetent cells, which signals inhibit the cells' immune response. Examples of the immune checkpoints and their ligands include but are not limited to PD-1, CTLA-4, TIM3, LAG3, PD-L1, PD-L2, BTNL2, B7-H3, B7-H4, CD48, CD80, 2B4, BTLA, CD160, CD60, CD86, and VISTA. An "immune costimulatory molecule" refers to a molecule that is expressed on immunocompetent cells and binds to a ligand to thereby transduce signals that activate immune response caused by the immunocompetent cells. Examples of the immune costimulatory molecules include but are not limited to CD28, ICOS, CD137, CD137L, CD40, CD40L, OX40, OX40L, CD27, CD70, HVEM, LIGHT, RANK, RANKL, CD30, CD153, GITR, and GITRL. The above-mentioned genetically modified animals further expressing human cancer-specific antigen gene, human immune checkpoint gene, and/or human immune costimulatory molecule can be produced by appropriately using a method known to those skilled in the art, such as crossing a genetically modified animal expressing a human CD3 gene with a genetically modified animal expressing a human cancer-specific antigen gene, a human immune checkpoint gene, and/or a human immune costimulatory molecule, but not limited thereto.

The above-mentioned screening methods can be used as a method of screening for "therapeutic agents for malignant neoplastic diseases, which target cancer-specific antigens", "immune checkpoint inhibitors", or "immune costimulatory activators". In the present invention, "immune checkpoint inhibitors" refer to pharmaceutical agents that inhibit signal transduction mediated by an immune checkpoint through, for example, inhibition of binding between the immune checkpoint and its ligand. "Immune costimulatory activators" refer to pharmaceutical agents that activate signal transduction mediated by an immune costimulatory molecule through binding to the immune costimulatory molecule in place of its ligand.

As a non-limiting embodiment, the genetically modified non-human animals of the present invention can also be used in screening for compounds targeting not only the extracellular region but also the transmembrane region and/or the cytoplasmic region of non-human CD3ε, CD3δ, and CD3γ, since in the animals not only the extracellular region but also the transmembrane region and the cytoplasmic region of the CD3 molecules have been humanized. The genetically modified non-human animals of the present invention can be used for screening for compounds that modulate the interactions with related molecules inside and outside the cells. The genetically modified non-human animals of the present invention can also be used for screening for immunomodulators having the effect of activating or inhibiting T cell function.

Antibody

Herein, an "antibody" refers to a naturally occurring immunoglobulin or an immunoglobulin produced by partial or complete synthesis. Antibodies can be isolated from natural sources such as naturally-occurring plasma and serum, or culture supernatants of antibody-producing hybridoma cells. Alternatively, antibodies can be partially or completely synthesized using techniques such as genetic recombination. Suitable examples of the antibodies include antibodies of an immunoglobulin isotype or subclass of such isotype. Known human immunoglobulins include those of the following nine classes (isotypes): IgG1, IgG2, IgG3, IgG4, IgA1, IgA2, IgD, IgE, and IgM. Of these isotypes, antibodies include IgG1, IgG2, IgG3, and IgG4 in the present invention.

Methods for producing antibodies having the desired binding activity are known to those skilled in the art, and the antibodies may be obtained as polyclonal or monoclonal antibodies. Monoclonal antibodies derived from mammals may be suitably produced as the antibodies in the present invention. Such mammalian-derived monoclonal antibodies include antibodies produced by hybridomas and antibodies produced by host cells transformed with an expression vector carrying an antibody gene by genetic engineering techniques.

There is no particular limitation on the mammal to be immunized for obtaining antibodies. It is preferable to select the mammal by considering its compatibility with the parent cells to be used in cell fusion for hybridoma production. In general, rabbits, monkeys, and rodents such as mice, rats, and hamsters are suitably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with Phosphate-Buffered Saline (PBS), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein; and there is no need to purify the antigen for immunization.

In order to prepare a monoclonal antibody using DNA immunization, first, a DNA expressing an antigen protein is administered to an animal to be immunized. The antigen protein-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized.

After immunizing a mammal as described above, an increase in the titer of an antigen-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978) 81, 1-7);

NS-1 (C. Eur. J. Immunol. (1976) 6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be arbitrarily set, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) prewarmed to about 37° C. is added thereto at a concentration of generally 30% to 60% (w/v). The mixed solution is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Culture is continued in the above medium using the HAT medium for a period of time sufficient to kill cells other than the desired hybridomas (non-fused cells). Specifically, desired hybridomas can be selected by culture for generally several days to several weeks. Then, hybridomas producing the desired antibody are screened and singly cloned by conventional limiting dilution methods.

Screening and single cloning of desired antibodies can be suitably performed by screening methods based on known antigen-antibody reaction. For example, a desired antibody can be selected by screening using fluorescence activated cell sorting (FACS). FACS is a system that enables measurement of the binding of an antibody to cell surface by analyzing cells contacted with a fluorescent antibody using laser beam, and measuring the fluorescence emitted from individual cells.

To screen for hybridomas that produce a monoclonal antibody by FACS, cells that express the antigen bound by the produced antibody are first prepared. Preferred cells used for screening are mammalian cells that are forced to express the antigen. By using mammalian cells that are used as the host cell but have not been transformed as a control, the activity of an antibody to bind to the cell-surface antigen can be selectively detected. Specifically, hybridomas producing a desired monoclonal antibody can be obtained by selecting hybridomas that produce an antibody which binds to cells forced to express the antigen but not to the host cell.

Alternatively, cells expressing the antigen of interest are immobilized and the activity of an antibody to bind to the antigen-expressing cells can be assessed based on the principle of ELISA. For example, antigen-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium. The hybridomas can be stored in liquid nitrogen for a long period.

The above hybridomas are cultured by a conventional method, and desired monoclonal antibodies can be obtained from the culture supernatants. Alternatively, the hybridomas are administered to and grown in compatible mammals, and monoclonal antibodies can be obtained from the ascites. The former method is suitable for obtaining antibodies with high purity.

Antibodies that are encoded by antibody genes cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

Generally, to obtain a cDNA encoding the antibody variable region (V region), total RNA is first extracted from hybridomas. For example, the following methods can be used as methods for extracting mRNAs from cells:

the guanidine ultracentrifugation method (Biochemistry (1979) 18(24), 5294-5299), and the AGPC method (Anal. Biochem. (1987) 162(1), 156-159).

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Corporation) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into $E. coli$ or such. After colony selection, the desired recombinant vector can be prepared from the colony-forming $E. coli$. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

Immunoglobulins composed of a combination of heavy and light chains may be reshaped using the thus amplified PCR products. A desired antibody can be selected by screening using the antigen-binding activity of a reshaped immunoglobulin as an indicator. The screening can be carried out, for example, by the following steps:

(1) contacting a desired antigen-expressing cell with an antibody comprising the V region encoded by a cDNA obtained from a hybridoma;

(2) detecting the binding of the antibody to the antigen-expressing cell; and (3) selecting an antibody that binds to the antigen-expressing cell.

Methods for detecting the binding of an antibody to the antigen-expressing cells are known. Specifically, the binding of an antibody to the antigen-expressing cells can be detected by the above-described techniques such as FACS.

Fixed samples of the antigen-expressing cells may be appropriately used to assess the binding activity of an antibody.

For antibody screening methods that use the binding activity as an indicator, panning methods that use phage vectors can also be used suitably. Screening methods using phage vectors are advantageous when the antibody genes are obtained from a polyclonal antibody-expressing cell population as heavy-chain and light-chain subclass libraries. Genes encoding the heavy-chain and light-chain variable regions can be linked by an appropriate linker sequence to form a single-chain Fv (scFv). Phages expressing scFv on their surface can be produced by inserting a scFv-encoding gene into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, a "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA that encodes a desired antibody constant region (C region). A chimeric antibody expression vector is constructed by fusing in-frame two genes digested with the same combination of restriction enzymes.

To produce a monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. The signal sequence is cleaved from the carboxyl terminus of the expressed polypeptide, and the resulting antibody can be secreted to the outside of cells. Then, appropriate host cells are transformed with the expression vector, and recombinant cells expressing the antibody-encoding DNA can be obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors inserted with the H chain and L chain. Alternatively, host cells can be transformed with a single expression vector into which DNAs encoding the H and L chains are inserted (see WO 94/11523).

There are many known combinations of host cells and expression vectors for antibody preparation by introducing isolated antibody genes into appropriate hosts. All these expression systems are applicable to isolation and expression of antigen-binding molecules, domains that bind to a molecule expressed on the surface of a cell having immune response-suppressing function, T cell receptor complex-binding domain or such in the present invention.

Appropriate eukaryotic cells used as host cells include animal cells, plant cells, and fungal cells. Specifically, the animal cells include, for example, the following cells:
(1) mammalian cells: CHO, COS, myeloma, baby hamster kidney (BHK), HeLa, Vero, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
yeasts: the *Saccharomyces* genus such as *Saccharomyces cerevisiae*, and the *Pichia* genus such as *Pichia pastoris*; and
filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Bio/Technology (1994) 12 (7), 699-702).

When an antigen-binding molecule described herein is administered to human, an antigen-binding domain derived from a genetically recombinant antibody that has been artificially modified to reduce the heterologous antigenicity against human and such, can be appropriately used as the various binding domains in the molecule when domains comprising an antibody variable region are used. Such genetically recombinant antibodies include, for example, humanized antibodies. These modified antibodies are appropriately produced by known methods.

An antibody variable region used to produce the various binding domains of antigen-binding molecules described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced into another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing a scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the phage display method, techniques that use a cell-free translation system, techniques for displaying antigen-binding molecules on the surface of viruses or cells, and techniques that use emulsions are also known as techniques for obtaining human antibodies by panning using human antibody libraries. For example, the ribosome display method where a complex is formed between the translated protein and mRNA via the ribosome by removing the stop codon and such, the cDNA display method or the mRNA display method where a genetic sequence and the translated protein are covalently linked using a compound such as puromycin, the CIS display method where a complex is formed between the gene and the translated protein using a nucleic acid-binding protein, or such may be used as techniques of using a cell-free translation system. For the technique of presenting antigen-binding molecules on the surface of cells or viruses, besides the phage display method, the *E. coli* display method, Gram-positive bacteria display method, yeast display method, mammalian cell display method, virus display method, and such may be used. As a technique that uses emulsions, the in vitro virus display method which involves incorporating genes and translation-related molecules into an emulsion, and such may be used. These methods are already publicly known (Nat Biotechnol. 2000 December; 18(12):1287-92; Nucleic Acids Res. 2006; 34(19): e127; Proc Natl Acad Sci USA. 2004 Mar. 2; 101(9):2806-10; Proc Natl Acad Sci USA. 2004 Jun. 22; 101(25):9193-8; Protein Eng Des Sel. 2008 April; 21(4): 247-55; Proc Natl Acad Sci USA. 2000 Sep. 26; 97(20): 10701-5; MAbs. 2010 September-October; 2(5):508-18; and Methods Mol Biol. 2012, 911:183-98).

In the present invention, "specific" means a condition where one of the molecules involved in specific binding does not show any significant binding to molecules other than a single or a number of binding partner molecules. Furthermore, "specific" is also used when an antigen-binding domain is specific to a particular epitope among multiple epitopes contained in an antigen. When an epitope bound by an antigen-binding domain is contained in multiple different antigens, antigen-binding molecules containing the antigen-binding domain can bind to various antigens that have the epitope.

"Epitope" means an antigenic determinant in an antigen, and refers to an antigen site to which various binding domains in antigen-binding molecules disclosed herein bind. Thus, for example, an epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues that form the epitope. Alternatively, when the epitope is a sugar chain, the epitope can be specified by its specific sugar chain structure.

Methods for assaying the binding activity of a test antigen-binding molecule comprising an antigen-binding domain to antigen-expressing cells include, for example, the methods described in Antibodies A Laboratory Manual (Ed Harlow, David Lane, Cold Spring Harbor Laboratory (1988) 359-420). Specifically, the assessment can be performed based on the principle of ELISA or fluorescence activated cell sorting (FACS) using antigen-expressing cells as antigen.

In the ELISA format, the binding activity of a test antigen-binding molecule comprising an antigen-binding domain towards antigen-expressing cells can be assessed quantitatively by comparing the levels of signals generated by enzymatic reaction. Specifically, a test antigen-binding molecule is added to an ELISA plate onto which antigen-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody-binding titer for antigen-expressing cells can be determined to compare the binding activity of the test antigen-binding molecule towards antigen-expressing cells.

The binding of a test antigen-binding molecule to an antigen expressed on the surface of cells suspended in buffer or the like can be detected using a flow cytometer. Known flow cytometers include, for example, the following devices:
FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Suitable methods for assaying the binding activity of the above-mentioned test antigen-binding molecule comprising an antigen-binding domain towards an antigen include, for example, the method below. First, antigen-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the antigen-binding molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to the cells. That is, the binding activity of a test antigen-binding molecule, which is represented by the quantity of the test antigen-binding molecule bound, can be measured by determining the Geometric Mean value.

In the present invention, an "antigen-binding molecule" comprises both heavy and light chains which form an "antibody variable region" within a single polypeptide chain; however, it may be an antibody fragment lacking a constant region. Examples of such antibody fragments include a diabody (Db), an scFv, a single-chain antibody, an sc(Fv)$_2$, and an sc(Fab')$_2$.

Db is a dimer composed of two polypeptide chains (Holliger P et al., Proc. Natl. Acad. Sci. USA 90: 6444-6448 (1993); EP404,097; WO93/11161). In each polypeptide chain, an L-chain variable region (VL) and an H-chain variable region (VH) are linked by a linker short enough so that these two regions on the same chain cannot associate with each other, for example, a linker of about five residues.

Because the linker between VL and VH is too short for formation of a single chain variable region fragment, VL and VH encoded on the same polypeptide chain dimerize to form two antigen-binding sites.

Furthermore, herein, the terms "scFv", "single-chain antibody", and "sc(Fv)$_2$" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)$_2$ is a single-chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)$_2$ preferably includes, for example, a bispecific sc(Fv)$_2$ that recognizes two types of epitopes present in a single antigen as disclosed in the Journal of Immunology (1994) 152(11), 5368-5374. sc(Fv)$_2$ can be produced by methods known to those skilled in the art. For example, sc(Fv)$_2$ can be produced by linking scFv by a linker such as a peptide linker.

Herein, the form of an antigen-binding domain forming an sc(Fv)$_2$ include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Example order of the form is listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)$_2$ is also described in detail in WO2006/132352. According to these descriptions, those skilled in the art can appropriately prepare desired sc(Fv)$_2$ to produce the antigen-binding molecules disclosed herein.

Herein, the term "variable fragment (Fv)" refers to the minimum unit of an antibody-derived antigen-binding domain composed of a pair of the antibody light chain variable region (VL) and antibody heavy chain variable region (VH). In 1988, Skerra and Pluckthun found that homogeneous and active antibodies can be prepared from the E. coli periplasm fraction by inserting an antibody gene downstream of a bacterial signal sequence and inducing expression of the gene in E. coli (Science (1988) 240(4855), 1038-1041). In the Fv prepared from the periplasm fraction, VH associates with VL in a manner so as to bind to an antigen.

Furthermore, the antigen-binding molecule of the present invention may be conjugated with a carrier polymer such as PEG or an organic compound such as an anticancer agent. Alternatively, a glycosylation sequence can be inserted to suitably add a sugar chain for the purpose of producing a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)$_2$ contains three peptide linkers, their length may be all the same or different.

For example, such peptide linkers include:

```
Ser

Gly•Ser

Gly•Gly•Ser

Ser•Gly•Gly (SEQ ID NO: 10)
Gly•Gly•Gly•Ser (SEQ ID NO: 11)
Ser•Gly•Gly•Gly (SEQ ID NO: 12)
Gly•Gly•Gly•Gly•Ser (SEQ ID NO: 13)
Ser•Gly•Gly•Gly•Gly (SEQ ID NO: 14)
Gly•Gly•Gly•Gly•Gly•Ser (SEQ ID NO: 15)
Ser•Gly•Gly•Gly•Gly•Gly (SEQ ID NO: 16)
Gly•Gly•Gly•Gly•Gly•Gly•Ser (SEQ ID NO: 17)
Ser•Gly•Gly•Gly•Gly•Gly•Gly (Gly•Gly•Gly•Gly•Ser (SEQ ID NO: 12))n (Ser•Gly•Gly•Gly•Gly (SEQ ID NO: 13))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:

N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

In general, three linkers are required to link four antibody variable regions together. The linkers to be used may be of the same type or different types.

Furthermore, "Fab" is composed of a single light chain, and a CH1 domain and variable region from a single heavy chain. The heavy chain of Fab molecule cannot form disulfide bonds with another heavy chain molecule.

"F(ab')$_2$" or "Fab'" is produced by treating an immunoglobulin (monoclonal antibody) with a protease such as pepsin and papain, and refers to an antibody fragment generated by digesting an immunoglobulin (monoclonal antibody) at near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CHγ1 (γ1 region in an H-chain constant region) via a disulfide bond at their C-terminal regions. Each of these two homologous antibody fragments is called Fab'.

"F(ab')$_2$" contains two light chains and two heavy chains comprising the constant region of a CH1 domain and a portion of a CH2 domain so that disulfide bonds are formed between the two heavy chains. The F(ab')$_2$ constituting an antigen-binding molecule disclosed herein can be preferably obtained as below. A full-length monoclonal antibody or such comprising a desired antigen-binding domain is partially digested with a protease such as pepsin, and then Fc fragments are removed by adsorption onto a Protein A column. The protease is not particularly limited, as long as it can digest the full-length antibody in a restrictive manner to produce F(ab')$_2$ under an appropriately established enzyme reaction condition such as pH. Such proteases include, for example, pepsin and ficin.

A preferred embodiment of the "antigen-binding molecule" of the present invention includes a multispecific antibody. When using an Fc region with decreased Fcγ receptor-binding activity as the Fc region of a multispecific antibody, an Fc region derived from a multispecific antibody may also be used appropriately. For the multispecific antibodies of the present invention, in particular, bispecific antibodies are preferred.

For association of multispecific antibodies, one can apply the technique of introducing charge repulsion at the interface of the second constant region of the antibody H chain (CH2)

or the third constant region of the H chain (CH3) to suppress undesired associations between H chains (WO2006/106905).

In the technique of suppressing unintended association between H chains by introducing charge repulsion at the interface of CH2 or CH3, examples of the amino acid residues that are contacted at the interface of other constant regions of the H chain include the region facing the residue at position 356 (EU numbering), the residue at position 439 (EU numbering), the residue at position 357 (EU numbering), the residue at position 370 (EU numbering), the residue at position 399 (EU numbering), and the residue at position 409 (EU numbering) in the CH3 region.

More specifically, for example, for an antibody comprising two types of H chain CH3 regions, the antibody can be made so that one to three pairs of amino acid residues selected from the amino acid residue pairs shown below in (1) to (3) in the first H chain CH3 region have the same charge: (1) amino acid residues at positions 356 and 439 (EU numbering) which are amino acid residues contained in the H chain CH3 region; (2) amino acid residues at positions 357 and 370 (EU numbering) which are amino acid residues contained in the H chain CH3 region; and (3) amino acid residues at positions 399 and 409 (EU numbering) which are amino acid residues contained in the H chain CH3 region.

Furthermore, the antibody can be made so that one to three pairs of amino acid residues corresponding to the amino acid residue pairs shown above in (1) to (3) having the same type of charge in the first H chain CH3 region, which are amino acid residue pairs selected from the amino acid residue pairs shown above in (1) to (3) in the second H chain CH3 region which differs from the first H chain CH3 region, have a charge opposite to the corresponding amino acid residues in the aforementioned first H chain CH3 region.

The respective amino acid residues of (1) to (3) mentioned above are positioned close to each other when associated. For the desired H chain CH3 region or H chain constant region, those skilled in the art can find sites corresponding to the above-mentioned amino acid residues of (1) to (3) by homology modeling and such using commercially available software, and amino acid residues of these sites can be subjected to modifications as appropriate.

In the above-mentioned antibodies, "amino acid residues having a charge" are preferably selected, for example, from amino acid residues contained in either one of groups (a) and (b) below:

(a) glutamic acid (E) and aspartic acid (D); and
(b) lysine (K), arginine (R), and histidine (H).

Regarding the above-mentioned antibodies, "having the same type of charge" means, for example, that two or more amino acid residues all have amino acid residues included in either one of the above-mentioned groups (a) and (b). The phrase "having the opposite charge" means that, for example, when at least one of the two or more amino acid residues has an amino acid residue included in either one of the above-mentioned groups (a) and (b), the remaining amino acid residue(s) will have an amino acid residue included in the other group.

In a preferred embodiment of the above-mentioned antibody, the first H chain CH3 region and the second H chain CH3 region may be cross-linked by a disulfide bond.

In the present invention, the amino acid residue to be subjected to alteration is not limited to an amino acid residue of the constant region or variable region of the antibody described above. With regard to polypeptide mutants or heteromultimers, those skilled in the art can find amino acid residues that form the interface through homology modeling and such using commercially available software, and can subject the amino acid residues at those sites to alterations so that association is regulated.

Other known techniques can also be used for the association of multispecific antibodies of the present invention. Polypeptides with different amino acids having an Fc region can be efficiently associated with each other by substituting an amino acid side chain present in one of the H chain variable regions of the antibody with a larger side chain (knob), and substituting an amino acid side chain present in the corresponding variable region of the other H chain with a smaller side chain (hole), to allow placement of the knob within the hole (WO1996/027011; Ridgway J B et al., Protein Engineering (1996) 9, 617-621; Merchant A M et al. Nature Biotechnology (1998) 16, 677-681; and US20130336973).

In addition, other known techniques can also be used to form multispecific antibodies of the present invention. Association of polypeptides having different sequences can be induced efficiently by complementary association of CH3s, using a strand-exchange engineered CH3 domain produced by changing part of CH3 in one of the H chains of an antibody into its corresponding IgA-derived sequence, and introducing into the complementary portion of the CH3 in the other H chain its corresponding IgA-derived sequence (Protein Engineering Design & Selection, 23; 195-202, 2010). This known technique can also be used to efficiently form multispecific antibodies of interest.

In addition, the following techniques and such may be used for the formation of multispecific antibodies: techniques for antibody production using association of antibody CH1 and CL, and association of VH and VL as described in WO 2011/028952, WO2014/018572, and Nat Biotechnol. 2014 February; 32(2):191-8; techniques for producing bispecific antibodies using separately prepared monoclonal antibodies in combination (Fab Arm Exchange) as described in WO2008/119353 and WO2011/131746; techniques for regulating association between antibody heavy chain CH3s as described in WO2012/058768 and WO2013/063702; techniques for producing bispecific antibodies composed of two types of light chains and one type of heavy chain as described in WO2012/023053; techniques for producing bispecific antibodies using two bacterial cell strains that individually express one of the chains of an antibody comprising a single H chain and a single L chain as described by Christoph et al. (Nature Biotechnology Vol. 31, p 753-758 (2013)).

An embodiment of multispecific antibody formation includes methods for obtaining bispecific antibodies by mixing two types of monoclonal antibodies in the presence of a reducing agent to cleave the disulfide bonds in the core hinge region, followed by re-association for heterodimerization (FAE) as described above. Meanwhile, introduction of electrostatic interactions at the interacting interface of the CH3 region (WO2006/106905) can induce even more efficient heterodimerization during the re-association (WO2015/046467). In FAE using naturally-occurring IgG, re-association takes place randomly; and thus theoretically, bispecific antibodies can only be obtained at 50% efficiency; however, in this method, bispecific antibodies can be produced in high yield.

Alternatively, even when a multispecific antibody of interest cannot be formed efficiently, a multispecific antibody of the present invention can be obtained by separating and purifying the multispecific antibody of interest from the produced antibodies. For example, a method has been reported that enables purification of two types of homologous forms and the heterologous antibody of interest by ion exchange chromatography, by conferring a difference in the isoelectric points by introducing amino acid substitutions into the variable regions of the two types of H chains (WO2007114325). To date, as a method for purifying heterologous forms, a method using Protein A to purify a heterodimerized antibody comprising a mouse IgG2a H chain that binds to Protein A and a rat IgG2b H chain that does not bind to Protein A has been reported (WO98050431 and WO95033844). Furthermore, the heterodimerized antibody per se can be purified efficiently using a Protein A column by changing the interaction between each of the H chains and Protein A, by using H chains in which amino acid residues at the IgG-Protein A binding site, positions 435 and 436 (EU numbering), are substituted with amino acids that yield a different binding strength to Protein A such as Tyr, His, or such.

Alternatively, a common L chain that can confer binding ability to a plurality of different H chains can be obtained and used as the common L chain of a multispecific antibody. Efficient expression of a multispecific IgG can be achieved by introducing the genes of such a common L chain and a plurality of different H chains into cells and expressing the IgG (Nature Biotechnology (1998) 16, 677-681). A method for selecting a common L chain that shows strong binding ability to any different H chains can also be used when selecting a common H chain (WO 2004/065611).

Furthermore, an Fc region whose C-terminal heterogeneity has been improved can be appropriately used as an Fc region of the present invention. More specifically, Fc regions lacking glycine at position 446 and lysine at position 447, as specified by EU numbering, in the amino acid sequences of two polypeptides constituting an Fc region derived from IgG1, IgG2, IgG3, or IgG4, are provided.

A plurality, such as two or more, of these techniques can be used in combination. Furthermore, these techniques can be appropriately and separately applied to the two H chains to be associated. Furthermore, these techniques can be used in combination with the above-mentioned Fc region of which Fcγ receptor-binding activity has been decreased. Furthermore, an antigen-binding molecule of the present invention may be a molecule produced separately based on an antigen-binding molecule subjected to the above-described modifications so as to have the same amino acid sequence.

Herein, unless a limitation referring to a numerical amount such as "a single" or "multiple" is recited to describe a term, the terms of this description are not interpreted as being particularly limited in numerical quantity, and are understood to be the terms with a meaning of "one or a plurality of".

Those skilled in the art will naturally understand that optional combinations of one or more of the embodiments described herein are included in the present invention, as long as they are not technically inconsistent based on common technical knowledge of those skilled in the art.

All prior art references cited herein are incorporated by reference into this description.

EXAMPLES

Herein below, the present invention will be specifically described with reference to the Examples, but the present invention is not to be construed as being limited to the following Examples.

Example 1: Production of Human CD3 Gene-Substituted Mice (1) Construction of a Mouse Cd3 Gene Region Modification Vector (FIG. 1A)

A bacterial artificial chromosome (BAC) clone was used, into which a genomic region where the mouse CD3ε, CD3δ, and CD3γ genes are positioned had been cloned. A loxP sequence was inserted at the position approximately 3.5 kb 5' upstream of the gene region encoding mouse Cd3ε in this BAC, and the genome region further upstream was removed leaving approximately 3.1 kb. At that time, the loxP sequence was introduced together with neomycin-resistance (neo) gene cassette and insertion was conducted by homologous recombination using a Red/ET system (GeneBridges). In that case, from among the *Escherichia coli* clones that grew in a kanamycin-supplemented medium, clones for which polymerase chain reaction (PCR) method resulted in correct amplification were selected. Next, loxP sequence and Rox sequences were placed at 3' downstream of the Cd3γ gene on the BAC. More specifically, the loxP sequence and Rox sequences were introduced along with hygromycin-resistance (Hyg) gene cassette, and insertion was conducted by homologous recombination using a Red/ET system. In that case, from among the *Escherichia coli* clones that grew in a hygromycin-supplemented medium, clones in which the loxP sequence and Rox sequences were inserted as expected were selected by PCR method. Next, the genomic region 3' downstream of the Hyg gene cassette was removed leaving approximately 3.4 kb.

(2) Introduction of a Mouse Cd3 Gene Region Modification Vector into Mouse Embryonic Stem Cells (ES Cells) (FIG. 1A)

The above-mentioned mouse Cd3 gene region modification vector was introduced into mouse ES cells (C57BL/6N mouse-derived cells) via electroporation, and after selective culturing with G418, drug-resistant clones were obtained. From these clones, screening for homologous recombinants was performed by a PCR method. For electroporation, 60 μg of the mouse Cd3 gene region modification vector was linearized with NotI or the NotI-untreated circular vector was extracted with phenol/chloroform, precipitated with ethanol, and then dissolved in PBS.

ES cells used in screening were cultured on a 96-well plate and washed twice using 200 μl of PBS solution per well. Then, the cells were treated at 55° C. for two hours after adding a cell lysis buffer having the following composition (5 μl of 10×LA buffer II (TAKARA LA for Taq), 5 μl of 25 mM MgCl$_2$, 5 μl of 5% NP-40, 2 μl of proteinase K (TAKARA, 20 mg/ml), and 33 μl of distilled water), and subsequently treated at 95° C. for 15 minutes to inactivate proteinase K, to thereby serve as PCR samples.

The PCR reaction mixture was made up of 1 μl of the sample, 2.5 μl of 10×LA buffer II, 2.5 μl of 25 mM MgCl$_2$, 4 μl of dNTP (2.5 mM), 0.1 μl each of the primers (50 μM each), 0.25 μl of LA Taq (TAKARA), and 14.55 μl of distilled water (25 μl in total). The PCR conditions included preheating at 94° C. for two minutes, 35 cycles of an amplification cycle of 98° C. for ten seconds and 68° C. for 4 minutes 30 seconds, and additional heating at 68° C. for five minutes.

Figure 2:
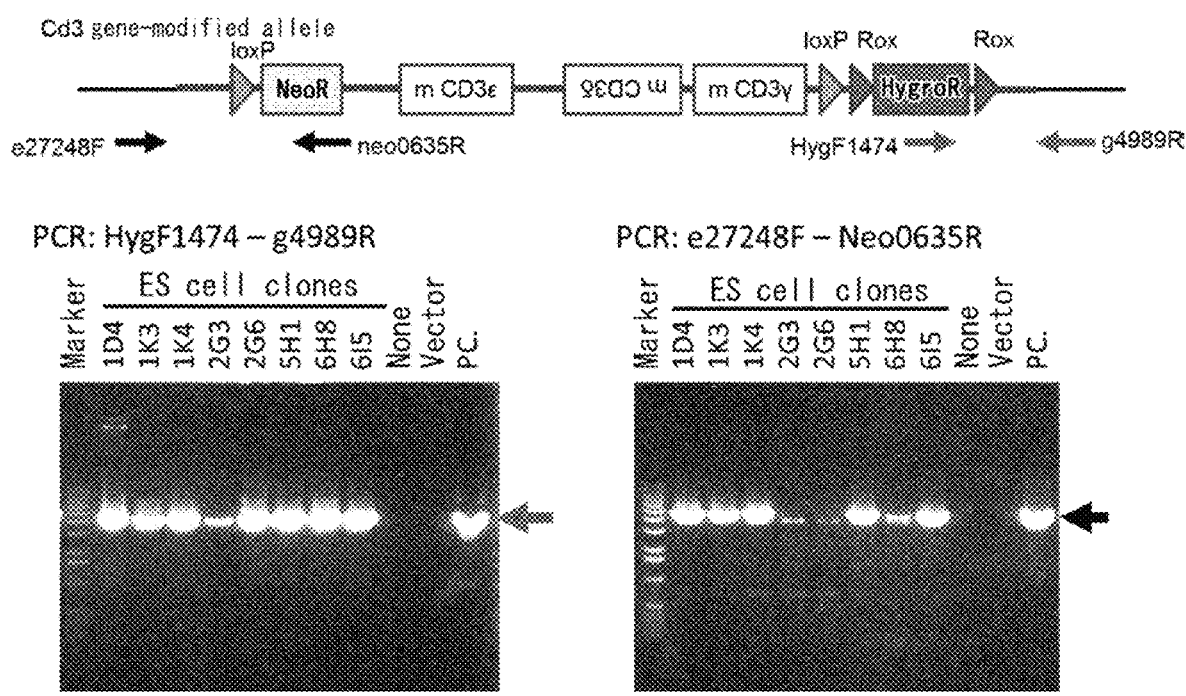
FIG. 2 presents the representative examples of PCR analyses performed for establishing mouse Cd3 gene-modified ES cells.

The following primers were used. The primers were HygF1474 which was positioned within the Hyg gene cassette as a forward primer, and g4989R which was positioned as a reverse primer at the mouse genomic region on the 3' downstream side of the 3' homology arm in the mouse Cd3 gene modification vector (see FIG. 2). In samples of the ES cells in which homologous recombination occurred, an approximately 4-kb band was amplified. HygF1474 (forward) 5'-TATCAGAGCTTGGTTGACGG-3' (SEQ ID NO: 18); and g4989R (reverse) 5'-ACTCGTTGTGGCT-TAGAAG CAGTAACAATACC-3' (SEQ ID NO: 19). Furthermore, clones from which amplification signals were obtained using the above-mentioned primer set were subjected to validation using a different primer set. More specifically, e27248F was positioned as a forward primer at the mouse genomic region on the 5' upstream side of the 5' homology arm in the mouse Cd3 gene modification vector, and Neo0635R was positioned as a reverse primer within the Neo gene cassette. In samples of ES cells in which homologous recombination occurred, an approximately 4-kb band was amplified. e27248F (forward) 5'-ACTGTAATCCTAGTACTTAGGAGGC TGAGG-3' (SEQ ID NO: 20); and Neo0635R (reverse) 5'-AATC-CATCTTGTTCAA TGGCCGATCC-3' (SEQ ID NO: 21).

Figure 1B:
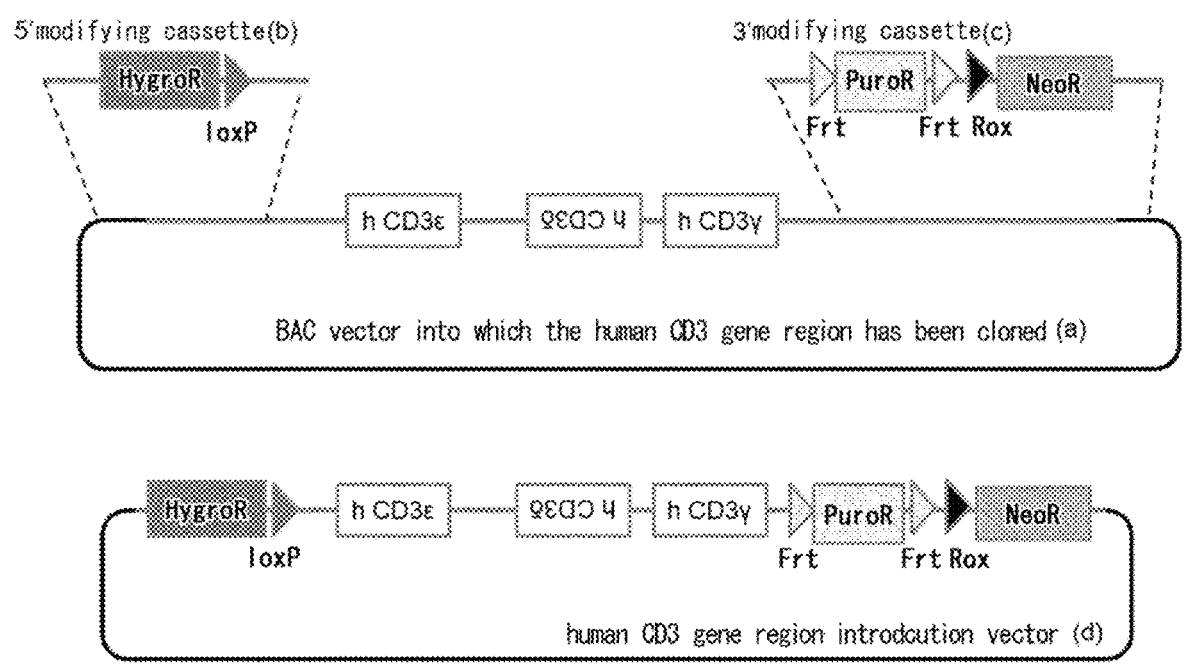
FIG. 1B presents the structures of a BAC clone containing human CD3ε, CD3δ, and CD3γ genes (a); 5'-modifying cassette (b) and 3'-modifying cassette (c), both of which are for modifying the BAC clone; and a human CD3 gene region introduction vector constructed through modifications using those above (d).

(3) Construction of a Human CD3 Gene Region Introduction Vector (FIG. 1B)

A BAC clone was used, into which a genomic region where the human CD3ε, CD3δ, and CD3γ genes are positioned had been cloned. A loxP sequence was inserted at 5' upstream of the gene region encoding human CD3ε in this BAC. At that time, the loxP sequence was introduced along with Hyg gene cassette, and insertion was conducted by homologous recombination using a Red/ET system (GeneBridges). In that case, from among the *Escherichia coli* clones that grew in a hygromycin-supplemented medium, clones for which PCR method resulted in correct amplification were selected. Next, at 3' downstream of the human CD3γ gene in the BAC, puromycin-resistance (Puro) gene flanked on both ends by Frt sequences was introduced together with Neo gene cassette to position a Rox sequence further downstream, and insertion was conducted by homologous recombination using a Red/ET system. In that case, from among the *Escherichia coli* clones that grew in a kanamycin-supplemented medium, clones in which the Frt sequences, the Puro gene, the Rox sequence, and the Neo gene were inserted as expected were selected by PCR method.

(4) Introduction of a Human CD3 Gene Region Introduction Vector and a Recombinase Expression Vector into Cd3 Gene Region-Modified Mouse ES Cells The human CD3 gene region introduction vector, a Cre recombinase expression vector, and a Dre recombinase expression vector were introduced via electroporation into ES cell clones (1D4, 5H1, 615, and 3A5) in which the loxP sequences and Rox sequences were correctly inserted at the targeted sites of the mouse Cd3 gene region in the above-mentioned step; and after selective culturing with puromycin, the grown ES cell clones were genotyped.

First, PCR screening was performed for selection of clones in which recombination between the loxP sequences and between the Rox sequences placed at the mouse Cd3 gene region took place by the action of Cre and Dre, and the genomic region from Cd3ε to Cd3γ was deleted. The ES cells used in screening were cultured on a 96-well plate, washed twice using 200 μl of PBS per well, and treated at 55° C. for two hours after adding a cell lysis buffer having the following composition (5 μl of 10×LA buffer II (TAKARA LA for Taq), 5 μl of 25 mM MgCl₂, 5 μl of 5% NP-40, 2 μl of proteinase K (TAKARA, 20 mg/mL), and 33 μl of distilled water), and subsequently treated at 95° C. for 15 minutes to inactivate proteinase K, to thereby serve as PCR samples.

Figure 3A:
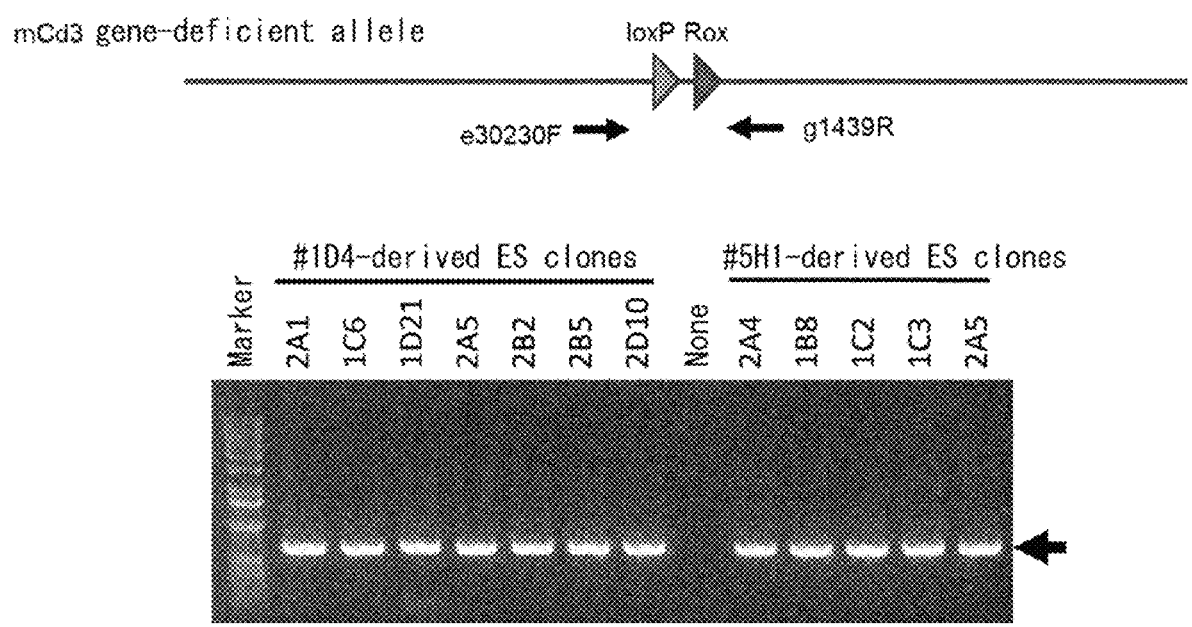
FIG. 3A presents the representative examples of PCR analyses of genotypes of ES cell clones obtained by introducing into mouse Cd3 gene-modified ES cells the human CD3 gene region introduction vector along with a Cre expression vector and a Dre expression vector.

The PCR reaction mixture was made up of 1 μl of the sample, 2.5 μl of 10×LA buffer II, 2.5 μl of 25 mM MgCl₂, 4 μl of dNTP (2.5 mM), 0.1 μl each of the primers (50 μM each), 0.25 μl of LA Taq (TAKARA), and 14.55 μl of distilled water (25 μl in total). The PCR conditions included preheating at 94° C. for two minutes, 35 cycles of an amplification cycle of 98° C. for ten seconds and 68° C. for 4 minutes 30 seconds, and additional heating at 68° C. for five minutes. The following primers were used. The primers were e30230F which was positioned as a forward primer at the genomic region on the 5' upstream side of the mouse Cd3ε gene, and g1439R which was positioned as a reverse primer at the genomic region on the 3' downstream side of the mouse Cd3γ gene (see FIG. 3A). In samples of the ES cells in which the Cd3 gene region was deleted, an approximately 0.7-kb band was amplified. e30230F (forward) 5'-TAGCAGCCTTCA GATGAAGAGGTAGGACTC-3' (SEQ ID NO: 22); and g1439R (reverse) 5'-TTGATG TGC-CACCTCACTGCTGCACTGG-3' (SEQ ID NO: 23).

Figure 3B:
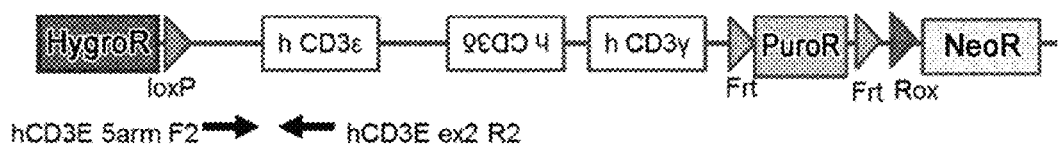
FIG. 3B presents the representative examples of PCR results that detect the introduction of the human CD3 gene region.
Figure 3B:
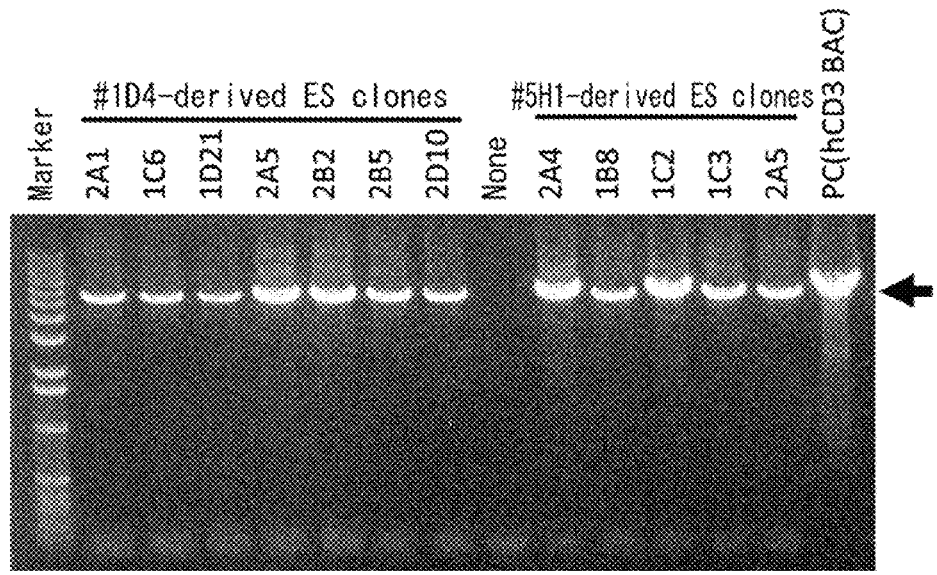

PCR screening was performed for selecting clones in which the human CD3 gene region was introduced from the ES cell clones deficient in the mouse Cd3 gene region. The PCR samples that were used for detecting the deletion of the mouse Cd3 gene region were subjected to the screening. The PCR reaction mixture was made up of 1 μl of the sample, 2.5 μl of 10×LA buffer II, 2.5 μl of 25 mM MgCl₂, 4 μl of dNTP (2.5 mM), 0.1 μl each of the primers (50 μM each), 0.25 μl of LA Taq (TAKARA), and 14.55 μl of distilled water (25 μL in total). The PCR conditions included preheating at 94° C. for two minutes, 35 cycles of an amplification cycle of 94° C. for 30 seconds, 58° C. for one minute, and 72° C. for five minutes, and additional heating at 72° C. for five minutes. The following primers were used. The primers were hCD3e_5arm_F2 which was positioned as a forward primer at the genomic region on the 5' upstream side of the human CD3ε gene, and hCD3e_ex2_R2 which was positioned as a reverse primer within the second exon of the human CD3ε gene (see FIG. 3B). In samples of the ES cells in which the human CD3 gene region was introduced, an approximately 5.5-kb band was amplified. hCD3e_5arm_F2 (forward) 5'-AACTGACAATGGGACATCAGCTGA-3' (SEQ ID NO: 24); and hCD3e_ex2_R2 (reverse) 5'-ATGGGACTGT-TACTTTACTAAGAT-3' (SEQ ID NO: 25).

(5) Production of Mouse Cd3 Gene-Deficient and Human CD3 Gene-Introduced Mice

The homologous recombinant ES clones were suspended by trypsin treatment, and washed with the ES cell medium. Female BALB/c mice which were subjected to superovulation treatment by administering 5 IU of equine chorionic gonadotropin (eCG) and human chorionic gonadotropin (hCG) intraperitoneally at 48-hour intervals were crossed with male mice of the same strain. The day when a plug was confirmed in a female mouse was regarded as day 0.5. On gestation day 3.5, blastocyst-stage embryos collected by perfusing the uterus were used as host embryos, in which 10 to 15 of the ES cells were injected. The embryos after the injection were transferred into the uterus of ICR recipient females on Day 2.5 pseudopregnancy, and their offspring were obtained 17 days later. Screening based on the coat color of the offspring obtained by injection of the ES cells to the blastocysts, yielded chimeric mice having a mixture of the recombinant ES cells (black) and the host blastocyst-derived cells (albino). After sexual maturation, the male chimeric mice were crossed with C57BL/6N-female mice, and transmission of the knock-in allele to the next generation was confirmed by a PCR method using the genomic DNA extracted from the tissues of the second-generation mice as the template. PCR was performed by the above-mentioned method used for screening of the ES cells. As a result, individuals from which the human CD3 gene region-specific 5.5-kb signal and the mouse Cd3 gene region deficiency-specific 0.7-kb signal were detected were obtained, and the human CD3 gene region allele and the mouse Cd3 gene region-deficient allele were confirmed to be transmitted to these individuals. Furthermore, breeding of mice having the above-described genotype yielded mouse individuals whose mouse Cd3 gene region is homozygously deleted and which have the human CD3 gene region, that is, human CD3 gene region-substituted mice were obtained. Transgenic mice in which human CD39ε alone had been introduced (hereinafter, hCD3εTg mice) were produced according to the report by Wang et al. (Non-patent Document 8), and they were examined as comparisons in the later experiments.

(6) Thymus Weights and Spleen Weights of Human CD3 Gene-Substituted Mice

Figure 4:
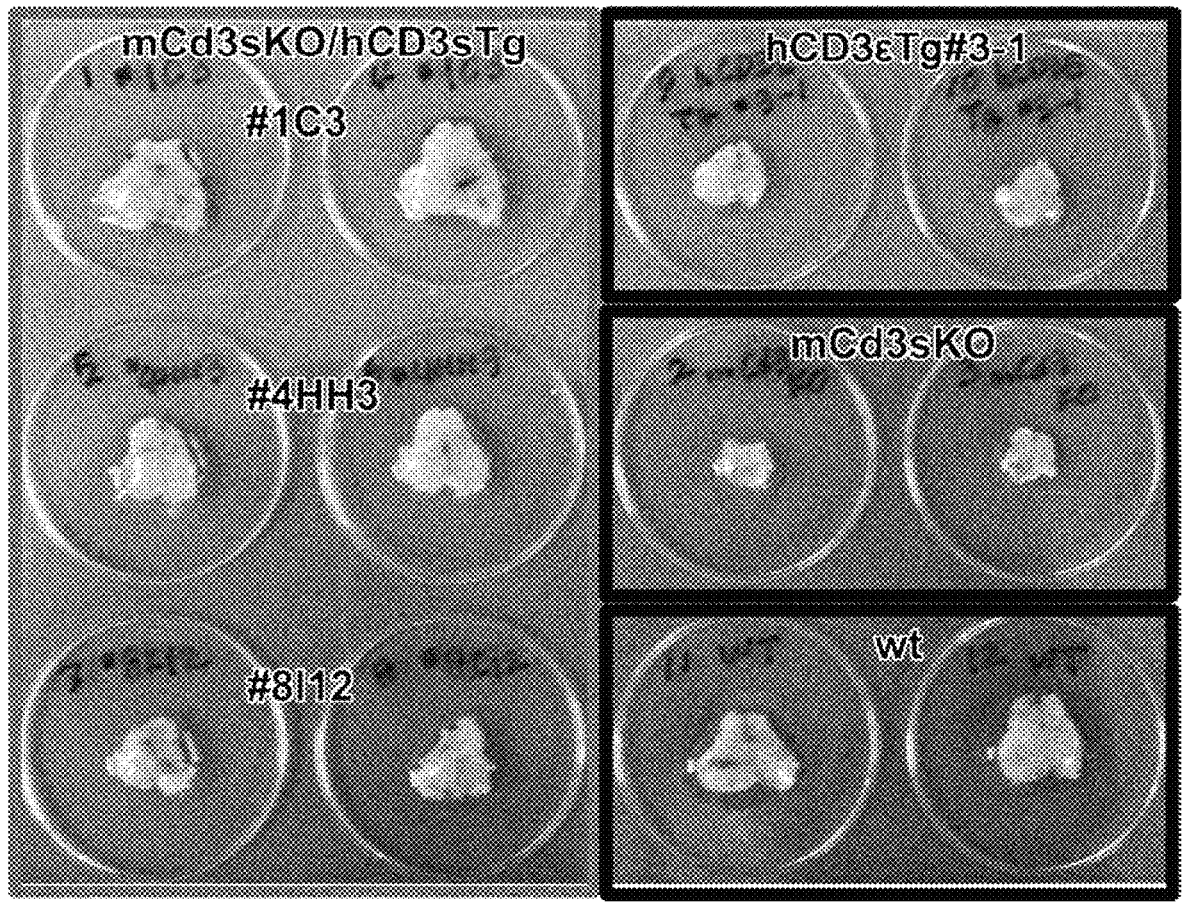
FIG. 4 presents the representative macroscopic photographs of thymuses collected from each of the established lines of human CD3 gene-substituted mice, Cd3 gene-deficient mice, wild type, and human CD3ε gene-introduced mice. Thymuses extirpated from 12 to 13-week-old males are shown for the respective genotypes.
Figure 5:
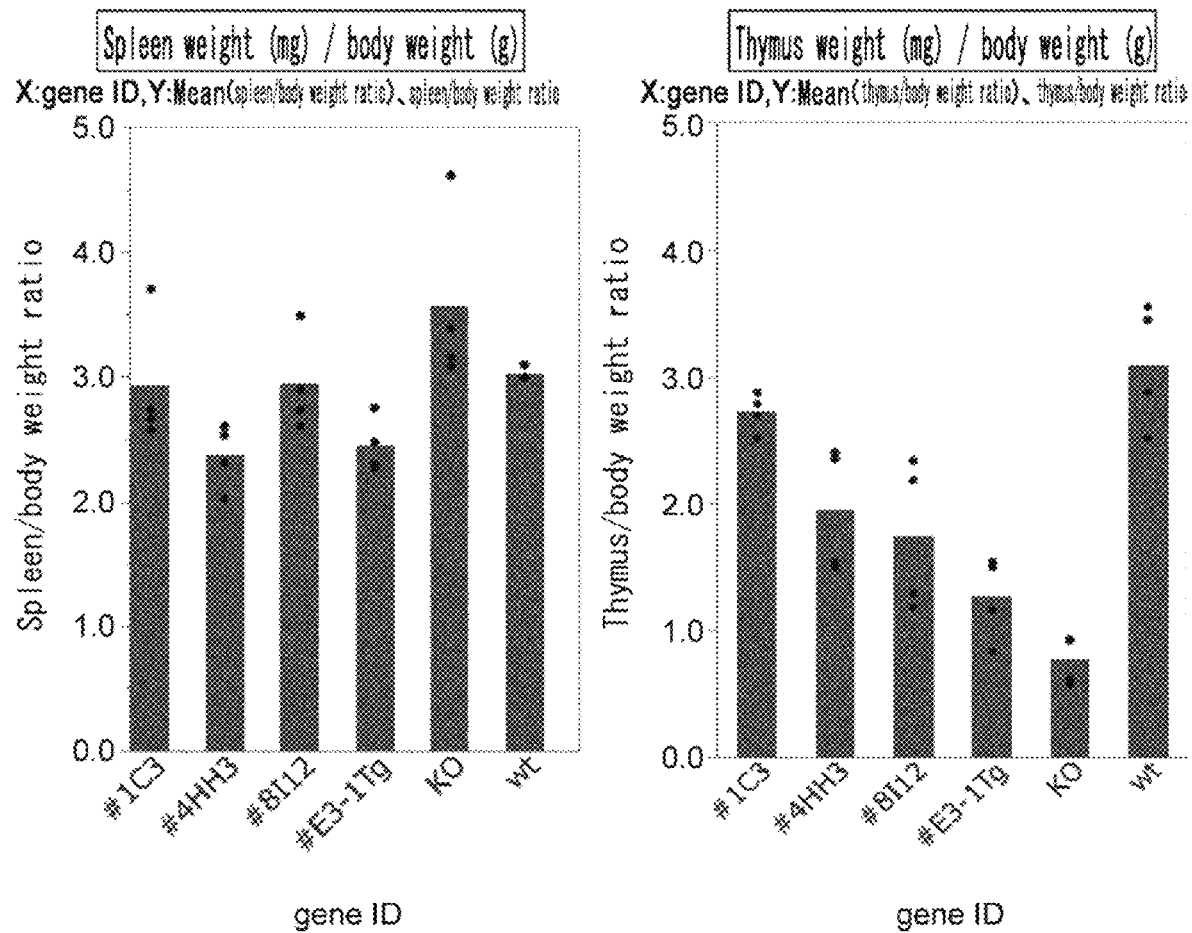
FIG. 5 presents the results of measuring the tissue weights of the spleens and thymuses collected from each of the established lines of human CD3 gene-substituted mice, Cd3 gene-deficient mice, wild-type, and human CD3ε gene-introduced mice. Ratios of tissue weight per body weight were calculated, and the value obtained for each individual is plotted by a black dot and the mean values are shown by columns.

Spleen and thymus were collected from mice (12 to 14-week old, male) and the tissue weights were measured. As shown in FIG. 4, the thymus of the human CD3-substituted mice did not show gross abnormalities. Tissue weight per body weight was calculated for analysis. The body weights and tissue weights (spleen and thymus) were measured for four male mice in each group, and represented as graphs. The tissue weight per body weight ratios were calculated, the values obtained for each individual are plotted by a black dot, and the mean value is shown by a column (FIG. 5). Regarding spleen weight, increasing trend was observed in the Cd3 gene-deficient mice as compared to mice of other genotypes, but no remarkable differences were observed. On the other hand, regarding thymus weight, the Cd3 gene-deficient mice showed decrease down to one third or so as compared to that of the wild-type. In the human CD3 gene-substituted mice produced by introducing a human CD3 gene into the Cd3 gene-deficient mice, recovery of thymus weight was observed, and particularly in the individuals of line no. 1C3, thymus weight was recovered even to the level equivalent to that of the wild-type mice. As reported by Wang et al., thymic atrophy was observed in hCD3εTg mice (Non-patent Document 8).

(7) Confirmation of Expressions of Human CD3 and Mouse Cd3 in the Respective Lines of Human CD3 Gene-Substituted Mice —Confirmation by RT-PCR method using hemocyte RNA—

Expressions of human CD3ε, human CD3δ, human CD3γ, mouse Cd3ε, mouse Cd3δ, and mouse Cd3γ were analyzed by RT-PCR using hemocyte RNA. Using a Catrimox-14 RNA Isolation Kit (TaKaRa Bio), total RNA was prepared from blood collected from the dorsal metatarsal vein or the abdominal vena cava. A 1 μg portion each of the total RNAs was used as a template to synthesize cDNAs by performing reverse transcription reactions with a SuperScript III First Strand cDNA Synthesis Kit (Invitrogen) using Oligo dT (20) primers. Human CD3ε, human CD3δ, human CD3γ, mouse Cd3ε, mouse Cd3δ, and mouse Cd3γ were detected by performing PCR using the synthesized cDNAs as templates. Primers for the protein coding regions were designed to detect the expression of all of the genes. Human CD3ε was detected using the combination of forward primer E0333F (5'-AAGAAATGGGTGGTATTACACAGA CACC-3' (SEQ ID NO: 26)) and reverse primer E0912R (5'-TGGGCCAGCGGGAGGC AGTGTTCTCCAGAGG-3' (SEQ ID NO: 27)). Human CD3δ was detected using the combination of forward primer D0092F (5'-TAGTTCGGTGACCTGGCTTTATCTA CTGG-3' (SEQ ID NO: 28)) and reverse primer D0685R (5'-ATGGCTGCTTCT AGAAGCCACCAGTCTCAGG-3' (SEQ ID NO: 29)). Human CD3γ was detected using the combination of forward primer G0048F (5'-TGCTC-CACGCTTTTGCCGG AGGACAG-3' (SEQ ID NO: 30)) and reverse primer G0666R (5'-TAGGA GGAGAACACCTGGACTACTC-3' (SEQ ID NO: 31)). On the other hand, mouse Cd3ε was detected using the combination of forward primer e0065F (5'-AGCATTCT GAGAG-GATGCGGTGGAACAC-3' (SEQ ID NO: 32)) and reverse primer e0699R (5'-TGCTCGGAGGGCTG-GATCTGGGTCCACAG-3' (SEQ ID NO: 33)). Mouse Cd3δ was detected using the combination of forward primer d055F (5'-TCATCCTGTGG CTTGCCTCTATTTGTTGC-3' (SEQ ID NO: 34)) and reverse primer d651R (5'-TTGCT ATGGCACTTTGAGAAACCTCCATC-3' (SEQ ID NO: 35)). Mouse Cd3γ was detected using the combination of forward primer g080F (5'-AATACTTCTACTGGAGA AGCAAAGAG-3' (SEQ ID NO: 36)) and reverse primer g316R (5'-TAGTTGCATTTA GAGGACTTATTATGC-3' (SEQ ID NO: 37)).

The composition of the PCR reaction solution (25 μl in total) was made up of 1 μl of the sample, 2.5 μl of 10×Ex buffer, 2 μl of dNTP (2.5 mM), 0.1 μl each of the primers (50 μM each), 0.25 μl of Ex Taq (TAKARA), and 19.05 μl of distilled water. The PCR conditions for human CD3δ, human CD3γ, mouse Cd3δ, and mouse Cd3γ included preheating at 94° C. for two minutes, 35 cycles of an amplification cycle of 94° C. for 30 seconds, 60° C. for 30 seconds, and 72° C. for two minutes, and additional heating at 72° C. for five minutes. For human CD3ε and mouse Cd3ε, the PCR conditions included preheating at 94° C. for two minutes, 40 cycles of an amplification cycle of 94° C. for 30 seconds, 60° C. for 30 seconds, and 72° C. for two minutes, and additional heating at 72° C. for five minutes. PCR primers were designed so that the detected amplification products of human CD3ε, human CD3δ, and human CD3γ will be 580 bp, 594 bp, and 620 bp, respectively, and those of mouse Cd3ε, mouse Cd3δ, and mouse Cd3γ will be 635 bp, 597 bp, and 237 bp, respectively.

Figure 6:
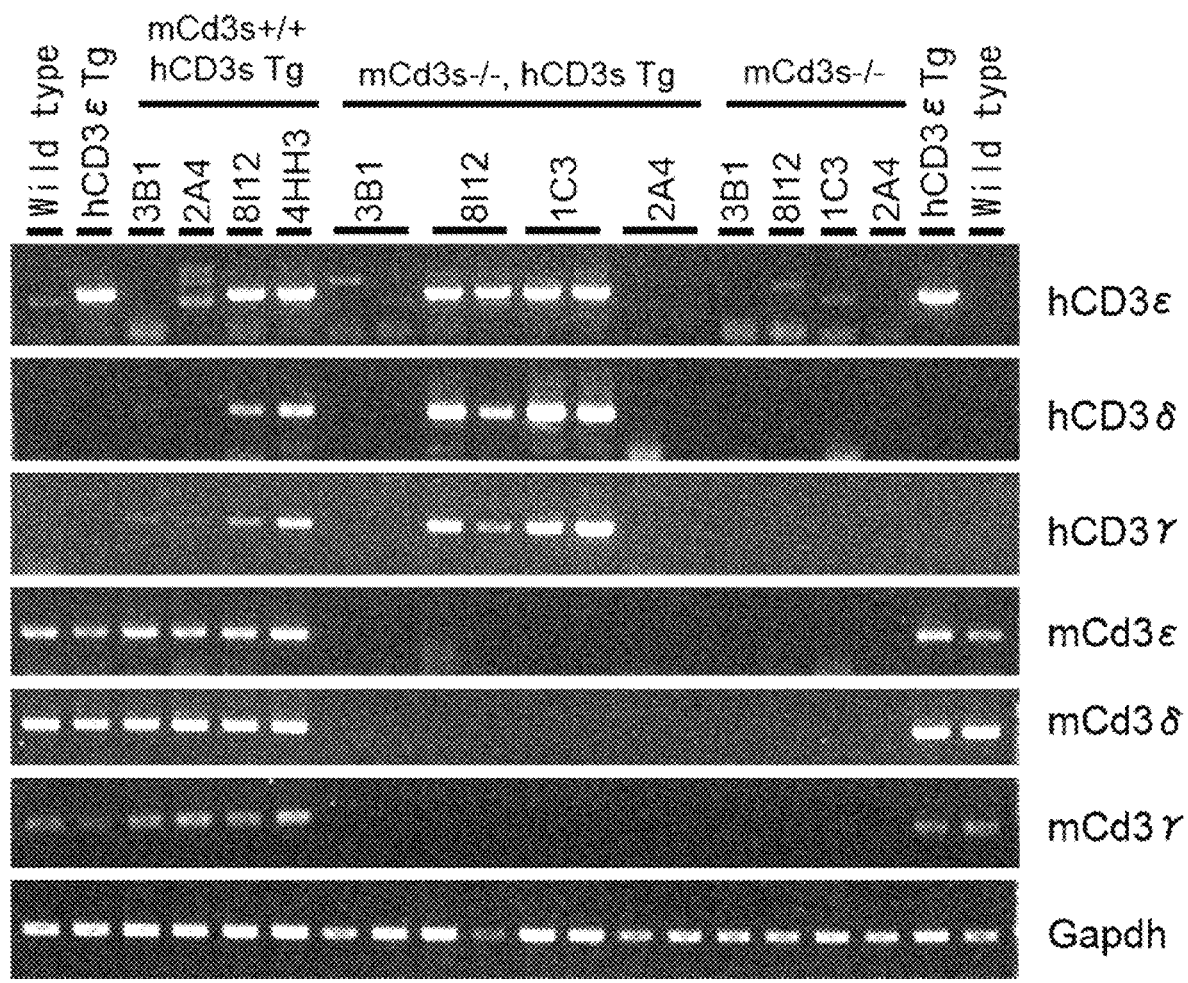
FIG. 6 presents the results of examining by RT-PCR the expressions of each of the human CD3 molecules and each of the mouse Cd3 genes in each of the established lines of human CD3 gene-substituted mice, Cd3 gene-deficient mice, wild-type mice, and human CD3ε gene-introduced (hCD3ε Tg) mice. Among the established lines of the human CD3 gene-substituted mice, signals specific to hCD3ε, hCD3δ, and hCD3γ were detected in line numbers 1C3 and 8I12. The signals were not detected in line numbers 3B1 and 2A4.

In the Cd3 gene-deficient mice, the respective mouse Cd3 molecule-derived PCR signals were not detected. Only human CD3ε, human CD3δ, and human CD3γ were detected, and none of mouse Cd3ε, mouse Cd3δ, and mouse Cd3γ was detected from the samples derived from lines 1C3 and 8112 of the above-mentioned lines among the human CD3 gene-substituted mouse lines (line nos. 1C3, 3B1, 8112, and 2A4) produced by introducing the human CD3 gene region to the Cd3 gene-deficient mice (FIG. 6). From the samples derived from wild-type mice, human CD3ε, human CD3δ, and human CD3γ were not detected, and mouse Cd3ε, mouse Cd3δ, and mouse Cd3γ were detected (FIG. 6). These results confirmed that mice expressing human CD3ε, CD3δ, and CD3γ instead of mouse Cd3ε, Cd3δ, and Cd3γ were obtained as designed. Line 4HH3 in FIG. 6 was analyzed in an individual in which the mouse Cd3 allele is a wild-type and the human CD3 gene has been introduced, and the respective human CD3 molecules and the respective mouse Cd3 molecules are both detected. Subsequently, it was cross-bred with Cd3-deficient mice to establish a mouse Cd3 allele-deficient and human CD3 gene-expressing line.

Analysis by Immunohistological Staining

Figure 7:
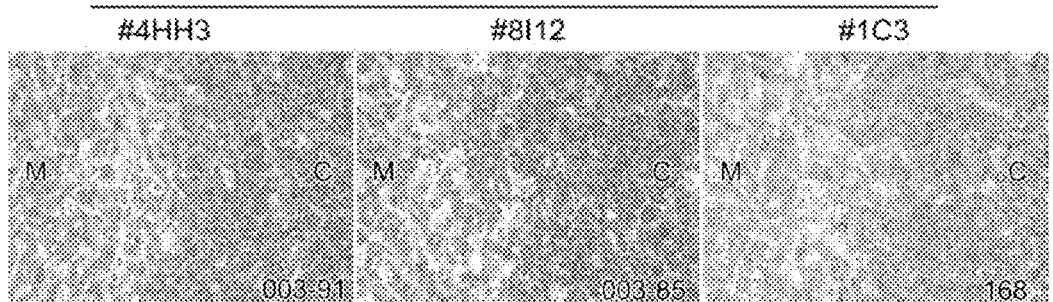
FIG. 7 presents the representative examples of immunohistological staining for CD3 performed on the thymus (A) and spleen (B) of each established line of human CD3 gene-substituted mice (1C3, 8I12, and 4HH3). In both tissues, staining was observed only in the T cell zone as in the wild-type mouse. Furthermore, staining was not observed in the Cd3 gene-deficient mice, and this showed that the staining in the human CD3 gene-substituted mice is due to the expression of the introduced human CD3 genes.
Figure 7:
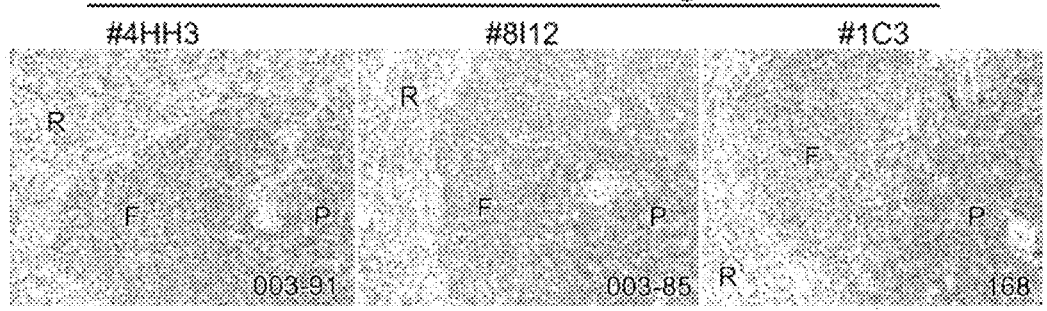
Figure 8:
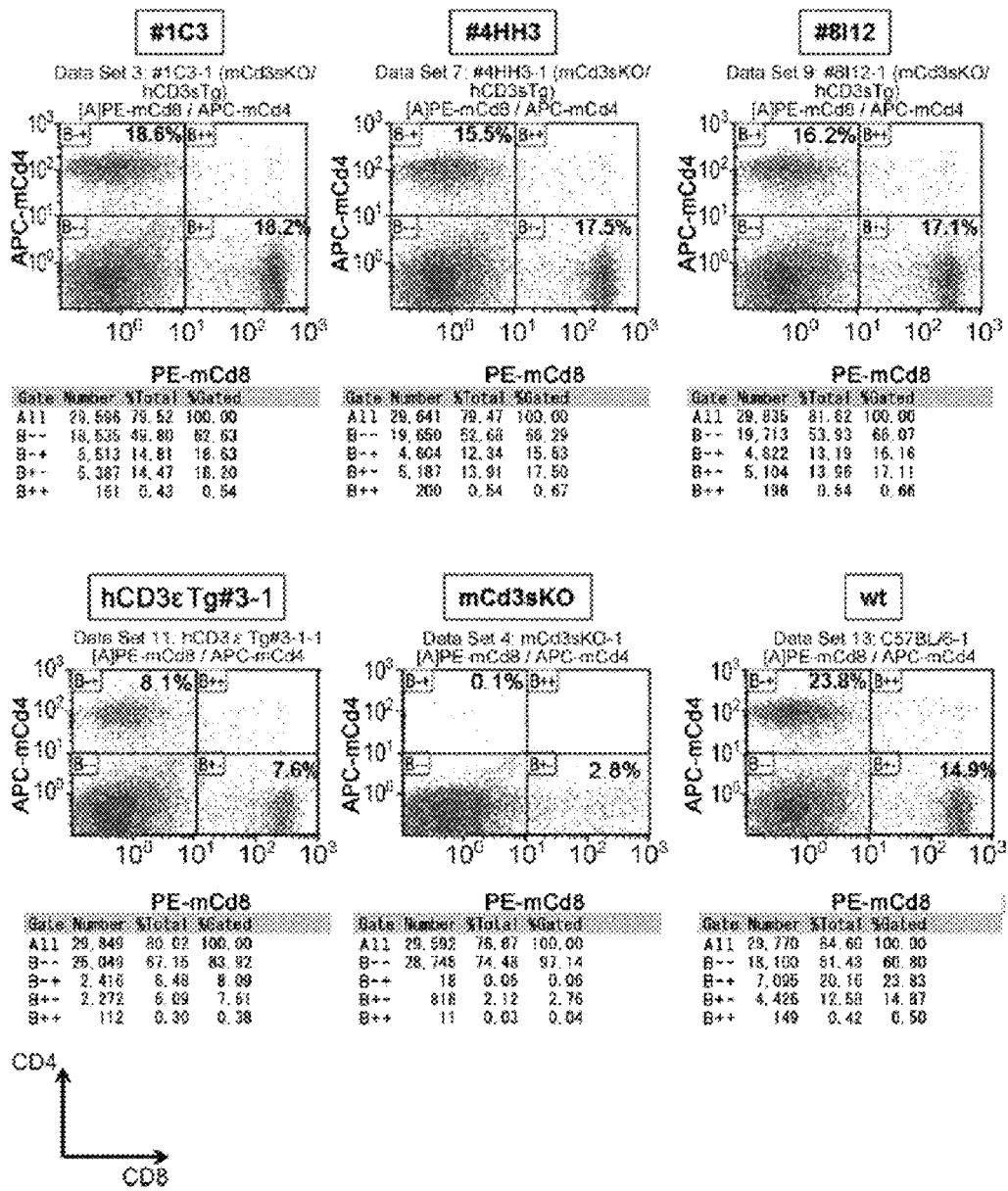
FIG. 8 presents the representative results of analyzing by FACS the abundance ratio of mature T cells in the thymus of each established line of human CD3-substituted mice.

The tissue distribution was examined using the anti-CD3 antibody as the primary antibody. CD3 staining was not observed in any of the tissues from the Cd3-deficient mice, while CD3-specific staining equivalent to that of wild-type mice was observed for the human CD3-substituted mice produced by introducing the human CD3 genes to the Cd3-deficient mice. More specifically, specific staining was observed in the T cell zones in the thymus (FIG. 7A) and spleen (FIG. 7B). In all tissues, staining was observed only in the T cell zone, similarly to the wild-type mice. Furthermore, staining was not observed in the Cd3 gene-deficient mice, indicating that staining in the human CD3 gene-substituted mice was due to the expression of the introduced human CD3 genes. Furthermore, the detection of CD3s in the major organs was the same as in the wild-type, and ectopic staining was not observed (Table 1).

TABLE 1

| Organs | Line | | | | hCD3, mCD3KOTG mouse IACUC 14-074 mCD3ko,hCD3TG | | | | | | hCD3 & TG | | mCD3KO | | | C57BL/6N | | |
|---|---|---|---|---|---|---|---|---|---|---|---|---|---|---|---|---|---|---|
| Findings IHC Staining: CD3 | | #4HH3 | | | #8112 | | | | #1C3 | | #3-1-78 Positive control | | None | | | None | | |
| | Animal No | 008-130 | 010-163 | 003-91 | 003-85 | 003-86 | 001-60 | 168 | 169 | 97 | 195 | #195 790 | 001-63 | 001-64 | 001-67 | B6-01 | B6-02 | B6-03 |
| | Gender | ♀ | ♀ | ♂ | ♂ | ♂ | ♂ | ♀ | ♀ | ♂ | | | ♀ | ♀ | ♂ | ♀ | ♀ | ♂ |
| Date of IHC Staining: A, 2014.6.19; B, 2014.6.25 | | A | A | A | A | A | A | A | A | A | A | A | A | A | A | B | B | B |
| Thymus | | | | | | | | | | | | | | | | | | |
| Atrophy | | + | ± | - | - | ± | - | - | - | - | + | - | ± | ± | ± | - | - | - |
| Lymphocyte, cortex | | ++ | +++ | +++ | +++ | +++ | +++ | +++ | +++ | +++ | +++ | +++ | - | - | - | +++ | +++ | +++ |
| Lymphocyte, medulla | | +++ | +++ | +++ | +++ | +++ | +++ | +++ | +++ | +++ | +++ | - | - | - | - | +++ | +++ | +++ |
| Other tissues | | - | - | - | - | - | - | - | - | - | NA | NA | - | - | - | - | - | - |
| Mesentery | | | | | | | | | | | | | | | | | | |
| Atrophy | | + | + | ± | - | ± | + | - | + | + | + | - | ± | ± | ± | - | - | - |
| Lymphocyte, paracortex | | ++ | ++ | ++ | +++ | +++ | ++ | +++ | ++ | ++ | +++ | +++ | - | - | - | +++ | +++ | +++ |
| Lymphocyte, follicle | | + | + | + | + | + | + | + | + | + | - | + | - | - | - | + | + | + |
| Lymphocyte, medulla | | + | + | + | + | + | + | + | + | + | - | + | - | - | - | - | - | + |
| Other tissues | | - | - | - | - | - | - | - | - | - | NA | NA | - | - | - | - | - | - |
| Ileum | | | | | | | | | | | | | | | | | | |
| Atrophy of GALT | | + | - | - | - | - | - | - | - | - | - | - | ++ | ++ | ++ | - | ++ | - |
| Lymphocyte, GALT | | + | +++ | +++ | ++ | ++ | ++ | ++ | ++ | ++ | ++ | +++ | - | - | - | ++ | ++ | ++ |
| Lymphocyte, lamina propria | | ± | + | + | + | + | + | + | + | + | + | + | - | - | - | + | + | ± |
| Other tissues | | - | - | - | - | - | - | - | - | - | - | - | - | - | - | - | - | - |
| Spleen | | | | | | | | | | | | | | | | | | |
| Atrophy | | ± | - | - | - | - | ± | - | - | - | - | - | + | + | + | - | - | - |
| Lymphocyte, PALS | | +++ | +++ | +++ | +++ | +++ | +++ | +++ | +++ | +++ | + | +++ | - | - | - | +++ | +++ | +++ |
| Lymphocyte, follicle | | + | + | + | + | + | + | + | + | + | ++ | + | - | - | - | + | + | + |
| Lymphocyte, red pulp | | ++ | ++ | ++ | ++ | ++ | ++ | ++ | ++ | ++ | ++ | ++ | - | - | - | ++ | ++ | ++ |
| Other tissues | | - | - | - | - | - | - | - | - | - | - | - | - | - | - | - | - | - |

TABLE 1-continued

| | | | | hCD3, mCD3KOTG mouse IACUC 14-074 | | | | | | | | | | | | | |
|---|---|---|---|---|---|---|---|---|---|---|---|---|---|---|---|---|---|
| | | mCD3ko.hCD3TG | | | | | | | | hCD3 & TG | | mCD3KO | | | C57BL/6N | | |
| | Line | #4HH3 | | | #8112 | | | #1C3 | | #3-1-78 | #195 | | None | | | None | |
| Organs | Animal No | 008-130 | 010-163 | 003-91 | 003-85 | 003-86 | 001-60 | 168 | 169 | 195 | 790 | 001-63 | 001-64 | 001-67 | B6-01 | B6-02 | B6-03 |
| Findings IHC Staining: CD3 | Gender | ♀ | ♀ | ♂ | ♂ | ♂ | ♂ | ♀ | ♀ | ♂ | Positive control | ♀ | ♀ | ♂ | ♀ | ♀ | ♂ |
| Date of IHC Staining: A, 2014.6.19; B, 2014.6.25 | | A | A | A | A | A | A | A | A | A | A | A | A | A | B | B | B |
| Liver | | | | | | | | | | | | | | | | | |
| Lymphocyte, sinusoid | | + | + | + | + | + | + | + | + | + | NA | NA | - | - | - | + | + | + |
| Other tissues | | - | - | - | - | - | - | - | - | - | NA | NA | - | - | - | - | - | - |
| Kidney | | | | | | | | | | | | | | | | | |
| Lymphocyte, interstitium | | ± | ± | ± | ± | ± | ± | ± | ± | ± | NA | NA | - | - | - | ± | ± | ± |
| Other tissues | | - | - | - | - | - | - | - | - | - | NA | NA | - | - | - | - | - | - |
| Adrenal gland | | | | | | | | | | | | | | | | | |
| Lymphocyte, interstitium | | - | - | - | - | - | - | - | - | - | NA | NA | - | - | - | - | - | - |
| Other tissues | | - | - | - | - | - | - | - | - | - | NA | NA | - | - | - | - | - | - |
| Lung | | | | | | | | | | | | | | | | | |
| Lymphocyte, alveolar wall | | ± | ± | ± | ± | ± | ± | ± | ± | ± | NA | NA | - | - | - | ± | ± | ± |
| Other tissues | | - | - | - | - | - | - | - | - | - | NA | NA | - | - | - | - | - | - |
| Heart | | | | | | | | | | | | | | | | | |
| Lymphocyte, interstitium | | - | - | - | - | - | - | - | ± | ± | NA | NA | - | - | - | ± | ± | ± |
| Other tissues | | - | - | - | - | - | - | - | - | - | NA | NA | - | - | - | - | - | - |
| Gastrocnemius muscle | | - | - | - | - | - | - | - | - | - | NA | NA | - | - | - | - | - | - |

Findings: -, negative; ±, very slight; +, slight; ++, moderate; +++, severe
IHC Staining: -, negative; ±, rare; +, occasional; ++, frequent; +++, constant (8) Evaluation of Abundance Ratio of Mature T Cells in Human CD3 Gene-Substituted Mice FACS analyses were performed using spleen cells. Spleens were collected from mice (12 to 14-week old, male), and cells were isolated using 70 μm mesh. Erythrocytes were lysed by adding a hemolytic agent (manufactured by SIGMA). After blocking using an Fc blocking solution, FITC-labeled anti-mouse Cd3 antibody, FITC-labeled anti-human CD3 antibody, APC-labeled anti-mouse Cd4 antibody, and PE-labeled anti-mouse Cd8 antibody were used on $2 \times 10^6$ cells, and the respective positive cell counts were analyzed by a flow cytometer. It was revealed that the Cd3 gene-deficient mice nearly completely lack in mature T cells, that is, Cd4 and Cd8 single positive cells, while these cells were present in the human CD3 gene-substituted mice at a ratio equivalent to that in the wild-type.

Abundance Ratio of Mature T Cells

TABLE 2

| Experimental group | Number of samples | mCd3 | hCD3 | mCd4 | mCd8 |
| --- | --- | --- | --- | --- | --- |
| Human CD3s-substituted mouse #1C3 | n = 4 | ND. | 38.8 (±3.1) | 19.6 (±0.7) | 16.1 (±3.6) |
| Human CD3s-substituted mouse #4HH3 | n = 2 | ND. | 29.8, 28.9 | 15.5, 13.9 | 17.5, 16.4 |
| Human CD3s-substituted mouse #8I12 | n = 4 | ND. | 31.5 (±5.4) | 15.5 (±3.1) | 15.3 (±2.7) |
| hCD3E Tg mouse | n = 4 | 19.5 (±3.76) | 13.0 (±1.4) | 7.4 (±0.6) | 7.8 (±0.8) |
| Cd3s-deficient mouse | n = 4 | ND. | ND. | 1.8 (±1.3) | 2.1 (±0.6) |
| C57BL/6N | n = 4 | 40.4 (±8.42) | ND. | 20.3 (±6.7) | 12.7 (±2.1) |

The table shows the expression ratios of the respective marker-positive cells with respect to the spleen cells (unit %). The mean from four individuals is shown for each the experimental group, except for human CD3s-substituted mice #4HH3, and the expression ratios of two individuals are shown for line #4HH3. (The standard deviation is shown in parenthesis.) ND: not detected.

Figure 9:
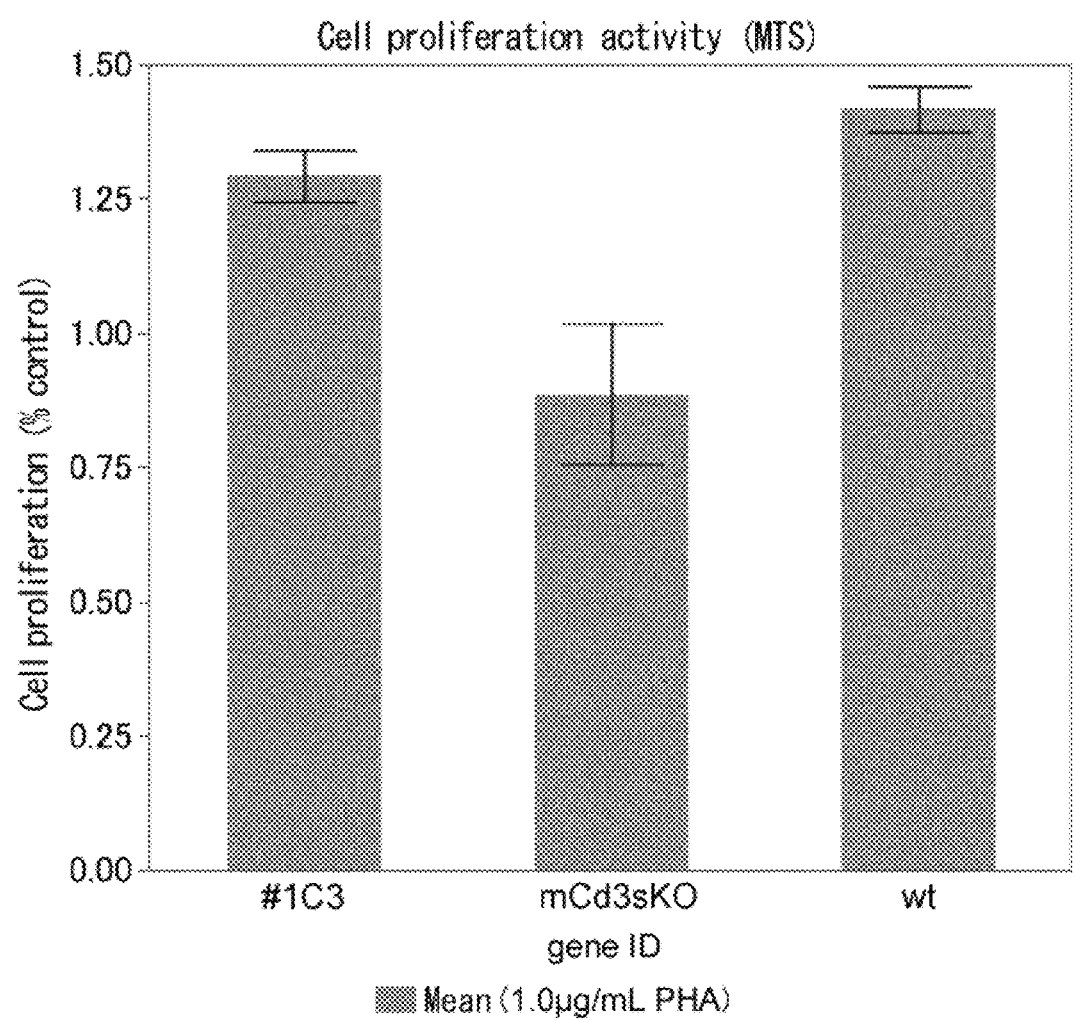
FIG. 9 presents the mitogen-stimulated cell proliferation activities of spleen cells from the human CD3 gene-substituted mice (1C3), Cd3 gene-deficient mice, and wild-type mice. The established human CD3 gene-substituted mice (1C3) showed cell proliferation activity of 90% of the wild type.

Example 2: Evaluation of Cell Proliferation Ability of Spleen Cells in Human Cd3 Gene-Substituted Mice Spleens were collected from mice (12-week old, male), and cells were isolated using 70 μm mesh. Erythrocytes were lysed by adding a hemolytic agent (manufactured by SIGMA). Phytohaemagglutinin (PHA, manufactured by SIGMA) which is a T cell mitogen was added to the isolated spleen cells, and after culturing for five days, MTS assay was carried out using a cell proliferation assay reagent (Cell Titer 96. Aqueous One Solution Reagent, manufactured by Promega). Cell proliferation activities of the respective genotypes are shown as relative proportions by defining the activity without mitogen addition as 1 (FIG. 9).

As a result, in spleen cells of the Cd3 gene-deficient mice, cell proliferation activity in response to mitogen stimulation tended to decrease compared to that when mitogen was not added, and was approximately 60% of that of wild-type mice. On the other hand, in spleen cells of the human CD3 gene-substituted mice and wild-type mice, mitogen stimulation resulted in increase of cell proliferation activities, and the activities in the human CD3 gene-substituted mice were shown to be approximately 90% of that of the wild-type mice.

Figure 10:
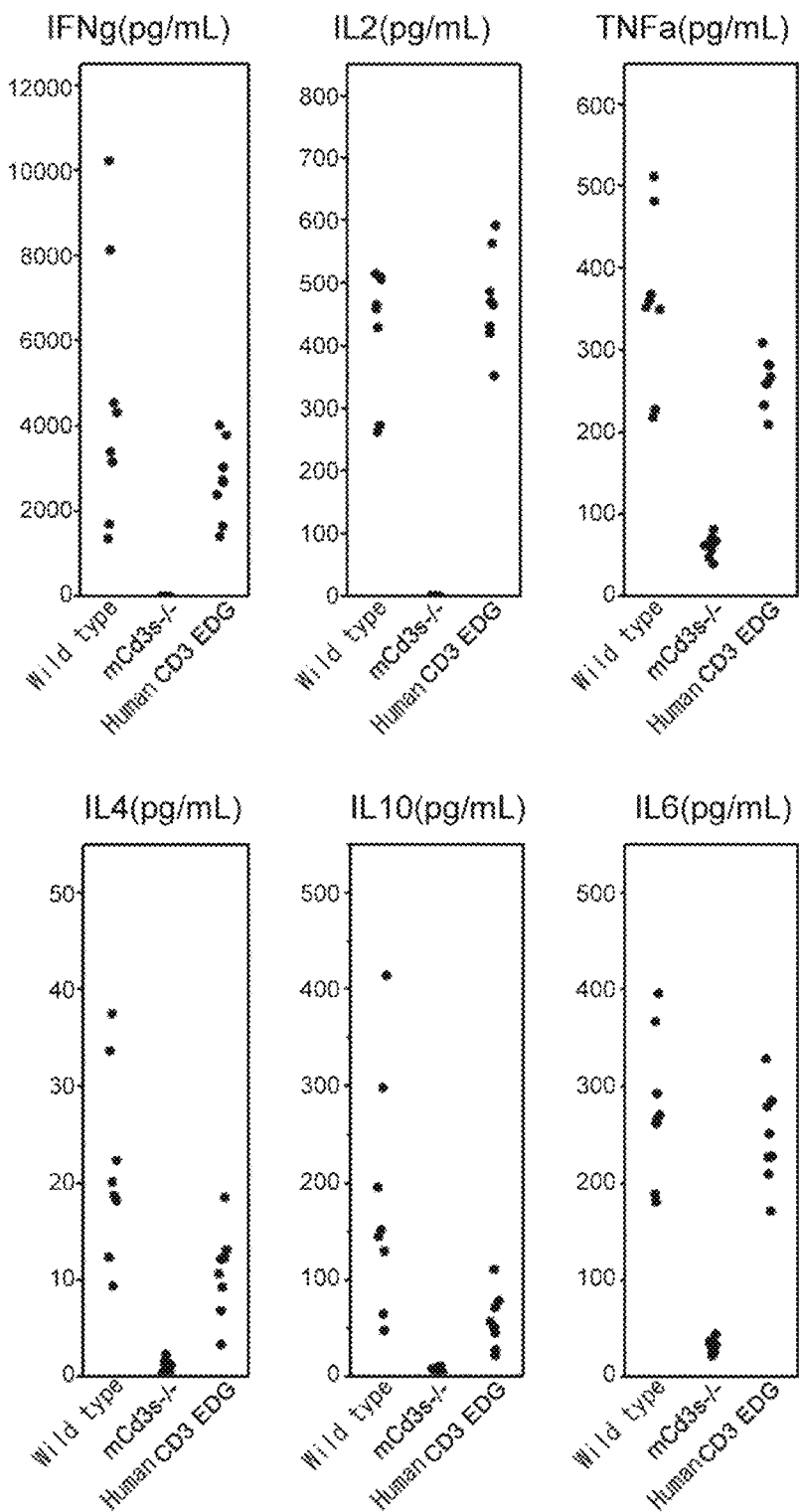
FIG. 10 presents the mitogen-stimulated cytokine production by spleen cells from the human CD3 gene-substituted mice (1C3), Cd3 gene-deficient mice, and wild-type mice. It was shown that cytokine-producing ability that was functionally lost in the Cd3 gene-deficient mice was recovered in the established human CD3 gene-substituted mice (1C3).

Example 3: Evaluation of Cytokine Production in Spleen Cells of Human CD3 Gene-Substituted Mice Spleen cells were prepared by collecting spleens from mice, isolating cells using 70 μm mesh, and lysing erythrocytes by adding a hemolytic agent. After culturing the cells for three days in the medium supplemented with phytohaemagglutinin (PHA) which is a T cell mitogen at a final concentration of 1 μg/mL, cytokines produced in the medium were measured (FIG. 10).

As a result, in spleen cells of the Cd3 gene-deficient mice, mitogen stimulated-cytokine production was not observed, whereas in the human CD3 gene-substituted mice, cytokine production was observed, indicating that the function of producing cytokines was restored.

Figure 11A:
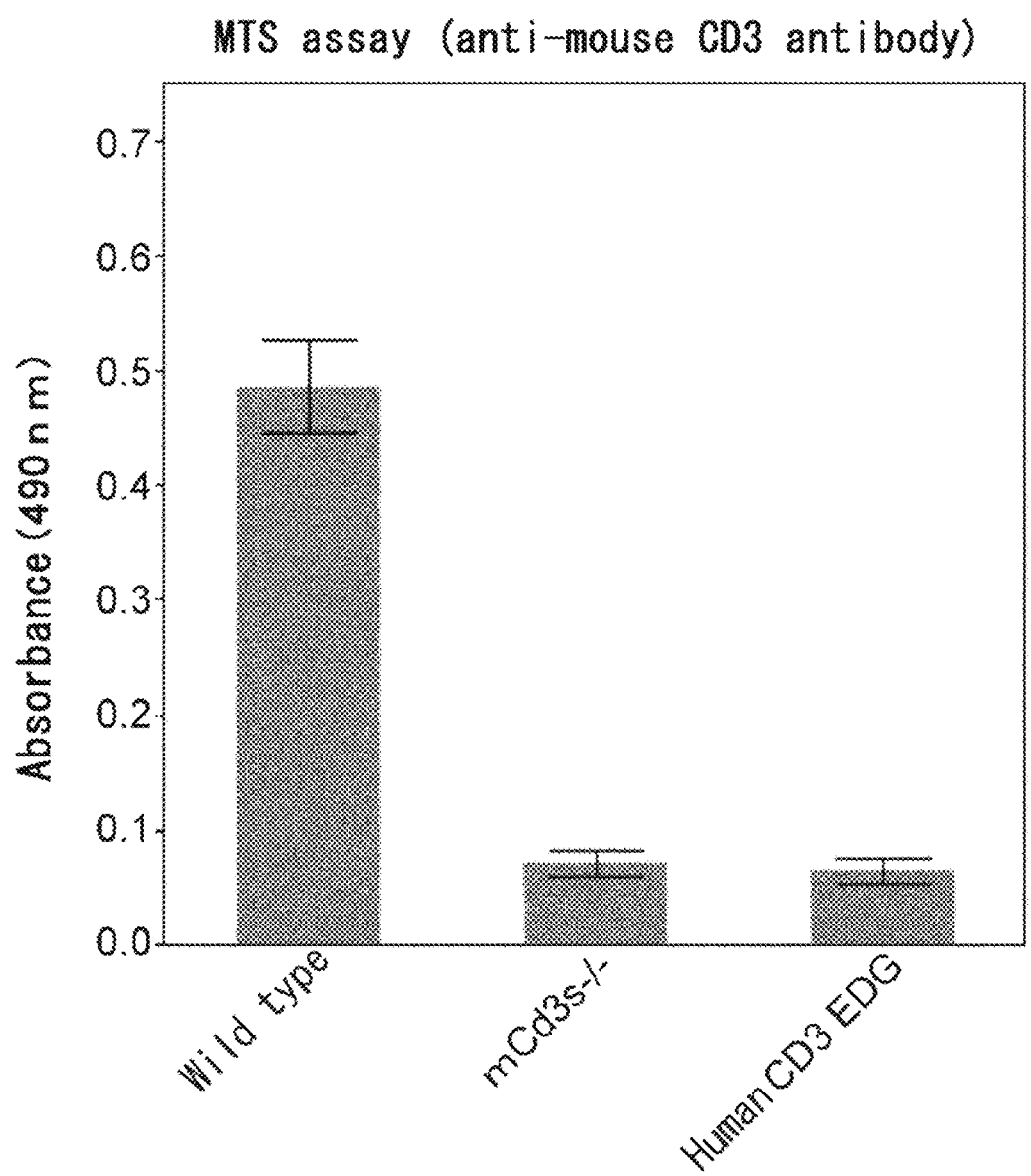
FIGS. 11A to 11D present the anti-CD3 antibody-stimulated cell proliferation activities (FIGS. 11A and 11B) and cytokine productions (FIGS. 11C and 11D) by spleen cells from the human CD3 gene-substituted mice (1C3), Cd3 gene-deficient mice, and wild-type mice. The established human CD3 gene-substituted mice (1C3) responded specifically to the anti-human CD3 antibody stimulation, and showed cell proliferation activity and cytokine production.
Figure 11B:
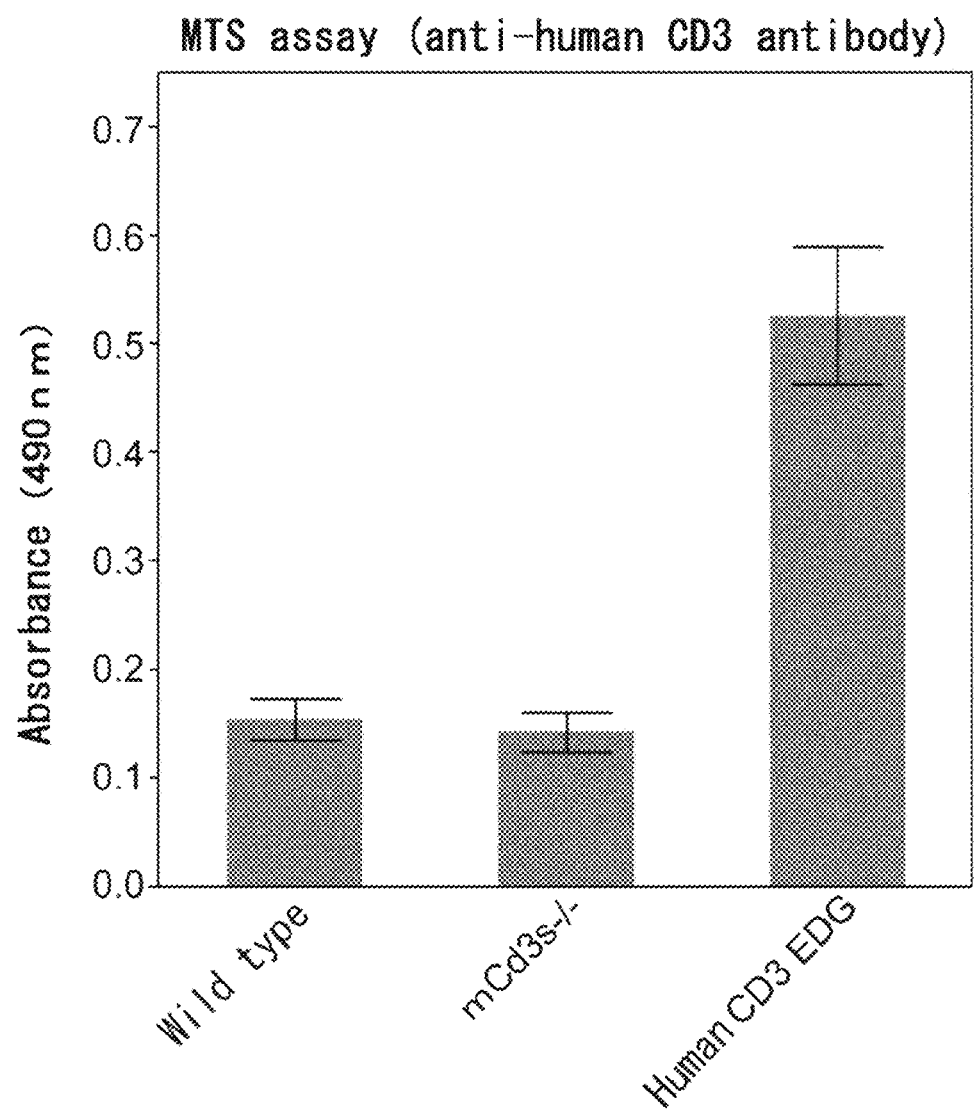
Figure 11C:
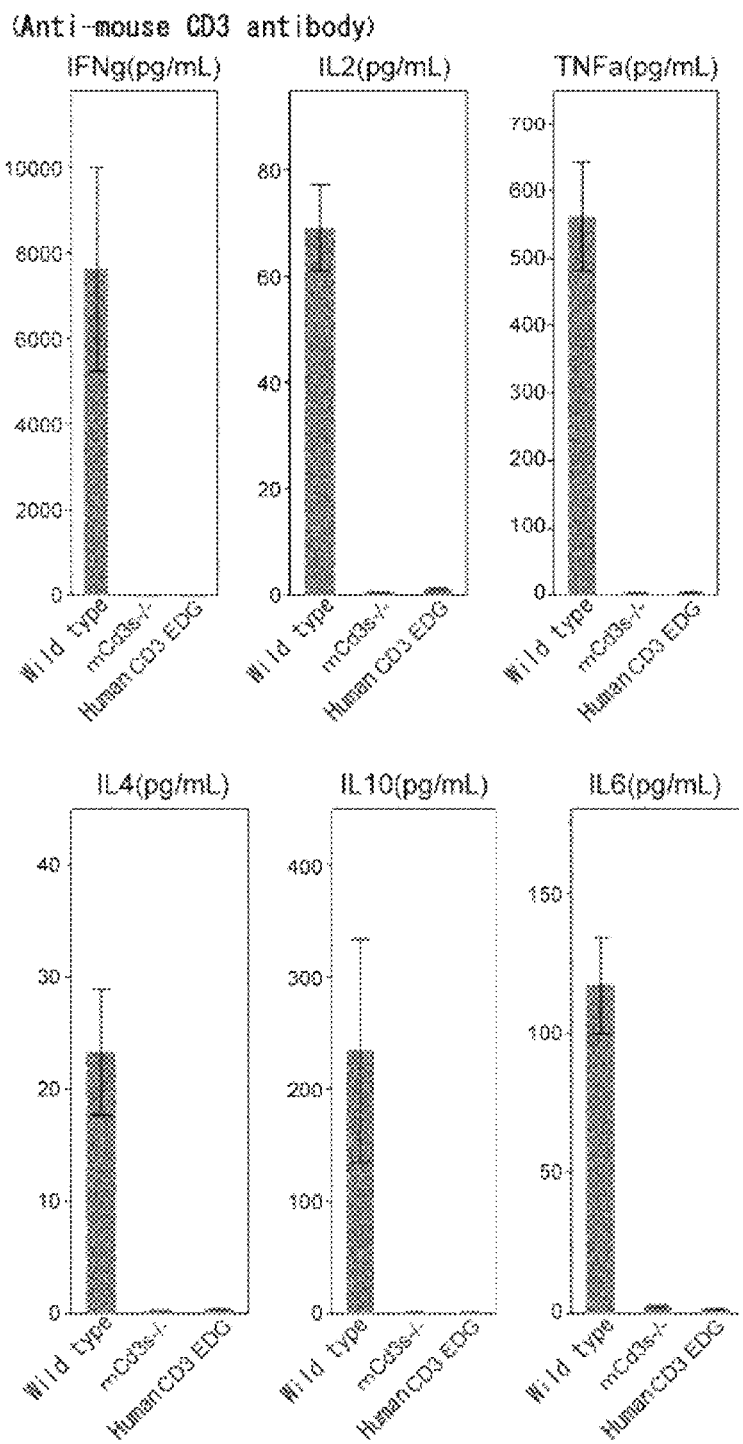

Example 4: Evaluation of Responsiveness to Human CD3 Antibody in Spleen Cells of Human CD3 Gene-Substituted Mice Spleen cells were prepared by collecting spleens from mice, isolating cells using 70 μm mesh, and lysing erythrocytes by adding a hemolytic agent. Cells were seeded into an anti-human CD3 antibody-coated plate, and MTS assay was performed to evaluate the cell proliferation activities after culturing for three days (FIGS. 11A and 11B). Cytokines produced in the culture medium were also measured (FIGS. 11C and 11D).

Figure 11D:
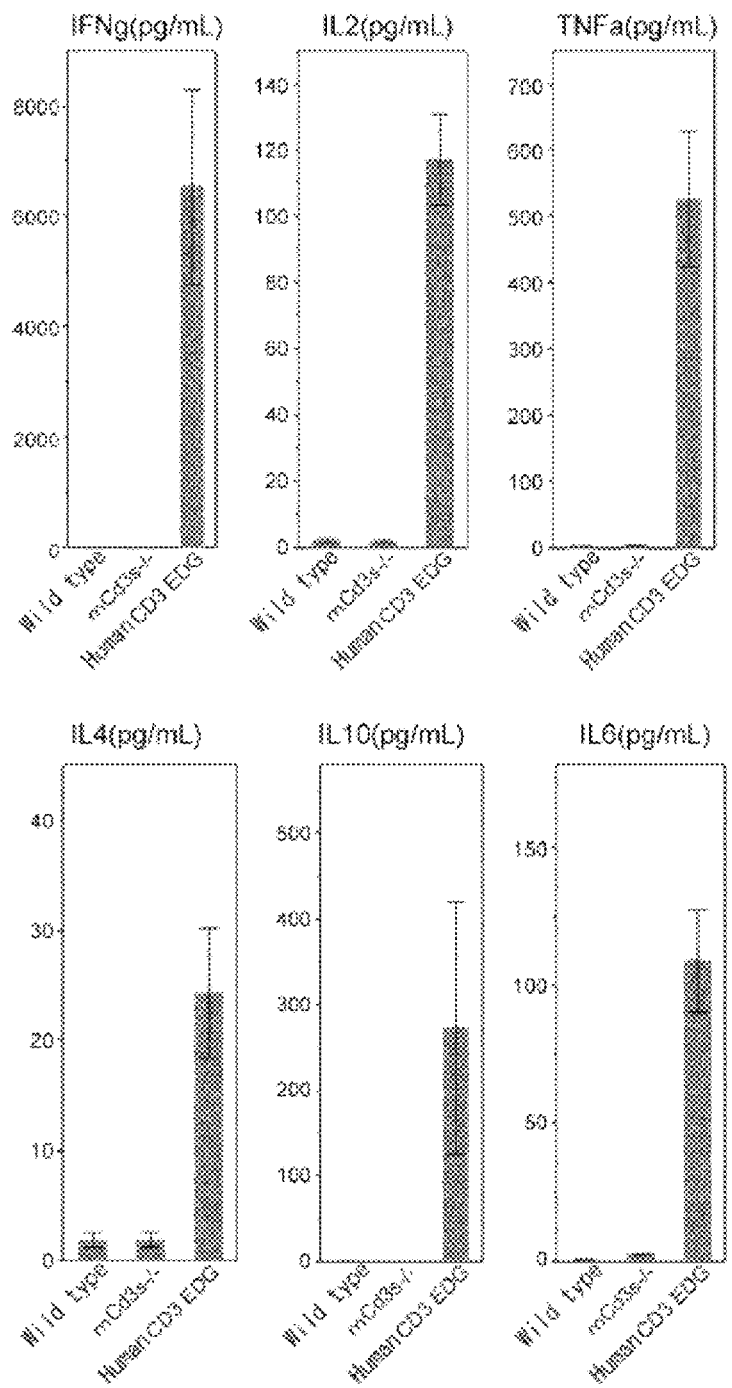

The results revealed that human CD3 gene-substituted mice responded specifically to stimulation by anti-human CD3 antibodies to exert cell proliferation activity (FIG. 11B) and cytokine production (FIG. 11D). Those levels were almost the same as the responsiveness of wild-type mice to anti-mouse CD3 antibody stimulation. These results showed that the human CD3 gene-substituted mice express human CD3s having normal functions.

Example 5: Evaluation of Immune Function of Human CD3 Gene-Substituted Mice (1) Examination of the Ability to Produce Specific Antibodies in Response to Immunization to Foreign Antigen For production of specific antibodies against foreign antigens, there must exist functional helper T cells that can bind to antigenic peptides presented together with major histocompatibility complex (MHC) antigens on the surface of antigen-presenting cells such as dendritic cells, and the T cells must have functions of giving instructions to antibody-producing cells to produce appropriate antibodies. Whether the above-mentioned human CD3 gene-substituted mice carry helper T cells having normal functions and produce specific antibodies in response to immunization to foreign antigens was examined. Immunization was carried out using chicken ovalbumin (OVA) as the sensitizing antigen together with Freund's adjuvant. Immunization to OVA was performed twice with a four-week interval. More specifically, the first immunization was performed by subcutaneously applying, 100 μg of OVA per animal with complete Freund's adjuvant to the dorsal region, and four weeks later, similar immunization was performed by subcutaneously applying the antigen with incomplete Freund's adjuvant to the dorsal region. As human CD3 gene-substituted mice, two lines (line nos. 1C3 and 8112), each of which is derived from a different modified ES cell clone, were selected, and compared to human CD3ε-overexpressing mice. Furthermore, as controls, wild-type mice and Cd3 gene-deficient mice were selected and similar antigen immunizations were performed.

Figure 12:
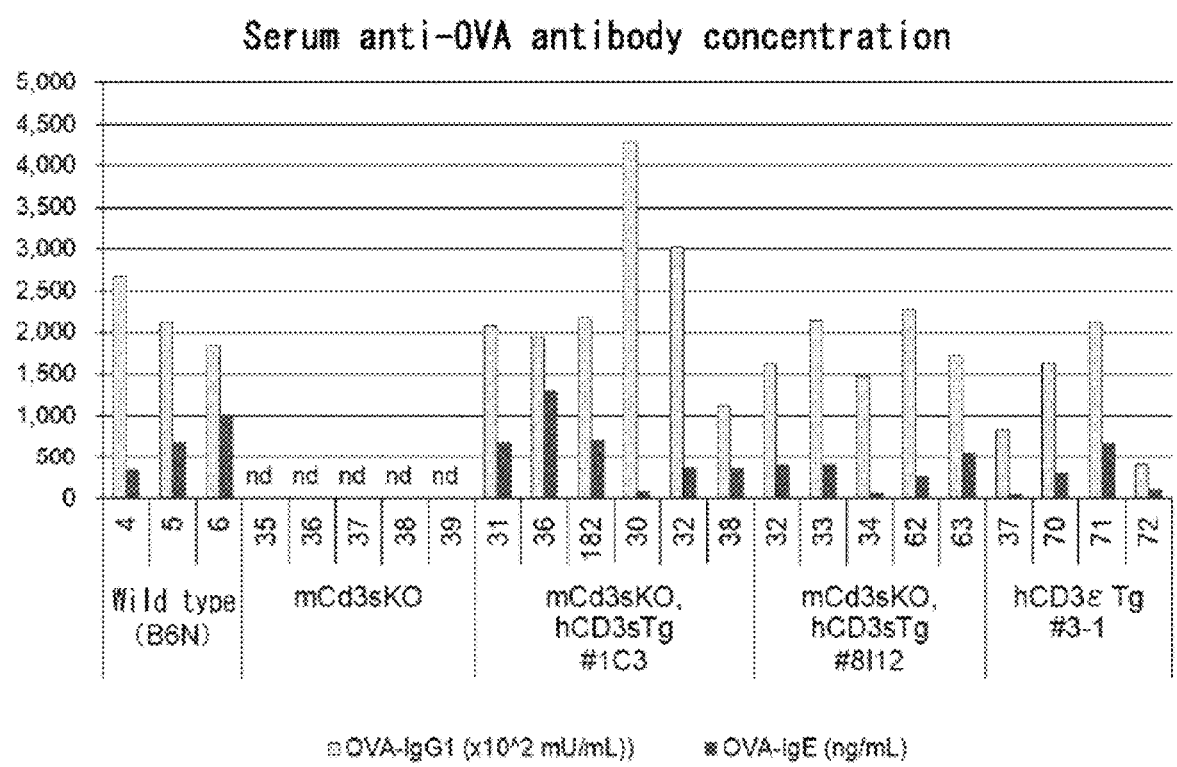
FIG. 12 presents the results of measuring the chicken ovoalbumin (OVA)-specific IgG1 and IgE serum concentrations in each established line of human CD3-substituted mice immunized with OVA. The OVA-specific serum IgG1 and IgE concentrations for each individual are shown as a bar graph. The numbers below the bar graph indicate the individual identification numbers.

One week after the second immunization, the animals were subjected to laparotomy under isoflurane anesthesia, and then euthanized by collecting whole blood and allowing bleeding from the abdominal vena cava. Serum was separated from the collected blood, and the concentrations of OVA-specific IgG1 and OVA-specific IgE were measured (FIG. 12).

As a result, neither IgG1 type nor IgE type OVA-specific antibodies were detected from the serum of mouse Cd3-deficient mice, whereas OVA-specific IgG1 and IgE were detected in both lines of the human CD3 gene-substituted mice, and their levels were equivalent to those of wild-type mice. These results showed that human CD3 gene-substituted mice have normal ability to produce antibodies in response to foreign antigen immunization.

Example 6: Antitumor Effects of Anti-Human HER2 Anti-Human CD3 Bispecific Antibodies on Human HER2-Expressing Mouse Hepatocellular Carcinoma Cell Line-Engrafted Model (1) Cell Line Hepa1-6 cells forced to express human HER2 (Hepa1-6/HER2) were used. The Hepa1-6/HER2 cells were maintained and passaged in Dulbecco's Modified Eagle's Medium (manufactured by SIGMA) containing 10% FBS (manufactured by BOVOGEN) and 0.5 mg/mL Zeocin (manufactured by Nacalai Tesque).

(2) Preparation of Hepa1-6/HER2 Engrafted Models

Hepa1-6/HER2 cells were prepared at $1\times10^8$ cells/mL in Dulbecco's Modified Eagle's Medium (manufactured by SIGMA) and MATRIGEL. A 1004 portion of this cell suspension ($1\times10^7$ cells/mouse) was transplanted subcutaneously in the abdominal region of mCd3 KO homo, hCD3 Tg-type mouse #1C3 (19-week old). The tumor volume was calculated using the following equation, and when the tumor volume reached 160-234 mm$^3$, the model was determined to be established.

Tumor volume=long diameter×short diameter×short diameter/2

(3) Preparation of a Pharmaceutical Agent for Administration

Bispecific antibody against Her2 and CD3 (HER2_CD3 antibody) was prepared at 0.5 mg/mL using PBS(-) (5 mg/kg administration group). HER2_CD3 antibody (HER2-binding H chain variable region: SEQ ID NOs: 38 and 39; HER2-binding L chain variable region: SEQ ID NOs: 40 and 41; CD3-binding H chain variable region: SEQ ID NOs: 42 and 43; and CD3-binding L chain variable region: SEQ ID NOs: 44 and 45) was prepared according to a method known to those skilled in the art.

(4) Administration of a Pharmaceutical Agent

The Hepa1-6/HER2 engrafted models prepared in (2) were grouped according to the tumor volume, and the antibody samples prepared in the above-mentioned (3) were administered at 10 mL/kg through the tail vein. As a negative control, PBS(-) (Vehicle)

(5) Evaluation of Antitumor Effects

Figure 13:
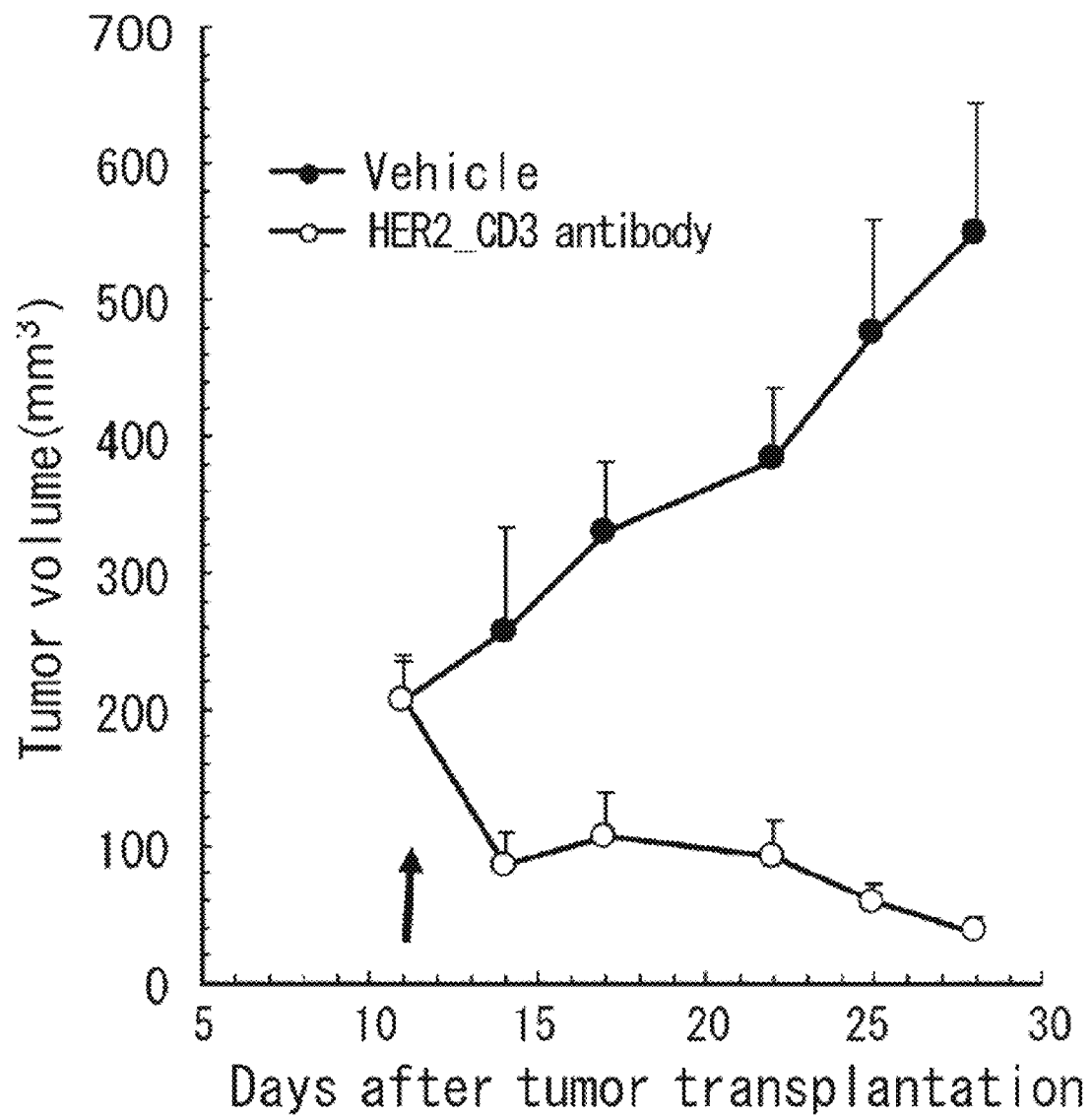
FIG. 13 presents the change in tumor volume in Hepa1-6/HER2 cell-transplanted hCD3 transgenic mouse model to which the HER2_CD3 antibody was administered. The arrow indicates antibody administration (*: $P<0.05$ (t-test))

The antitumor effect of the HER2_CD3 antibody in Hepa1-6/HER2 engrafted models was evaluated from the tumor volume at 28 days after transplantation (FIG. 13). JMP (SAS Institute Inc.) was used for statistical analysis, and the statistical analysis was confirmed by Wilcoxon test using the tumor volume on the final day of measurement. (Significance level was 5% on both sides.) As a result, tumor growth was found to be significantly inhibited by HER2_CD3 antibody administration.

Example 7: Antitumor Effects of Immune Checkpoint Inhibitors in Human Glypican 3 (GPC3)-Expressing Mouse Hepatocellular Carcinoma Cell Line-Engrafted Model (1) Cell Line Hepa1-6 cells forced to express human GPC3 (Hepa1-6/hGPC3) were used. The Hepa1-6/hGPC3 cells were maintained and passaged in Dulbecco's Modified Eagle's Medium (manufactured by SIGMA) containing 10% FBS (manufactured by BOVOGEN) and 0.6 mg/mL G418 (manufactured by Nacalai Tesque).

(2) Preparation of Hepa1-6/hGPC3 Engrafted Model

Hepa1-6/hGPC3 cells were prepared at $5\times10^7$ cells/mL in Dulbecco's Modified Eagle's Medium (manufactured by SIGMA) and MATRIGEL. A 200 μL portion of this cell suspension ($1\times10^7$ cells/mouse) was transplanted subcutaneously in the abdominal region of mCd3 KO homo, hCD3 Tg-type mouse #1C3 (20-week old). The tumor volume was calculated using the following equation, and when the tumor volume reached 160-300 mm$^3$, the model was determined to be established.

Tumor volume=long diameter×short diameter×short diameter/2

(3) Preparation of Pharmaceutical Agents for Administration

Anti-mouse CTLA-4 antibody (clone: UC10-4F10-11, manufactured by BioXcell), anti-mouse PD-1 antibody (clone: RMP1-14, manufactured by BioXcell), and anti-mouse PD-L1 antibody (clone: 10F.9G2, manufactured by BioXcell), which are immune checkpoint inhibitors, were prepared at 1 mg/mL (administration of 0.2 mg/head) using PBS(-).

(4) Administration of Pharmaceutical Agents

The Hepa1-6/hGPC3 engrafted models prepared in (2) were grouped according to the tumor volume, and the anti-mouse CTLA-4 antibodies, anti-mouse PD-1 antibodies, and anti-mouse PD-L1 antibodies prepared in the above-mentioned (3) were administered at 0.2 mL/mouse through the tail vein. As a negative control, PBS(-) (Vehicle) was similarly administered through the tail vein. The administration was carried out twice, which were 7 days (day of separation into groups) and 12 days (5 days after separation into groups) after tumor transplantation.

(5) Evaluation of Antitumor Effects

Figure 14:
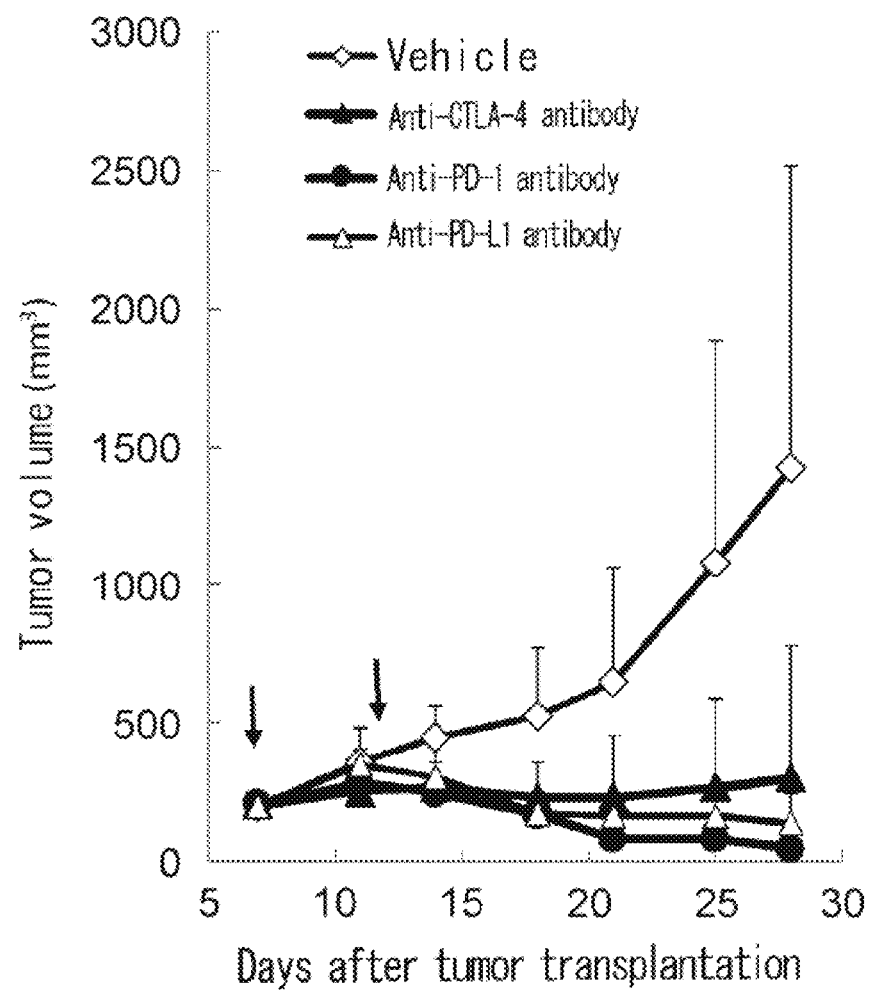
FIG. 14 presents the change in tumor volume in Hepa1-6/hGPC3 cell-transplanted hCD3 transgenic mouse model to which anti-mouse CTLA-4 antibody, anti-mouse PD-1 antibody, or anti-mouse PD-L1 antibody was administered. The arrows indicate antibody administration.

Antitumor effects in Hepa1-6/hGPC3 engrafted models were evaluated from the changes in tumor volume (FIG. 14). As a result, it was confirmed that tumor growth is inhibited by administration of the immune checkpoint inhibitors.

Example 8: Evaluation of In Vivo Drug Efficacy by Anti-Human CTLA4/Anti-Human CD3 Bispecific Antibody 8-1. Expression and Purification of a Bispecific Antibody that Binds Specifically to Human CTLA4 and Human CD3

Heavy chain variable region MDX10D1H (SEQ ID NO: 46) and light chain variable region MDX10D1L (SEQ ID NO: 47) were used for the anti-human CTLA4 arm. In that case, the constant regions used were heavy chain constant region mF18mN4 (SEQ ID NO: 48), which had been modified so that Fcγ receptor-binding is decreased and the two heavy chains undergo heterologous association, and light chain constant region mk1 (SEQ ID NO: 49). These genes were inserted into plasmids for expression in animals.

Heavy chain variable region TR01H113 (SEQ ID NO: 50) and light chain variable region L0011 (SEQ ID NO: 51) were used for the anti-human CD3 arm. In that case, the constant regions used were heavy chain constant region mF18mP4 (SEQ ID NO: 52), which had been modified so that Fcγ receptor-binding is decreased and the two heavy chains undergo heterologous association, and light chain constant region mk1 (SEQ ID NO: 49). These genes were inserted into plasmids for expression in animals.

The anti-human CTLA4 antibody and the anti-human CD3 antibody were expressed using the following method. Cells of human embryonic kidney cell-derived FreeStyle 293-F strain (Invitrogen) were suspended in FreeStyle 293 Expression Medium (Invitrogen) at a cell density of 1.33× $10^6$ cells/mL, and plated. The prepared plasmids were introduced into the cells by a lipofection method. The cells were cultured for four days in a $CO_2$ incubator (37° C., 8% $CO_2$, 90 rpm). From the culture supernatants, the antibodies were purified using Hi Trap™ Protein G HP column (GE Healthcare) by a method known to those skilled in the art. Absorbance of the purified antibody solutions at 280 nm were measured using a spectrophotometer. Concentrations of the purified antibodies were calculated from the obtained measurements using an extinction coefficient calculated by the PACE method (Protein Science (1995) 4: 2411-2423).

The respective purified homologous forms were mixed in the combinations shown in Table 3 by a method known to those skilled in the art (WO2015/046467) that utilizes charge differences of the constant regions to prepare the bispecific antibodies of interest.

TABLE 3

| No. | Clone name | Antibody 1 | Antibody 2 |
|---|---|---|---|
| 1 | MDX10//TR01H113 | MDX10-mF18mN4 | TR01H113/L0011-mF18mP4 |

8-2. Evaluation of Antitumor Effects in Syngeneic Tumor Line-Engrafted Mouse Model 8-2-1. Cell Line Colon 38 cells transferred from the Japanese Foundation for Cancer Research were used. Colon 38 cells were maintained and passaged in RPMI1640 (manufactured by SIGMA) containing 10% FBS (manufactured by SIGMA).

8-2-2. Preparation of Syngeneic Tumor Line-Engrafted Mouse Model

A human CD3 gene-substituted and human CTLA4 gene-substituted mouse was established by crossing a human CD3 gene-substituted mouse with a human CTLA4 gene-substituted mouse (Blood 2005 106: 3127-3133), and used as a mouse model for evaluating antitumor effects.

Colon 38 was used as the tumor cell line to be transplanted autologously to mice. The cells were transplanted subcutaneously to the mice, and when the volume of the grafted tumor reached approximately 100 mm³ or greater, the model was determined to be established. The volume of the grafted tumor was calculated by the following equation Tumor volume=long diameter×short diameter×short diameter/2

8-2-3. Preparation of Pharmaceutical Agents for Administration

Anti-human CTLA4/anti-human CD3 bispecific monoclonal antibody (MDX10//TR01H113) prepared in 8-1 was used as the pharmaceutical agent for administration to Colon 38 cell-engrafted models. Histidine buffer (150 mM NaCl/20 mM His-HCl buffer, pH 6.0; hereinafter, simply referred to as buffer) was used as the vehicle, and the antibody was prepared at 1000 μg/mL.

8-2-4. Administration of Pharmaceutical Agents

In the evaluation of the MDX10//TR01H113 antibody using Colon 38 cell-engrafted models, on the 12th day after transplantation, MDX10//TR01H113 was administered at 200 μg/mouse, or for the Control group (vehicle-administered group), the buffer was administered at 0.2 mL/mouse, through the tail vein.

Details relating to treatment with the pharmaceutical agents are shown in Table 4.

TABLE 4

| Colon 38 cell-engrafted model (MDX10//TR01H113 administration experiment) | | | | |
|---|---|---|---|---|
| Group | Number of animals | Pharmaceutical agent | Dose | Method of administration | Day of administration |
| 1 | 5 | Buffer | — | Tail vein | 12 days after transplantation |
| 2 | 5 | MDX10//TR01H113 | 200 μg/mouse | Tail vein | 12 days after transplantation |

8-2-5. Evaluation of Antitumor Effects

Antitumor effects were evaluated from the tumor volumes calculated using the equation shown in 8-2-2. JMP™ 11.2.1 (SAS Institute Inc.) was used for statistical analysis.

Figure 15:
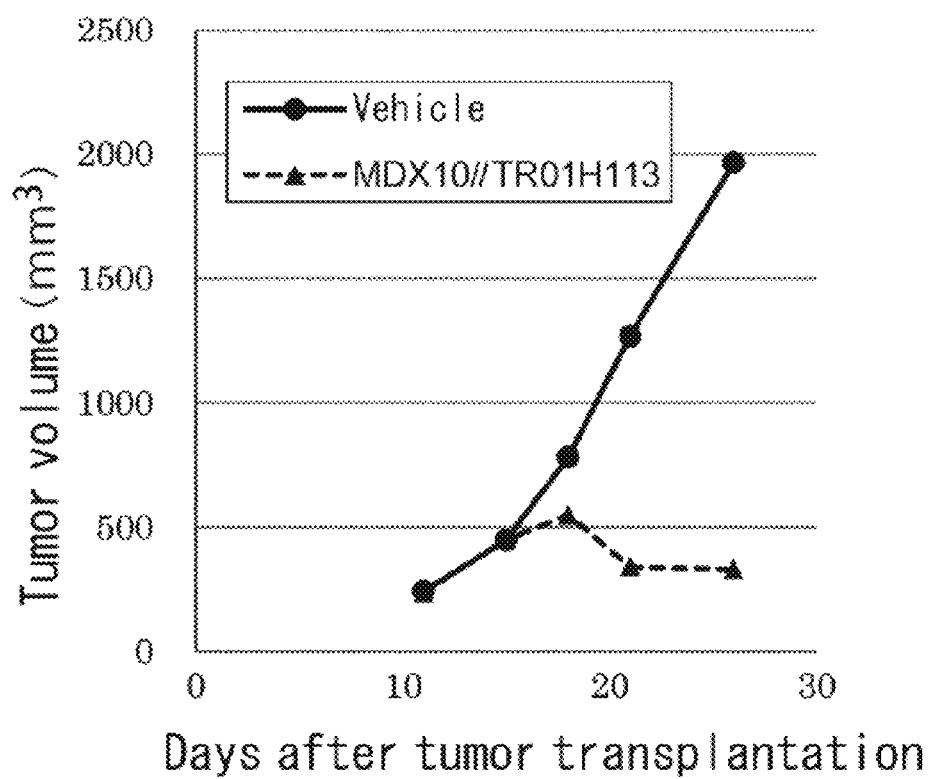
FIG. 15 presents the change in tumor volume in Colon 38 cell line-transplanted mouse model to which MDX10//TR01H113 or the buffer as a control (in the figure, referred to as "MDX10//TRO01H1333" and "vehicle", respectively) was administered. Each point shows the mean value of tumor volumes for n=5 per group. When the mean values were compared at the final measurement points, significant difference was observed between the two groups, the MDX10//TR01H113-administered group and the buffer-administered group (p=0.0021, Student's t-test).

As a result, compared to the control group, tumor growth was found to be significantly inhibited by anti-mouse CTLA4/CD3 bispecific monoclonal antibody administration (FIG. 15).

INDUSTRIAL APPLICABILITY

The present invention provides non-human animals in which the expression of their endogenous CD3 genes is deleted and the expression of human CD3 genes is enabled at a physiologically appropriate level; methods for evaluating compounds using such animals; and such. Therefore, the present invention can be used particularly for the development of therapeutic agents having drug efficacy of killing tumor cells by T cell activation mediated by human CD3 molecules.

The invention claimed is:

1. A genetically modified mouse, wherein a mouse CD3 gene region encoding full-length mouse CD3ε, CD3δ, and CD3γ proteins is substituted with a human CD3 gene region encoding full-length human CD3ε, CD3δ, and CD3γ proteins in its genome and wherein the mouse functionally expresses the full-length human CD3ε, CD3δ, and CD3γ proteins on T cells.

2. The genetically modified mouse of claim 1, wherein the mouse functionally expresses the full-length human CD3ε, CD3δ, and CD3γ proteins on activated T cells.

3. The genetically modified mouse of claim 1, wherein the mouse-derived T cell receptor (TCR) and human CD3ε, CD3δ, and CD3γ proteins form a functional TCR complex on the cell membrane of the T cells of the mouse.

4. The genetically modified mouse of claim 1, which further comprises a transplanted cancer cell.

5. The genetically modified mouse of claim 4, wherein the cancer cell is derived from lung cancer, gastric cancer, liver cancer, esophageal cancer, or ovarian cancer.

6. The genetically modified mouse of claim 5, wherein the cancer cell is a HER2-positive cell.

7. The genetically modified mouse of claim 4, wherein the cancer cell expresses a human cancer antigen.

8. The genetically modified mouse of claim 5, wherein the cancer cell expresses a human cancer antigen.

* * * * *